US008147414B2

(12) United States Patent
Abraham

(10) Patent No.: US 8,147,414 B2
(45) Date of Patent: Apr. 3, 2012

(54) IMAGE GUIDED CATHETER HAVING REMOTELY CONTROLLED SURFACES-MOUNTED AND INTERNAL ULTRASOUND TRANSDUCERS

(75) Inventor: Theodore P. Abraham, Baltimore, MD (US)

(73) Assignee: InnoScion, LLC, Baltimore, MD (US)

( * ) Notice: Subject to any disclaimer, the term of this patent is extended or adjusted under 35 U.S.C. 154(b) by 748 days.

(21) Appl. No.: 12/285,779

(22) Filed: Oct. 14, 2008

(65) Prior Publication Data

US 2009/0105597 A1   Apr. 23, 2009

Related U.S. Application Data

(63) Continuation-in-part of application No. 12/182,247, filed on Jul. 30, 2008, now Pat. No. 8,038,622, and a continuation-in-part of application No. 11/871,282, filed on Oct. 12, 2007, and a continuation-in-part of application No. 11/782,991, filed on Jul. 25, 2007.

(60) Provisional application No. 60/953,861, filed on Aug. 3, 2007, provisional application No. 60/851,451, filed on Oct. 12, 2006.

(30) Foreign Application Priority Data

Oct. 12, 2007  (WO) ................ PCT/US2007/081185
Aug. 1, 2008   (WO) ................ PCT/US2008/071943

(51) Int. Cl.
*A61B 8/14* (2006.01)

(52) U.S. Cl. ........................................ 600/466; 600/459

(58) Field of Classification Search .......... 600/437–438, 600/459, 462–467
See application file for complete search history.

(56) References Cited

U.S. PATENT DOCUMENTS

| 3,556,079 | A |   | 1/1971  | Omizo |
| 3,612,050 | A |   | 10/1971 | Sheridan |
| 4,092,867 | A |   | 6/1978  | Matzuk |
| 4,327,709 | A |   | 5/1982  | Hanson et al. |
| 4,483,344 | A | * | 11/1984 | Atkov et al. ................ 600/459 |
| 4,554,927 | A |   | 11/1985 | Fussell |
| 4,869,258 | A |   | 9/1989  | Hetz |
| 5,106,368 | A |   | 4/1992  | Uldall et al. |
| 5,159,931 | A | * | 11/1992 | Pini ............................. 600/443 |
| 5,181,514 | A | * | 1/1993  | Solomon et al. ............ 600/444 |
| 5,381,794 | A | * | 1/1995  | Tei et al. .................... 600/459 |
| 5,398,691 | A | * | 3/1995  | Martin et al. ............... 600/463 |

(Continued)

FOREIGN PATENT DOCUMENTS

CA      2 376 103      1/2002

*Primary Examiner* — Francis Jaworski
(74) *Attorney, Agent, or Firm* — Cameron LLP

(57) ABSTRACT

A remotely manipulatable ultrasound transducer element or transducer array permits an operator of an ultrasound system to be remotely located from a patient and yet remotely control the location of the element or array on a patient's body such as on the skin surface or within a body cavity. The transducer element or transducer array associated with motors and control circuits comprises an assembly within a housing for fixation to or within a human body. The transducer assembly may be fixed to a ring surrounding an image guided catheter and may rotate about the image guided catheter or move along its length to an anchoring position proximate the surface skin. Two embodiment systems for pericardial access may comprise surface and internal vision or ultrasound guidance systems that are wireless or wired one operating on suction and another on mechanical grasping of the pericardial lining.

19 Claims, 32 Drawing Sheets

U.S. PATENT DOCUMENTS

| | | | | |
|---|---|---|---|---|
| 5,454,373 | A | 10/1995 | Koger et al. | |
| 5,465,724 | A | 11/1995 | Sliwa, Jr. et al. | |
| 5,505,088 | A | 4/1996 | Chandraratna et al. | |
| 5,701,901 | A | 12/1997 | Lum et al. | |
| 5,704,361 | A * | 1/1998 | Seward et al. | 600/459 |
| 5,967,984 | A | 10/1999 | Chu et al. | |
| 5,997,497 | A | 12/1999 | Nita et al. | |
| 6,068,638 | A | 5/2000 | Makower | |
| 6,120,453 | A * | 9/2000 | Sharp | 600/463 |
| 6,149,598 | A | 11/2000 | Tanaka | |
| 6,162,179 | A | 12/2000 | Moore | |
| 6,171,247 | B1 * | 1/2001 | Seward et al. | 600/459 |
| 6,254,573 | B1 | 7/2001 | Haim et al. | |
| 6,261,234 | B1 * | 7/2001 | Lin | 600/461 |
| 6,267,770 | B1 * | 7/2001 | Truwit | 606/130 |
| 6,306,097 | B1 | 10/2001 | Park et al. | |
| 6,527,718 | B1 * | 3/2003 | Connor et al. | 600/439 |
| 6,547,737 | B2 * | 4/2003 | Njemanze | 600/454 |
| 6,558,326 | B2 | 5/2003 | Pelissier | |
| 6,565,513 | B1 * | 5/2003 | Phillips | 600/454 |
| 6,572,551 | B1 | 6/2003 | Smith et al. | |
| 6,592,559 | B1 | 7/2003 | Pakter et al. | |
| 6,685,648 | B2 | 2/2004 | Flaherty | |
| 6,689,062 | B1 * | 2/2004 | Mesallum | 600/439 |
| 6,690,963 | B2 * | 2/2004 | Ben-Haim et al. | 600/424 |
| 6,730,034 | B1 * | 5/2004 | Lang et al. | 600/449 |
| 6,884,217 | B2 * | 4/2005 | McMorrow et al. | 600/443 |
| 7,037,267 | B1 * | 5/2006 | Lipson et al. | 600/454 |
| 7,100,614 | B2 * | 9/2006 | Stevens et al. | 128/898 |
| 7,115,092 | B2 | 10/2006 | Park et al. | |
| 7,118,531 | B2 | 10/2006 | Krill | |
| 7,127,401 | B2 | 10/2006 | Miller | |
| 7,270,634 | B2 * | 9/2007 | Scampini et al. | 600/447 |
| 7,366,561 | B2 * | 4/2008 | Mills et al. | 600/417 |
| 7,488,289 | B2 * | 2/2009 | Suorsa et al. | 600/466 |
| 7,713,190 | B2 * | 5/2010 | Brock et al. | 600/114 |
| 2001/0023323 | A1 | 9/2001 | Nishtala et al. | |
| 2002/0065464 | A1 | 5/2002 | Murphy et al. | |
| 2003/0139677 | A1 | 7/2003 | Fonseca et al. | |
| 2003/0229286 | A1 | 12/2003 | Lenker | |
| 2004/0015193 | A1 | 1/2004 | Lamson et al. | |
| 2006/0106315 | A1 | 5/2006 | Edens | |
| 2007/0066894 | A1 | 3/2007 | Bartol et al. | |
| 2008/0312561 | A1 * | 12/2008 | Chauhan | 601/2 |

* cited by examiner

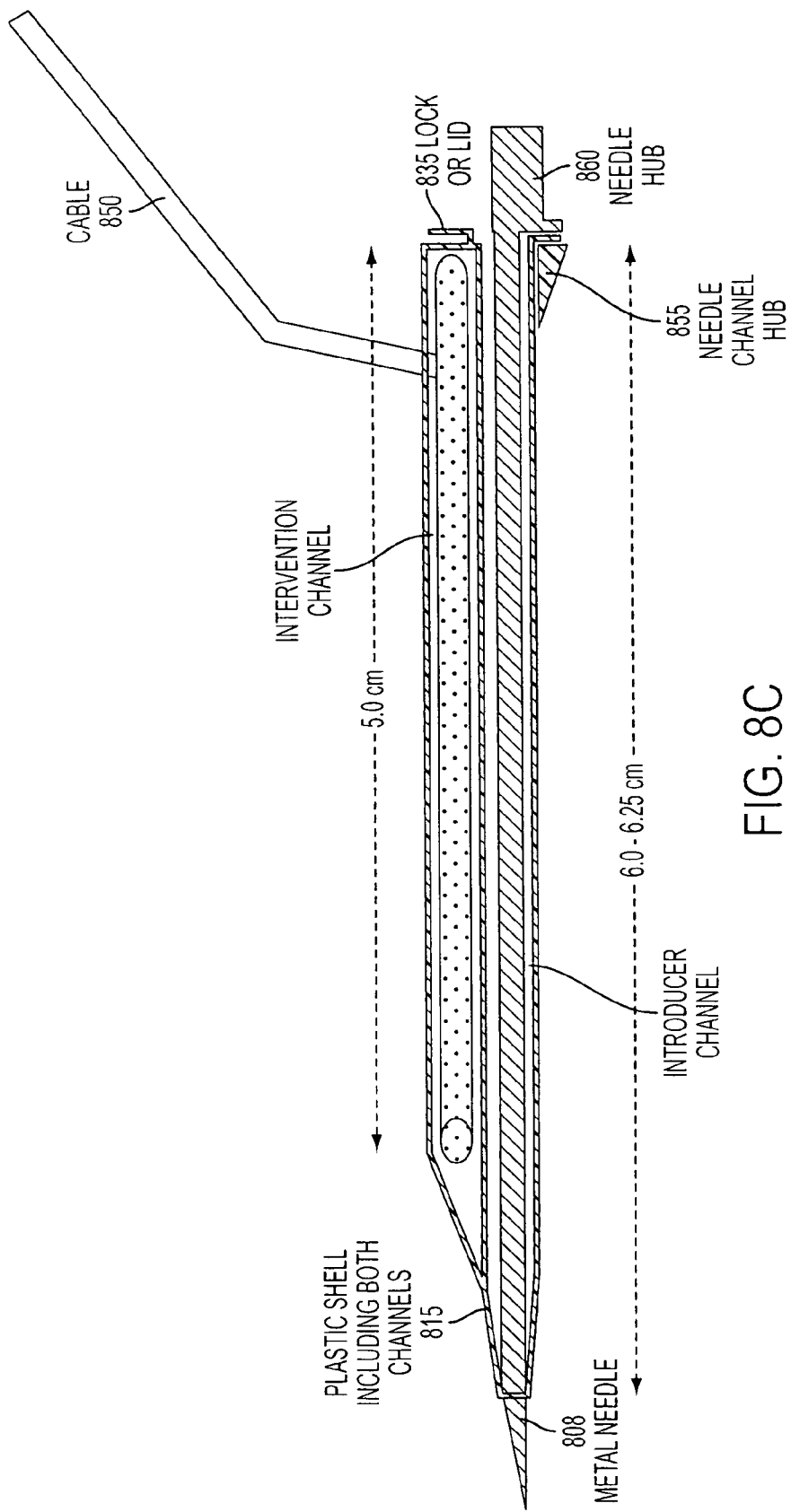

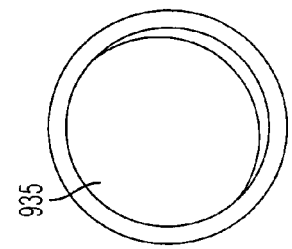
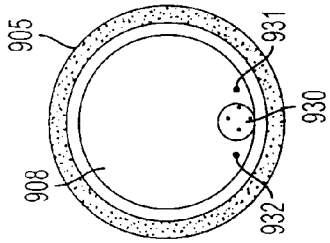
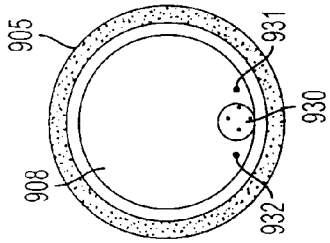
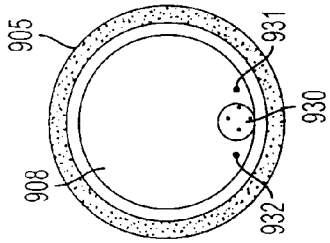
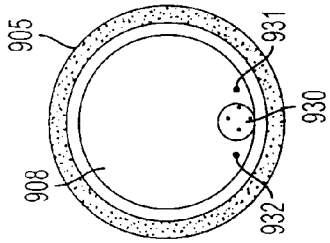
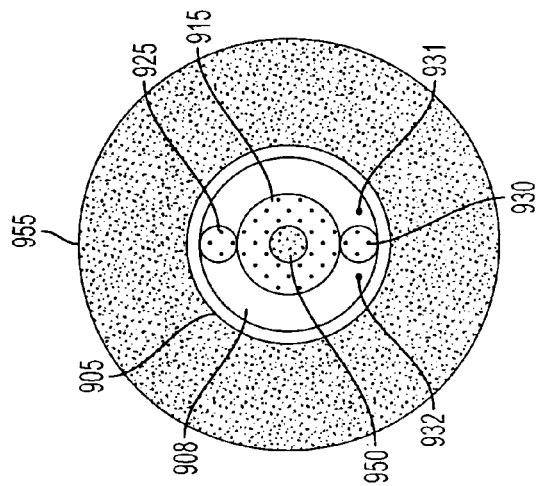
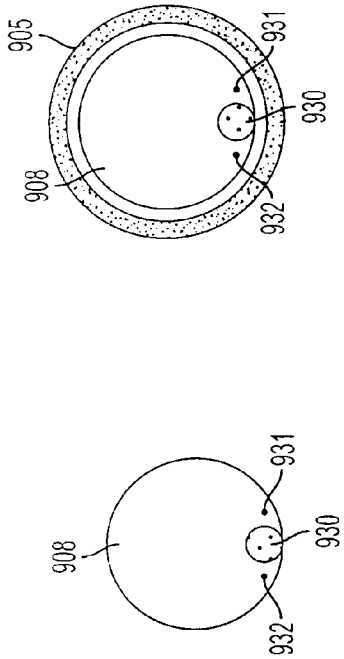
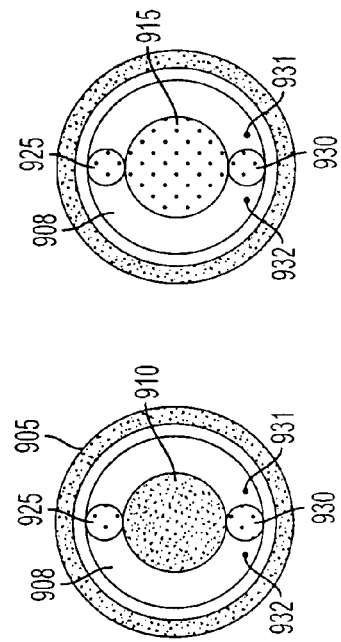

(1.) ENTIRE ASSEMBLY IS ADVANCED INTO TARGET LOCATION USING SYRINGE TO DRIVE THE NEEDLE (2.) ONCE AT TARGET, SYRINGE IS USED TO DELIVER DRUGS ETC OR EVACUATE FLUID (3.) ALTERNATIVELY - GUIDE WIRE IS INSERTED THROUGH THE CONNECTOR CHANNEL AFTER DISCONNECTING THE SYRINGE (4.) NEEDLE ASSEMBLY IS WITHDRAWN LEAVING GUIDE WIRE IN TARGET LOCATION (5.) OTHER DEVICES CAN NOW BE THREADED OVER GUIDE WIRE INTO LOCATION (6.) ALTERNATIVELY, AFTER NEEDLE IS AT TARGET LOCATION, NEEDLE IS WITHDRAWN LEAVING PLASTIC OUTER SHEATH IN PLACE (7.) TIP OF OUTER SHEATH IS IN TARGET LOCATION - NEEDLE ASSEMBLY IS PULLED OUT (8.) WITH PLASTIC SHEATH TIP IN TARGET LOCATION A SYRINGE CAN BE USED TO DELIVER OR REMOVE SUBSTANCES FROM THE TARGET LOCATION

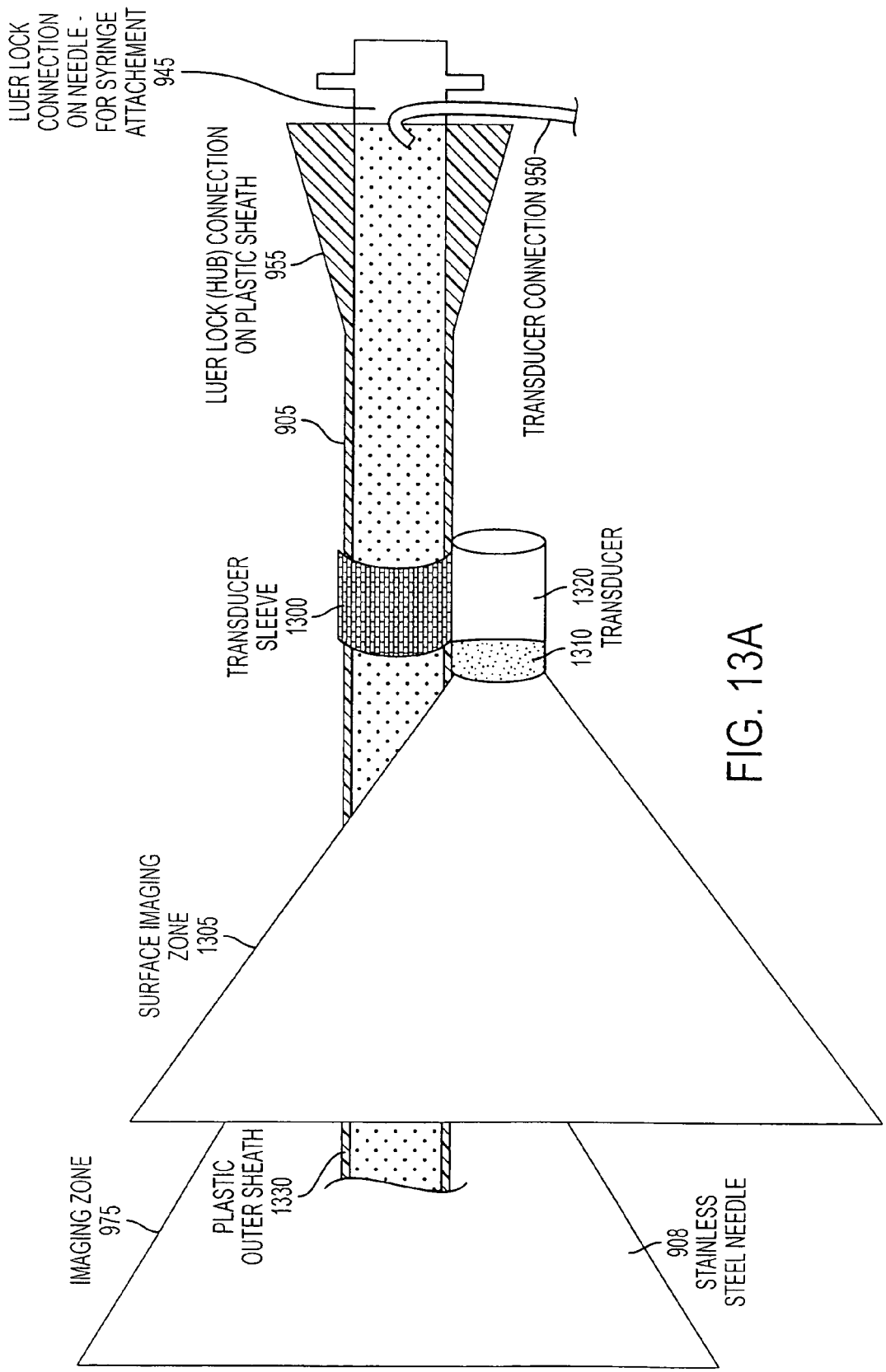

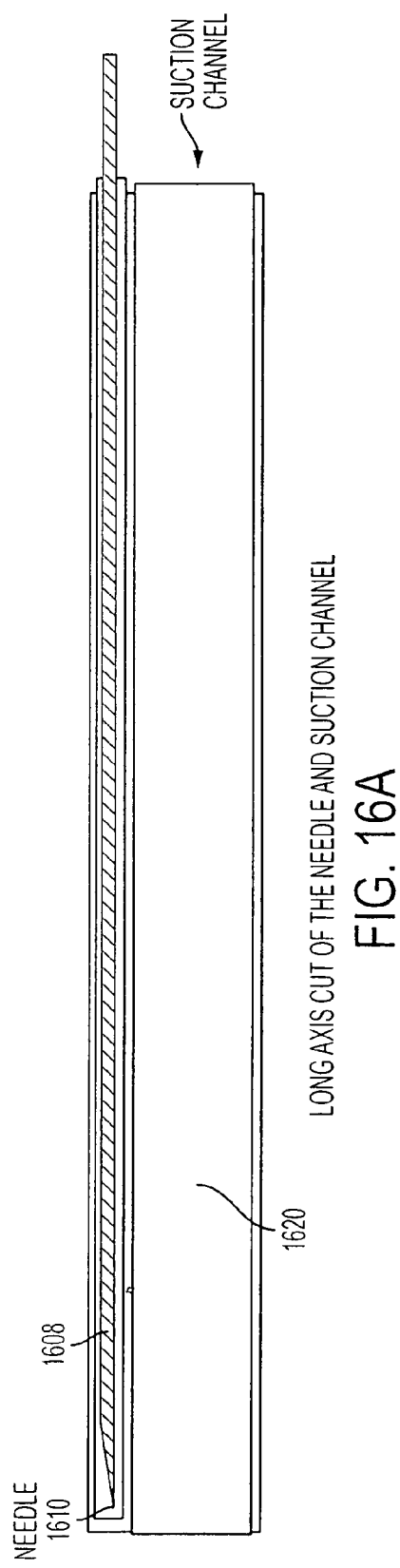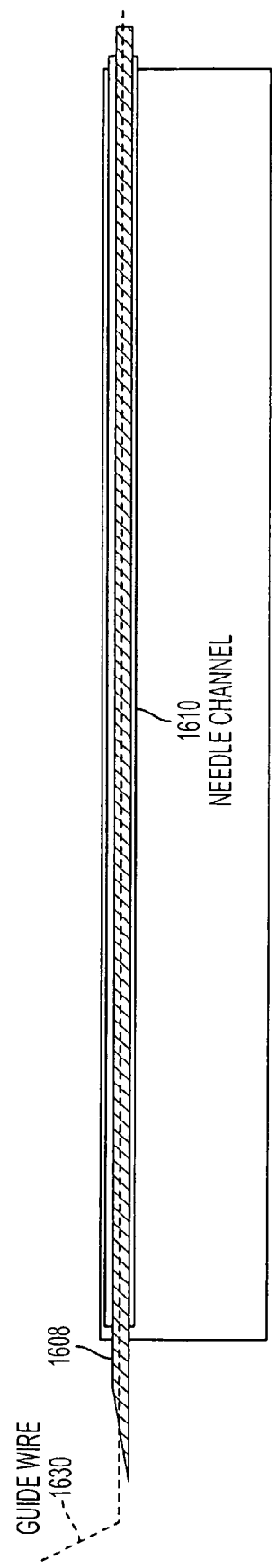

CROSS SECTION SHOWING THE NEEDLE
CHANNEL WITHIN THE SUCTION CHANNEL

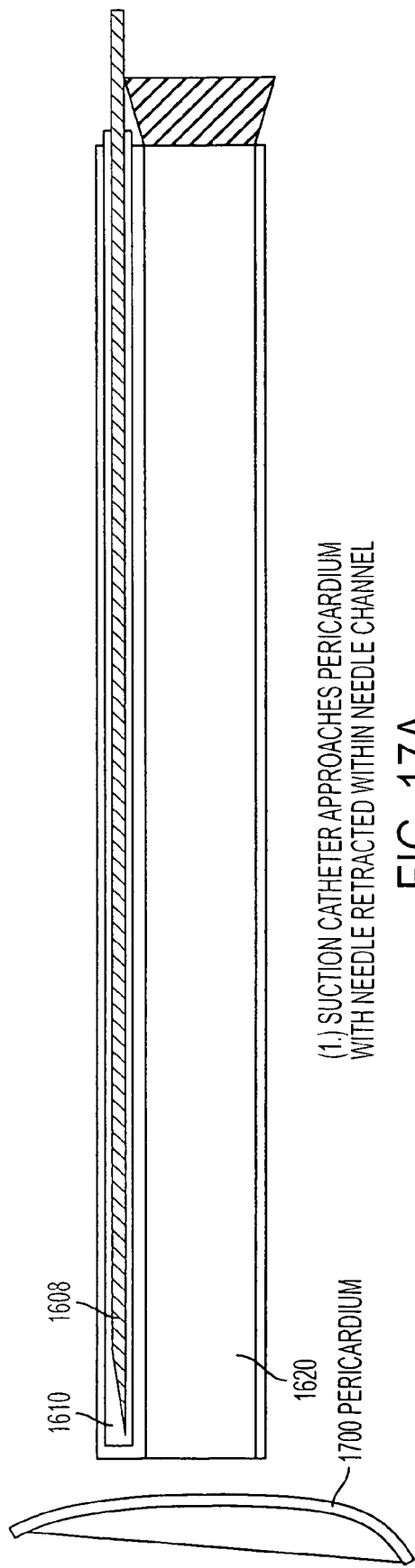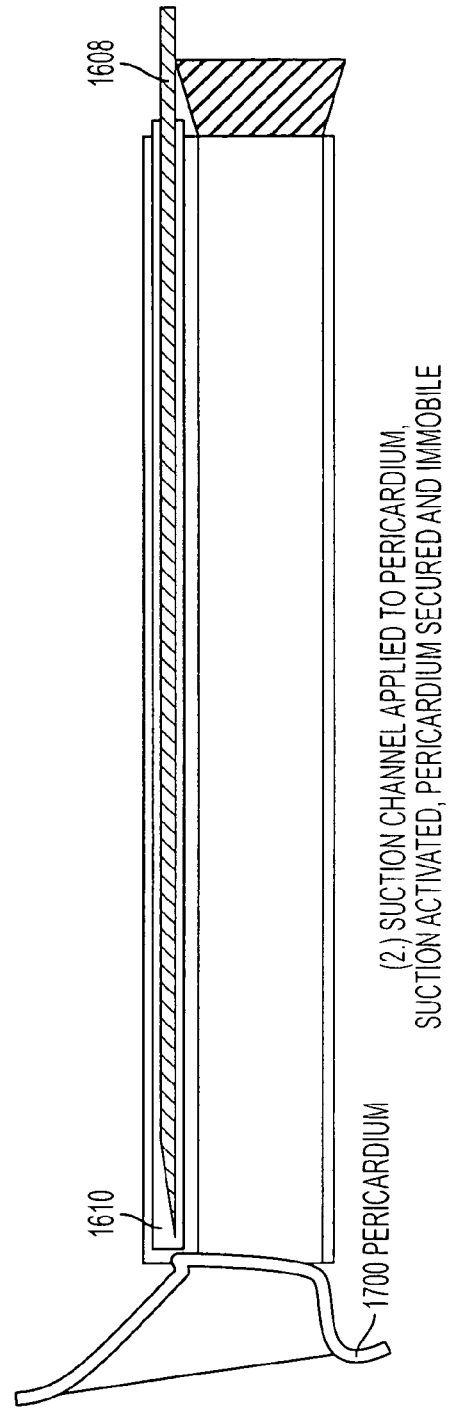

(3.) NEEDLE ADVANCED OUT OF NEEDLE CHANNEL TO PIERCE THROUGH PERICARDIUM INTO PERICARDIAL SPACE (4.) GUIDE WIRE INSERTED THROUGH NEEDLE INTO PERICARDIAL SPACE. OTHER INSTRUMENTS CAN NOW BE ADVANCED OVER THE GUIDE WIRE (1.) INSTRUMENT APPROACHES PERICARDIUM WITH TOOTHED FORCEPS RETRACTED WITHIN FORCEPS CHANNEL (2.) UNDER VISION, FORCEPS ARE ADVANCED OUT OF THEIR CHANNEL, OPENED AND APPLIED TO PERICARDIUM

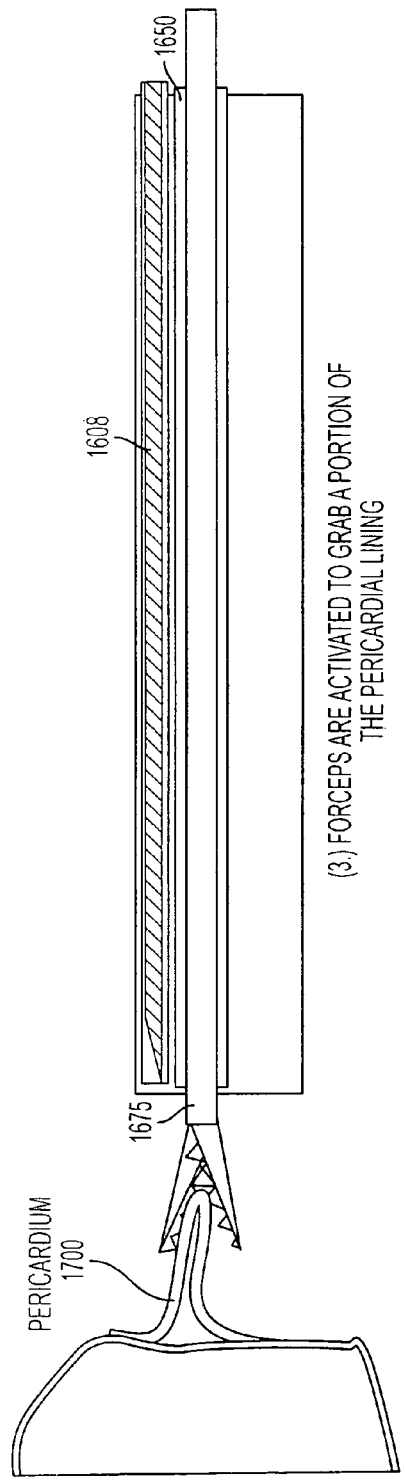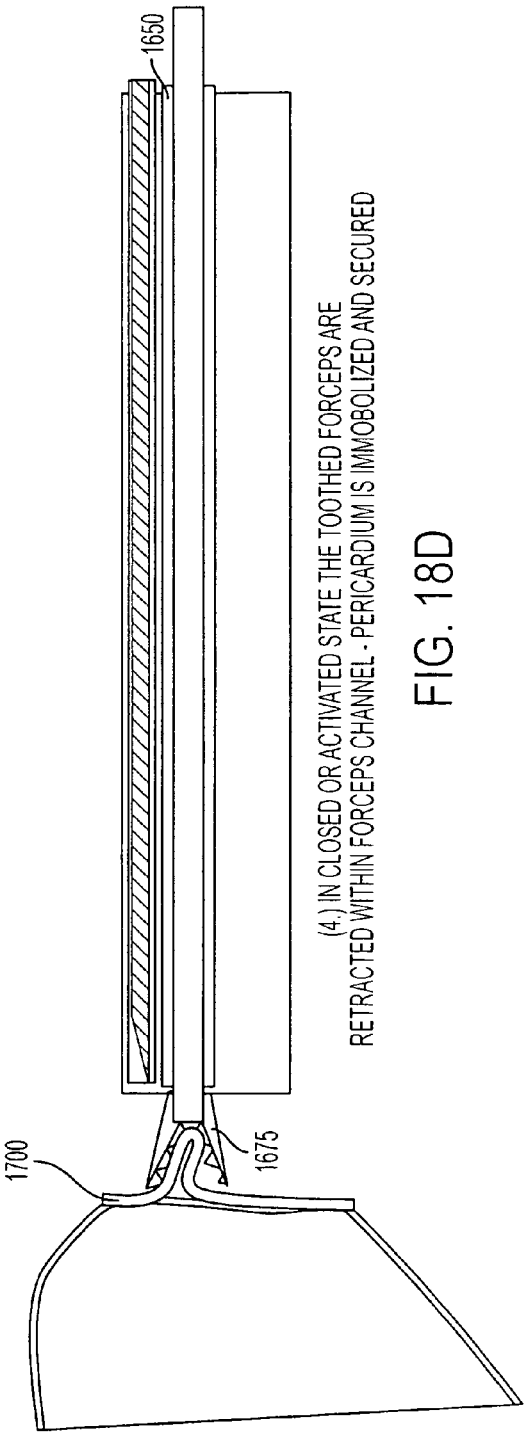

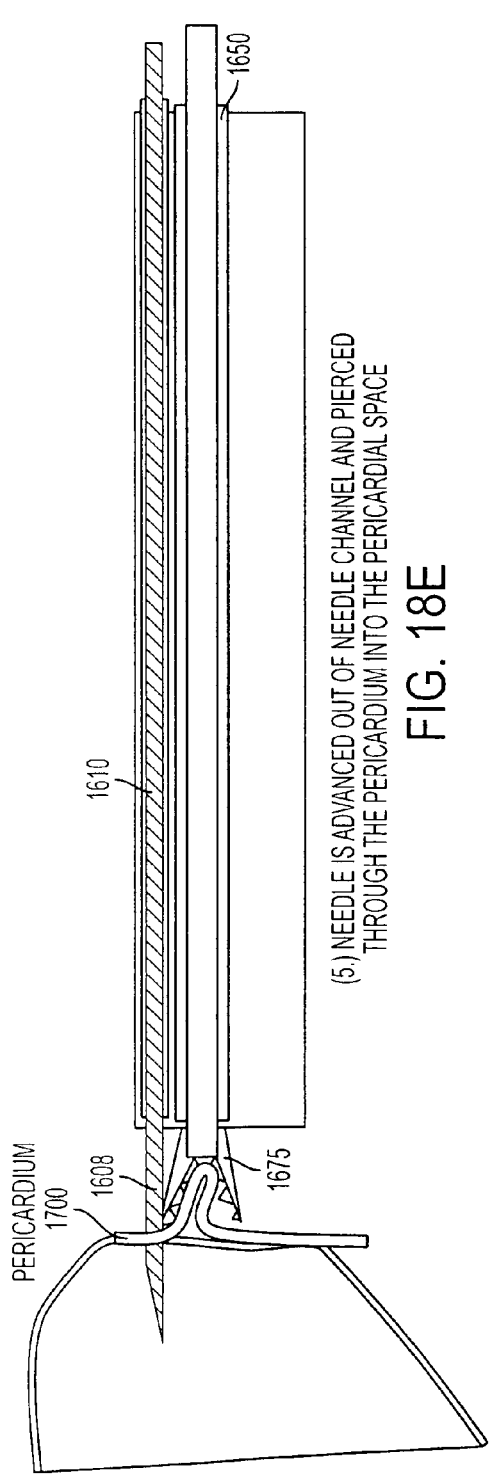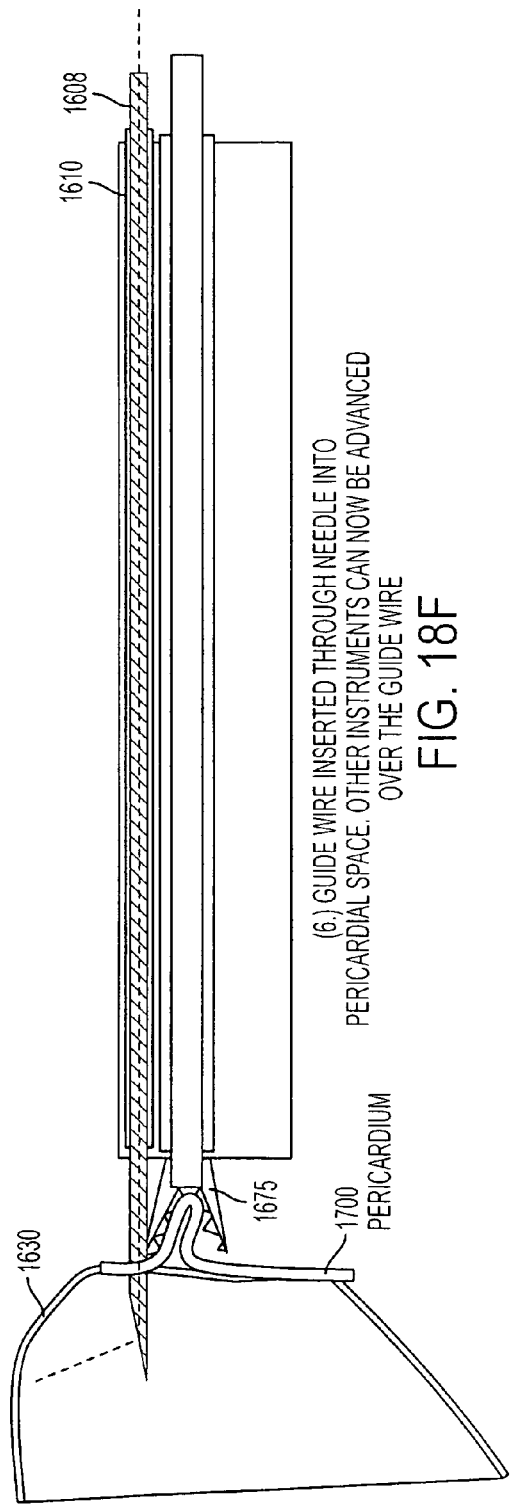

IMAGE GUIDED CATHETER HAVING REMOTELY CONTROLLED SURFACES-MOUNTED AND INTERNAL ULTRASOUND TRANSDUCERS

This application is a continuation-in-part application and claims the benefit of priority to PCT/US08/71943 filed Aug. 1, 2008 and to U.S. application Ser. No. 12/182,247, filed Jul. 30, 2008, both of which claim the benefit of priority to U.S. Provisional Patent Appl. Ser. No. 60/953,861, filed Aug. 3, 2007 and to U.S. application Ser. No. 11/871,282 filed Oct. 12, 2007, to U.S. application Ser. No. 11/871,219 filed Oct. 12, 2007, to PCT/US07/81185 filed Oct. 12, 2007 and to U.S. application Ser. No. 11/782,991 filed Jul. 25, 2007, all three of which claim the benefit of priority to U.S. Provisional Patent Application Ser. No. 60/851,451 filed Oct. 12, 2006, all of the same inventor and incorporated herein by reference as to their entire contents.

TECHNICAL FIELD

The technical field of the several embodiments of a wired or wireless ultrasonic transducer and/or image guided catheter or sheath and methods of body cavity, for example, pericardial access relates generally to the field of ultrasound and related medical imaging methods and apparatus and, more particularly, to embodiments thereof, for example, wherein the ultrasonic arrays and imaging apparatus may include surface mounted and internal to a body transducers for providing multiple views of a patient's region of interest from skin surface or from an internal body location of an image guided catheter or sheath. Moreover, smaller instrumentation requiring image guided catheters in the micron size range also are preferred for implementation into smaller body cavities and vascular systems.

BACKGROUND

Ultrasonic imaging is known in the art and systems typically involve the use of a hand-held or temporarily affixed ultrasonic transducer element or transducer array that may be controlled, for example, as to on/off, mode, focus control, depth control and the like. A qualified user applies a small amount of ultrasound gel to a region of interest, holds and moves the ultrasound transducer from one location of the patient to another within the region, the unit being wired to a console, typically including a display. The ultrasound transducer is housed in a wand that may be moved about the patient's body surface to obtain two dimensional, three dimensional or so-called four dimensional (including movement over time of the subject of the imaging) views provided on a display of the console of the region of interest. It is generally known that one may improve the image by moving the wand slightly, for example, to avoid reflections from internal body parts that are not of interest and thus obtain an improved image of a body part, such as the heart, that is of greater interest and to obtain a stronger reflected signal from the heart. Ultrasound is a biologically safe and non-radiating form of energy that can provide detailed anatomic and, in some cases, functional images. It is known in the art of transesophageal echocardiography (imagery of the heart) to provide a multi-plane transducer that can image in planes in a 180 degree range.

The advent of piezocomposite material comprising a piezoelectric ceramic and a polymer has improved performance of commonly used ultrasonic arrays. Ultrasonic arrays may be annular, rectangular (linear) and two, three or four dimensional where the fourth dimension represents movement over time in a three dimensional space. While originally analog, ultrasound imaging is now digital in order from transducer to beam former, signal processor, scan converter and a monitor or display. Imaging is similar to television reception as scan lines of an image are produced at a depth of field given by the equation $6 \times \lambda \times (FN)^2$ where FN is the ratio of focal depth and aperture and $\lambda$ is the wavelength. A plurality of lines of ultrasound picture elements (pixels) comprise a frame and a typical frame rate is 30 frames per second. For example, a transducer operating at 10 MHz operating at an f-number of 15 yields a depth of focus of about 2 cm. In a phased-array system, elements of an array are used for each interrogation pulse and various time delays are introduced between the elements. Beam steering is accomplished by varying the time delays of the individual elements. A linear array is a stacking of adjacent elements linearly, for example, 512 elements over a 75 to 120 mm length. Subgroups of elements are pulsed in delay relation to other subgroups. Distinguished from linear arrays, annular (circular) arrays vary in construction. An electronically steered-beam, phased-array has proven useful in cardiac imaging. On the other hand, phased-array transducers have not seen as extensive use as linear sequenced arrays in general ultrasound medical imaging. Real-time four dimensional imaging is known for providing motion imaging of a three dimensional space such as a pericardial cavity. Specialty arrays are known, for example, a curvilinear or convex abdominal transducer is known for providing an improved fit to an obstetric abdomen. The term "array" as used herein may be defined as a plurality of transducer elements in any one of a plurality of forms suitable to a particular purpose. Harmonic imaging is known for the transmission of a first frequency and the reception of reflections at a harmonic of the transmitted first frequency. The lower frequency transmission improves depth of penetration and the higher harmonic reception improves imaging particularly in imaging more obese patients.

Ultrasound operates on a principle of transmitting a sound wave of a given frequency range and recording the time and value of reflected wave data of a principal frequency and its harmonics from body parts of interest to the qualified user. Similarly, optical coherence tomography (OCT) utilizes a similar transmission/reflection process by transmitting light waves and recording the reflected light amplitude and delay. Light, however, may only penetrate a body to a depth of a few millimeters. Consequently, OCT has proven useful, for example, for quantifying the depth and healing over time of a third degree skin burn and underlying regions. Another field of medical imaging is infrared medical imaging where infrared energy is passively emitted by a body and provides an indication of temperature of the region imaged. An infrared camera captures the images of the infrared emission gradients which can be calibrated to show differences in temperature of adjacent regions, for example, as a yellow, orange, red scale. Infrared imaging has been found useful for imaging breast tumors and other close to the skin surface abnormalities indicated by temperature gradient.

U.S. Pat. No. 4,554,927, issued Nov. 26, 1985 to Fussell describes pressure and temperature sensors for biomedical applications wherein the sensor can be inserted into a body transcutaneously by a catheter.

It is also known, for example, in the telecommunications arts to remotely transmit images such as photographic images from a source such as a cellular telephone device equipped with a camera to a receiving cellular telephone or other telecommunications device. For example, a doctor may transmit a digital image to another doctor by attaching the image to an email. An x-ray machine located in a remote laboratory may capture an image of a broken bone, and the technician may immediately transmit the image to an orthopedic unit of a hospital for analysis. Cellular telephone devices are now capable of capturing and transmitting moving images, including movies with associated sound, for personal enjoyment.

PCT/US08/71943, filed Aug. 1, 2008, by the same inventor provides considerable detail of wired and wireless remotely controlled ultrasound imaging devices that may be surface-mounted to an animal body and used in combination with an image-guided catheter for minimally invasive medical procedures. FIG. 1 provide exemplary embodiments of a wired or wireless remotely controlled transducer; FIGS. 2-3 provide an exemplary electronic circuit and mechanical diagram, respectively, for a wireless transducer incorporating rotation, linear movement in two directions and twist; and FIG. 7 provides an embodiment combining an image guided transducer for minimally invasive medical procedures with a wireless transducer. U.S. patent application Ser. No. 12/182,247, filed Jul. 30, 2008, of the same inventor provides similar details.

U.S. patent application Ser. No. 11/871,282, filed Oct. 12, 2007, of the same inventor provides details of an image guided ultrasonic catheter and methods of use. FIG. 1 show an image-guided catheter having an anchoring portion 218 slidably mounted to the catheter for fixing the catheter to skin surface of a body. PCT/US07/81185 filed Oct. 12, 2007, of the same inventor provides similar details.

U.S. patent application Ser. No. 11/871,219 filed Oct. 12, 2007, of the same inventor provides details of an anchoring portion of an ultrasound image guided catheter having first and second deployable balloons for positioning the image guided catheter so as to be fixed to an internal body wall such as a pericardial wall for minimally invasive medical procedures.

U.S. patent application Ser. No. 11/782,991, filed Jul. 25, 2007, entitled "Image Guided Catheters and Methods of Use," of the same inventor describes a plurality of embodiments of an image guided catheter that may be used, for example, to image an area of the thoracic cavity such as the heart or other region of interest and deliver medication, treatment and the like accompanied by ultrasonic and other imaging with an ultrasonic array mounted towards a distal end of a catheter. The catheter is provided with a plurality of lumen running from a proximal to the distal end. Interventional, diagnostic or therapeutic devices may be inserted via a sheath to the region of interest.

U.S. Pat. No. 5,465,724, issued Nov. 14, 1995 to Sliwa, Jr. et al. discloses a compact rotationally steerable ultrasound transducer having a circular track or a carrier band operable to rotate a multi-element transducer, for example, for transesophageal echocardiography. U.S. Pat. No. 5,454,373 issued Oct. 3, 1995 to Koger et al. describes a rotatable drive shaft of an ultrasound imaging device having a tubular body and a nose member which includes the ultrasound imaging device and connected to the rotatable drive shaft for rotation to obtain different internal views, for example, of a blood vessel. Alternatively, U.S. Pat. No. 5,701,901 issued Dec. 30, 1997 to Lum et al. discusses a pivotable reflector for reflecting an axially-directed ultrasonic beam in a radial direction per FIG. 5.

U.S. Pat. No. 5,997,497 issued Dec. 7, 1999, to Nita et al. discusses use of a foot petal on/off switch for hands-free actuation of a signal generator connected to an ultrasound transducer. U.S. Pat. No. 7,127,401 issued Oct. 24, 2006 to Miller describes remote control of a medical imaging device using speech recognition as well as foot controls. In particular, a surgeon using an ultrasound imaging console may speak a command, for example, "zoom," and a speech recognition processor receives the voiced command for comparison with a look-up table, and, the functionality being available at an associated control console, magnification of a displayed image may be provided to the surgeon. United States Patent Application, US 2002/0065464, published May 30, 2002, describes an imaging device including a wireless mobile unit. Ultrasonic imaging devices and viewing apparatus are large and bulky apparatus. The described imaging device allows an operator to move freely throughout the operating arena, without being tangled within cords and allowing the patient to remain relatively undisturbed while simultaneously allowing the operator full access to the entire patient's body. United States Patent Application, US 2007/0066894, published Mar. 22, 2007, describes a remote wireless control device for an ultrasound machine and method. The remote wireless control device includes a subset of controls present on larger apparatus including a sonogram display. A smaller mobile unit communicates with the larger unit and may be more easily used bed-side than the larger apparatus.

U.S. Pat. No. 6,558,326 issued May 6, 2003 to Pelissier describes a plurality of ultrasound imaging systems connected to a network according to FIG. 7 which may be a local area network or a wide area network or combination for communicating with a server and a plurality of clients to provide various services such as report generation, tele-exam, remote control, and patient database administration.

Methods and apparatuses for providing three dimensional ultrasonic imaging are known. U.S. Pat. No. 6,572,551 issued Jun. 3, 2003 to Smith et al. describes a three dimensional ultrasound imaging probe configured to be placed inside a body. Published Canadian Patent Application 2 376 103 of Glaser et al. dated Jan. 4, 2002, discusses obtaining three dimensional images by ultrasonic scanning from a minimum of two different positions based on three different send-receive cycles or an arrangement of three acoustic modules and two send-receive cycles, not arranged collinear to each other.

U.S. Pat. No. 7,118,531, issued Oct. 10, 2006, to Krill describes an ingestible medical payload carrying capsule with wireless, e.g. ultrasonic, communication to transducers placed on a patient. The capsule may deliver medication or contain imaging apparatus such as an optical camera and/or a transducer with a pulse driver for internal acoustic pulse illumination and external high resolution sonogram imaging and detection.

U.S. Pat. No. 7,115,092, issued Oct. 3, 2006, to Park et al. describes a micromanipulator useful for ultrasonic imaging systems capable of generating a scanning motion so that front images in various angles can be captured. The micromanipulator can provide up to ±40° of angular deflection, with two degrees-of-freedom, which would provide full 3-D scanning motions. Preferably, the micromanipulator has a tubular structure with at least one compliant mechanism formed from an elastic or superelastic material. These tubular structure can preferably be substituted with pliable needle channel portions or a pre-stressed guide wire introduced through a separate lumen to cause the distal tip to point in a different direction. Such structures are known to be useful in intravascular ultrasound imaging and intervention.

Each of the above-identified patents and patent applications should be deemed to be incorporated by reference herein as to their entire contents.

SUMMARY OF EMBODIMENTS AND ASPECTS

This summary is intended to introduce, in simplified form, a selection of concepts that are further described in the Detailed Description and depicted in the drawings. This summary is not intended to identify key or essential features of the claimed subject matter, nor is it intended to be used as an aid in determining the scope of claimed subject matter. Embodiments and aspects described herein relate generally to embodiments and aspects and methods of use of a wired or wireless transducer element or transducer array that may be remotely controlled to capture multiple image planes at a region of interest of a patient or victim and manipulated or moved to different locations on the skin surface without having to have an operator or large ultrasound system apparatus present at the site of the patient or victim (hereinafter, simply, patient). Such an embodiment may be combined with a wired or wireless image guided catheter at an operating site for insertion into a body for guiding a minimally invasive medical procedure in combination with a surface ultrasound transducer image and, in one embodiment, a further transducer mounted to a catheter or sheath within an outer catheter or sheath for deeper internal body cavity imaging. Moreover, methods of pericardial access are described, for example, employing a vacuum creating tube and/or a grasping device and methods of grasping a pericardial lining. Additionally, the image-guided catheter or sheath may comprise a syringe to drive a needle to a region of interest and thereafter be employed to deliver drugs or evacuate fluid from the region. The needle may be affixed to a further image-guided catheter or sheath. A guide wire may be inserted through a connector channel after disconnecting the syringe, the needle withdrawn leaving the guide wire in the region of interest for threading other devices to the region of interest. Alternatively, after the needle is withdrawn from the region of interest, an outer sheath, for example, of plastic is left in place and a syringe may be used to deliver or remove substances from the region of interest. The patient or victim may be an animal as the embodiments may be used, for, example, in veterinary medicine. Thus, while human patients may be described with respect to various embodiments, the following description and claims are intended to encompass animal species including mammals and, in particular, humans within the term "animal."

In accordance with one embodiment, a transducer array unit or assembly including at least one motor for fixing to a patient's body is wireless (or wired) and communicates imaging data collected by a typically linear ultrasonic array by wireless (or wired) means to a site where collected imaging data is displayed and may be viewed by an operator. One embodiment of a wireless transducer unit is very much like a probe that can be affixed to the body surface and its imaging functions controlled remotely, for example, by wireless radio telecommunication such as WiFi, Wimax, Bluetooth or other radio frequency communication protocol. The wireless communication may also be ultrasonic, infrared or utilize other wireless communication frequencies. Wired communication may be provided via telecommunications including the internet, intranet, twisted pair, optical fiber or coaxial cable or other wired media. For example, pcAnywhere v. 12.1 software, available from Symantec, provides for control of any remote terminal from any other remote terminal and for encrypted two-way communication. The wireless or wired link may be a local or long distance telecommunications link involving satellite transmission. The transducer may be any ultrasound transducer (analog or digital, mechanical, annular, phased array or linear array) and may be single or multi-dimensional. Each transducer array unit, whether remotely controlled or associated with an image guided catheter or sheath, may have its own unique identification code which is communicated with each wireless or telecommunications transmission to a host site of ultrasound imaging processing, control and display. The unique codes of the remotely manipulatable transducer array unit and of an image guided catheter/sheath are used by a host ultrasound imaging remote site to communicate with it. The wireless transducer array unit or image guided catheter or sheath is, for example, battery powered and self-contained such that it may be used by a surgeon without being tethered to a display device by a wire. A wireless transducer or image guided catheter/sheath includes in primary part, ultrasonic transducer circuitry for transmitting and receiving ultrasonic waves, control leads for mode, depth, focus and the like as is known in the art but additionally includes control leads for controlling the movement via one or more motors of the transducer array mounted, for example, on flexible rods of an assembly for movement in two directions, for example, on the skin surface of a patient, transducer rotation or rotation of one transducer about another and the direction of its transmission (transducer twist). The assembly also may include image data transmission and control data reception circuitry. The transducer assembly thus contains a transducer array or element unit that is remotely manipulatable and adapted to be fixed to an animal (for example, human) skin surface or other location and imaging data collected from the device and internally from an associated image guided catheter/sheath.

The image data may be displayed at the remote site as a still image or a moving image (4D) of a three dimensional space which may be stereoscopic. The assembly of this embodiment fixed to the patient's body may comprise an array of transducers or a single transducer element that may be remotely controlled to rotate from one position to another, either clock-wise or counter-clock-wise, to obtain a different planar view of the body part under analysis. The shape of the ultrasound transducer assembly may be round or square or rectangular for providing multi-planar images. The wireless transducer unit may function with a three dimensional imaging system allowing stereotactic observation and remote/robotic operation of devices delivered through or in conjunction with the unit as will be further described below. The transducer array or element may be fixed to a rotor or rotors of one or more motors and the rotor assembly and transceiver circuitry housed within a housing having for example a cylindrical shape with one side intended to be facing the patient's body. The flat side facing the body may have a layer of body impedance matching material complimentary to any gel application. A micromotor and optional associated gear assembly may incrementally rotate the transducer array or element, for example, via the associated rotor and optional gear assembly through a range of 180 degrees or around an image guided catheter/sheath or linearly move the transducer in x or y or both directions or longitudinally along an image guided catheter or sheath. Transducer position may be remotely determined and stored in local or remote memory and/or displayed at the external remote control site. The size of the footprint of a housing for a remotely manipulatable transducer assembly and/or one coupled to an image guided catheter/sheath on a patient's body surface may be as small as 1 cm or as large as several centimeters in diameter (or length/width). A typical operating frequency of the ultrasonic transducer array or element may be between 20 kHz and 400 MHz depending on the clinical application. Different frequency ranges of one or more ultrasound transducers can be used for different purposes and provide different beneficial results. Frequencies in the lower range, for example, below 1 MHz, and particularly in the 100-200 KHz range, can be used, for example, to provide heat therapy or to treat conditions such as blood clots. Frequencies above 1 MHz can be used to provide imaging where the higher the frequency, the greater the resolution possible but the lesser the depth reachable in the human body below the transducer. As indicated above, reception at harmonics of the transmitted ultrasound frequency may improve imaging at depths, for example, in imaging obese animals. Also, smaller structures may be imaged in a range of frequencies up to 200 or 400 MHz. In addition to rotation, a linear transducer array may be adaptably mounted to a rotor shaft so that it may also redirect output sound waves within a range of 180 degrees of twist within the patient's body at the given angle of rotation. A first transducer array or element may cooperate with a second or plurality of similar transducer array units physically attached to or situated inches away from the first array or element as a transmitter or for internal viewing while the second array is for surface viewing. The second device may operate as a receiver for reception of the internal transmitter and vice versa and for three dimensional image, still and motion, capture. The first, second and further transducer array units may separately provide image data of the same region of interest to a remote workstation for three dimensional image capture. The rotatable transducer embodiment may, for example, be of circular, convex, curvilinear, skin surface conforming or cylindrical shape and may be affixed to the body by suture or by a broad securing material that may be elastic, adhesive or non-adhesive, such as a band or bandage of cloth, elastic or other fiber or other securing means. The rotatable embodiment may be coupled to the image guided catheter by a ring for rotation movement about the image-guided catheter. While a surgeon may be present, no ultrasound operator need be attendant at the patient site. Imaging data may be converted from analog to digital format, if necessary, and compressed before it is transmitted in accordance with well known standards to conserve transmission bandwidth to an ultrasound display site. Typical ultrasonic imaging bandwidth requirements should be on the order of 1 MHz especially if known image compression algorithms are utilized at the remotely controlled unit prior to imaging data transmission. If high levels of resolution are required, the data transmission bandwidth may exceed 5 MHz or, if low resolution is permitted, a 100 kHz bandwidth may suffice.

In another alternative embodiment, the transducer array unit may be formed as a square or a rectangle (rather than round) and the linear transducer array in addition to rotation, twist or direction of sound wave transmission may move under remote motor control in a lengthwise or widthwise direction from one end of a square, cylindrical or rectangular shaped housing or one conforming to the shape of a body cavity to the other end. In another embodiment as described above, the array may move in two perpendicular directions, for example, in an x or y axis direction on the body surface and not be permitted to rotate or twist during linear movement. In other words, all motors may be actuated synchronously with other motors or operated independently. Such a device may comprise a single transducer element or a transducer array such as a linear array. On the other hand, a transducer array, for example, contained in a square or rectangular housing may also be rotatable to a predetermined angle of rotation by remote control at each incremental lengthwise or widthwise position and/or twisted. For example, such a transducer array unit may be used to monitor a fetus within a patient as it moves within the abdominal cavity. One unit may be fixed to a female patient's body and be manipulated alone or in conjunction with another or plural remotely manipulatable transducer units affixed to the female patient's body or in conjunction with an image guided catheter for minimally invasive medical procedures such as an amniocentesis. An advantage of utilizing an image guided catheter having an ultrasound image guided needle for penetrating the amniotic cavity is that amniotic fluid may be extracted while a four dimensional image is captured directly of the location of the placenta and fetus thus minimizing risk of damage to either by the needle.

In an alternative embodiment and in conjunction with an imaging catheter as described in my co-pending U.S. patent application Ser. No. 11/782,991, filed Jul. 25, 2007, one or more remotely manipulatable transducer unit assemblies may be used together with the imaging catheter, both of which may be wireless, to provide additional imaging of a minimally invasive heart operation or other procedure being performed on a patient in an operating arena. In deed, visualization of any body part is possible including the heart, liver, kidney, brain, prostrate, vagina, uterus, breast, any vascular structure, gland (such as the thyroid), extremity (knee replacement) or other body part to be monitored. For example, the remotely manipulatable wireless transducer unit may facilitate any intervention requiring ultrasound guidance including but not limited to entry into various body spaces such as a pleural, vaginal, skull, peritoneal and pericardial space thus allowing therapy delivery, intervention, placement of devices such as pacemakers, IUD's or medicine pumps and diagnostics. One skin surface mounted transducer may cooperate with a second body cavity transducer having a linear motor for lengthwise movement along its linear axis, and other motors for rotational movement and twist movement of the transducer. For example, such a transducer may have a cylindrical or other shape conforming to the given cavity and be introduced into the rectum, vagina, nasal cavity, ear cavity, oral cavity or other body cavity or be similar to the known Krill payload that a patient has ingested to obtain further imaging of a region of interest and/or three dimensional imaging. In addition to an imaging catheter, one or more remotely manipulatable wireless transducer array units may be used with an image guided catheter having another interventional, therapeutic or diagnostic system such as a biopsy forceps, a drainage catheter, a pressure monitoring system, a suture application system, a therapy delivery system or other interventional, therapeutic or diagnostic system known in the art.

In yet another embodiment, the remotely manipulatable transducer array unit may deliver ultrasound energy for therapeutic rather than imaging purposes, for example, to specific locations on or under the skin surface or within the body. During an interventional or a therapeutic procedure, the interventional procedure requiring intermittent ultrasound monitoring such as surgery or cardiac catheterization, the transducer element or transducer array assembly can remain on the body during the entire procedure and the imaging and/or therapeutic treatment performed as and when needed by a remote operator or surgeon. The remote operator may communicate with a surgeon or other operating room personnel by telecommunications to, for example, report that a medicine pump has been properly placed and is operating, for example, via a headset worn by the surgeon or other operating room personnel within an operating room.

Known controls of a wireless remotely controlled transducer may include on/off, frequency range, depth of field, focal length, sweep speed, magnification, gain, focus, contrast, brightness, selection of color Doppler imaging versus conventional gray scale, measurement of Doppler velocity and the like may be provided via conventional buttons, knobs or monitor screen controls. An associated display workstation may comprise one or a plurality of displays of the transmitted image of a region of interest including a moving image three dimensional (4D) display or plural displays of multiple planes or a display showing manipulation of the ultrasound transducer element within the boundaries of a housing as placed on a patient or in a patient cavity and/or a display of operating parameters such as the coordinates of location of the transducer, its angle of rotation and its twist or angle of sound transmission. If plural transducer units are utilized, a single workstation may provide additional displays for each remotely controlled and manipulatable transducer unit.

An operating room can only efficiently contain so many people assisting a surgeon and so much equipment. A control operator of a workstation may communicate with the surgeon by means of a headset to answer questions a surgeon or other operating room personnel may have as a yes or no or advise of a successful procedure.

These and other embodiments and aspects will now be described with reference to the drawings and the detailed description to follow.

BRIEF DESCRIPTION OF THE DRAWINGS

FIG. 6) surgical location as one example of an application for minimally invasive heart surgery. Imaging transducer 610 may cooperate with imaging transducer 620 or image guided catheter 100, 630 to provide a three dimensional image of the heart and pericardial cavity and monitor the movement of image guided catheter 100, 630 toward an operating area of the heart or tools for delivery via the image guided catheter 100, 630.

FIG. 8 shows a plurality of different embodiments of the image guided catheter of FIG. 1 wherein FIG. 8C shows the embodiment of FIG. 8B with exemplary dimensions; all embodiments are contemplated to be in wired or wireless communication with one or more operator display consoles (not shown).

FIG. 16 provides longitudinal views of suction and mechanical embodiments for pericardial access; FIG. 16A relates to a suction embodiment; FIG. 16B relates to a mechanical grasping embodiment and shows a guide wire introduced via a needle.

DETAILED DESCRIPTION OF THE EMBODIMENTS

Figure 1A:
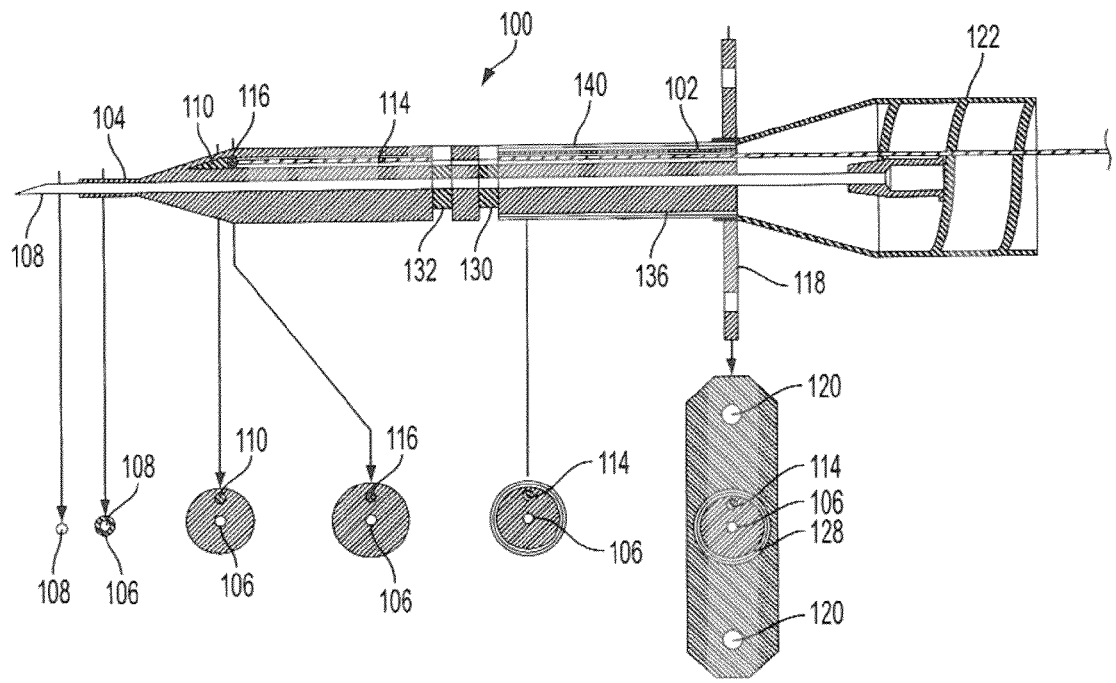
FIG. 1 shows a side cross-sectional view of one embodiment of a minimally invasive device in accordance with aspects described herein wherein FIG. 1A includes six cross-sectional views along the length of the depicted embodiment.
FIG. 1B provides a cross-sectional view of the embodiment of FIG. 1A and FIG. 1C provides further detail of the distal end of the device of FIG. 1A.
referring to FIG. 1D, locations 130 and 132 may show locations for proximate and distal balloons according to an embodiment for introduction of the device through a wall and channels 136, 140 shown in FIGS. 1A and 1B used to inflate the balloons.

FIG. 1 shows a side cross-sectional view of one embodiment of a minimally invasive device in accordance with aspects described herein wherein FIG. 1A includes six cross-sectional views along the length of the depicted embodiment of an image guided catheter 100 for use in minimally invasive medical procedures. Similar reference numbers will be used throughout the detailed description to refer to similar elements wherever possible. One or more lumen 106 provide a path for introduction of a needle 108 which may pass through the lumen 106 to a distal (patient) tip 104 and beyond the distal tip 104, for example, into a body cavity when image guided catheter 100 is introduced from skin surface. Imaging channel or lumen 114 is provided at distal end 104 with a transducer image gathering opening 110, preferably, containing at least one ultrasound transducer 116, for example, comprising a linear array or phased array. Outer wall of balloon channel 136 may be in the form of a sheath. Side apertures (not shown) connected transversely to further longitudinal lumen (not shown) may be connected to ultrasound transducers to provide for imaging an internal body wall such as an organ wall or a pericardial wall between indentations for seal/lock balloons 130, 132 which may be slidably disposed on catheter body 100. Proximal (operator) end 102 may be provided with a slidable anchoring portion 118 having suture holes 120 or other means for securing the anchoring portion to the skin. The anchoring portion 118 may comprise a rubber washer or ring surrounding catheter 100. Alternatively, detents may be provided on the surface of catheter 100 permitting the catheter to be anchored at a longitudinal position on the skin surface with reference to the length of catheter 100.

Figure 7:
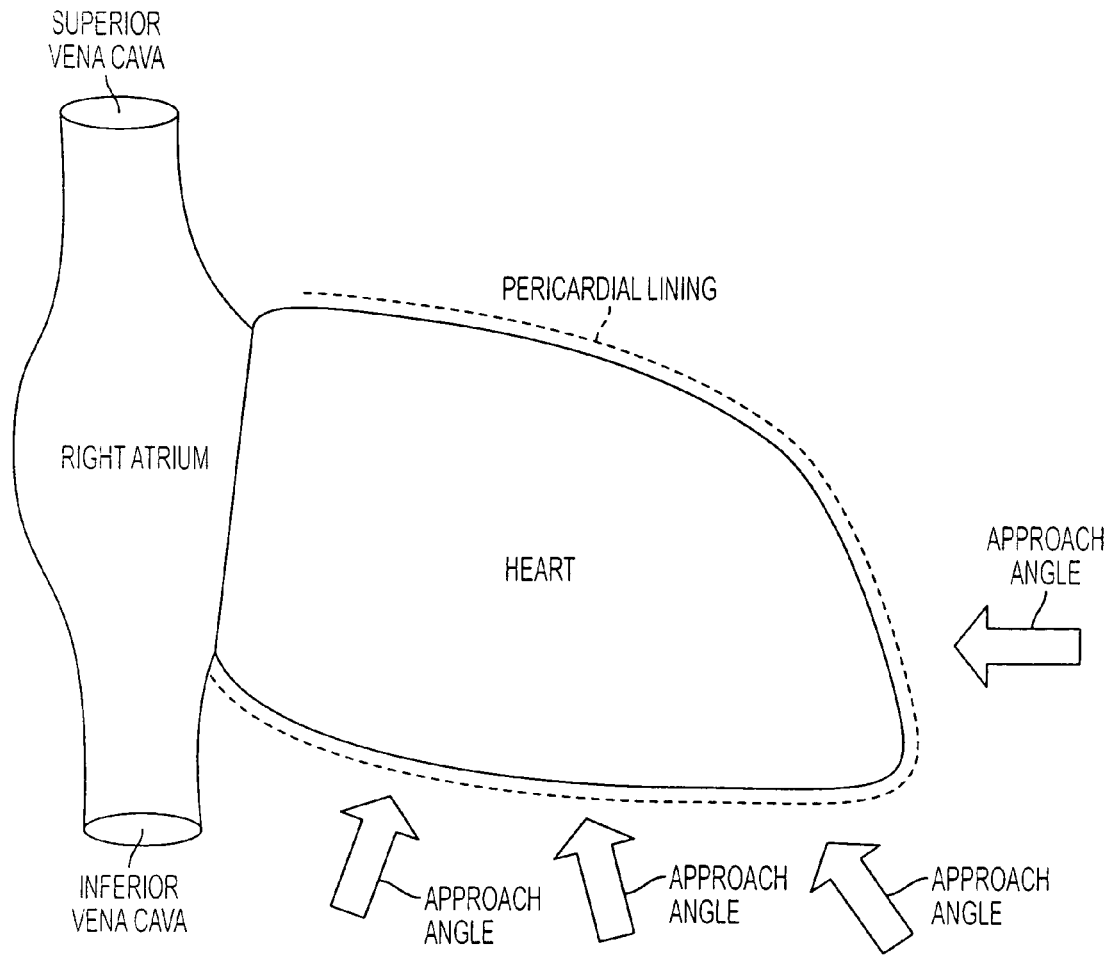
FIG. 7 provides exemplary approaches to the pericardial cavity including pericardial lining and heart.

Prior to anchoring via anchoring portion 118, the catheter may be inserted under vision (herein, ultrasound, optional optic, OCT or other included or external imaging) to a position where distal balloon 132 has reached an inner surface of a body wall. Distal balloon 132 is inflated by saline solution or gas and catheter 100 is pulled to engage the inner surface of a body wall. Then, proximal balloon 130 is inflated to anchor the catheter 100 to the inner wall. Now, anchoring portion 118 may be moved to the skin surface, if not already at skin surface, to further anchor the catheter in place at a body wall such as the pericardial lining (FIG. 7).

In addition, the transducers in the image guided catheter also can be used for intravascular or intra-tubular applications. Thus, imaging guided catheters can include forward viewing catheters for insertion into tubular structures of various sizes such as blood vessels or the fallopian tubes. Forward viewing provides a 3-D scanning motion. Moreover, smaller transducers for imaging within an imaging catheter are preferably useful for insertion into the abdominal cavity, chest cavity, brain matter, spinal cord and component structures, pelvis and ear/nose/throat, etc. Thus, the image guiding catheters can be produced to have a size in microns (μm).

Figure 1B:
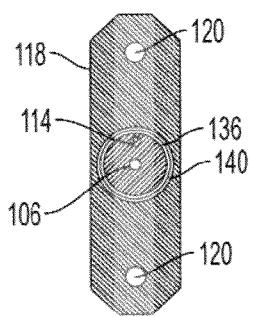
Figure 1C:
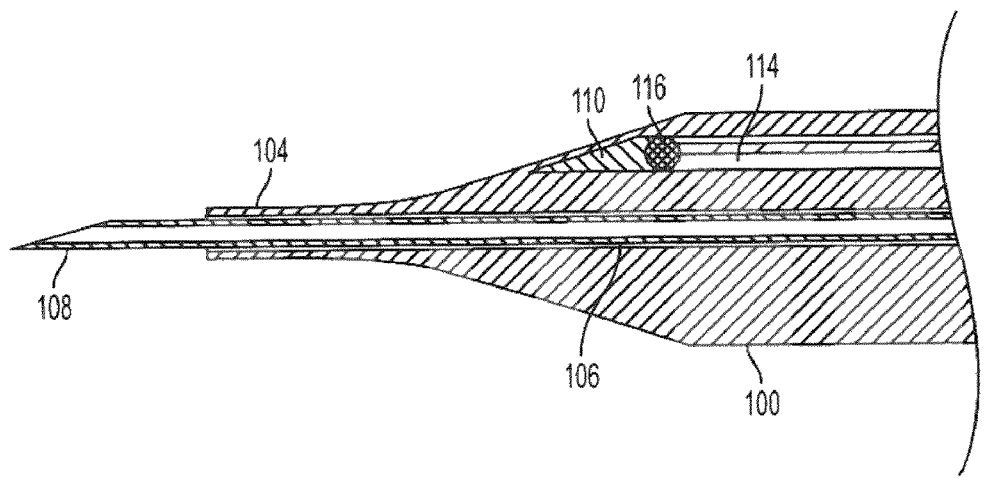
Figure 1D:
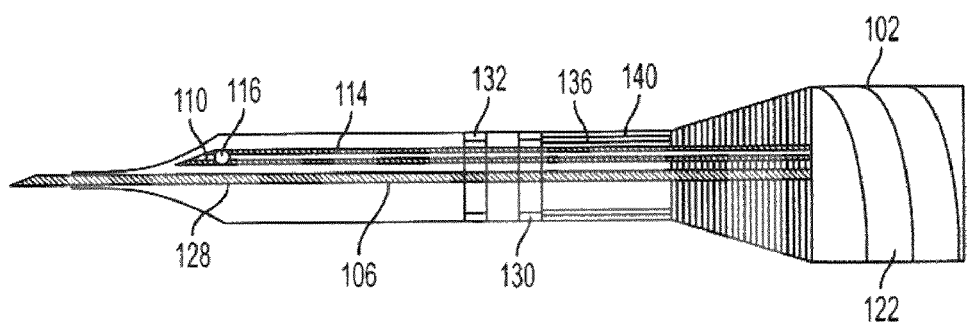

FIG. 1B provides a cross-sectional view of the embodiment of FIG. 1A. Needle lumen 106 is seen along with imaging lumen 114. Channels 136 and 140 provide balloon inflation channels for balloons 132, 130. FIG. 1C provides further detail of the distal end 104 of the catheter device 100 of FIG. 1A. Needle 108 is shown extending beyond distal tip 104 and has an internal channel 106 that may be used for introducing a guide wire or extracting fluid. Transducer 116 is seen within imaging channel 114 having a wire for outputting signal toward the proximal end. Referring to FIG. 1D, locations 130 and 132 may show locations for proximate and distal balloons, respectively, according to an embodiment for introduction of the device through a wall and channels 136, 140 (FIG. 1A, 1B) used to inflate the balloons. Needle assembly 128 will be discussed further herein as useful for introduction of a guide wire and interventional devices via the guide wire or for aspiration or other uses. A valve, luer lock or other cap 122 provides, for example, fluid communication to an attachable syringe (not shown) and prevents leakage of body fluid. Further details of the embodiment of FIG. 1 are provided by U.S. application Ser. No. 11/871,219, filed Oct. 12, 2007, incorporated by reference herein in its entirety.

FIG. 2 comprises a top view (FIG. 2A) and side view (FIG. 2B) of a first plurality of embodiments and aspects of a multi-plane transducer assembly unit 200 comprising a rotatable linear array 202 of transducer elements including a housing adapted for forming a beam of ultrasonic energy and receiving a reflected beam at primary and harmonics of the transmitted frequency. FIG. 2C provides details of rotational and tilt or twist motor movement of a transducer element or array 201, 202 of, for example, piezocomposite or crystal material of housing 203 via motors 316, 322. Vermon of France's US subsidiary, Vermon, USA of Lewistown, Pa., provides piezoelectric composite transducers 201, 202 that may be customized for a particular purpose.

Figure 2A:
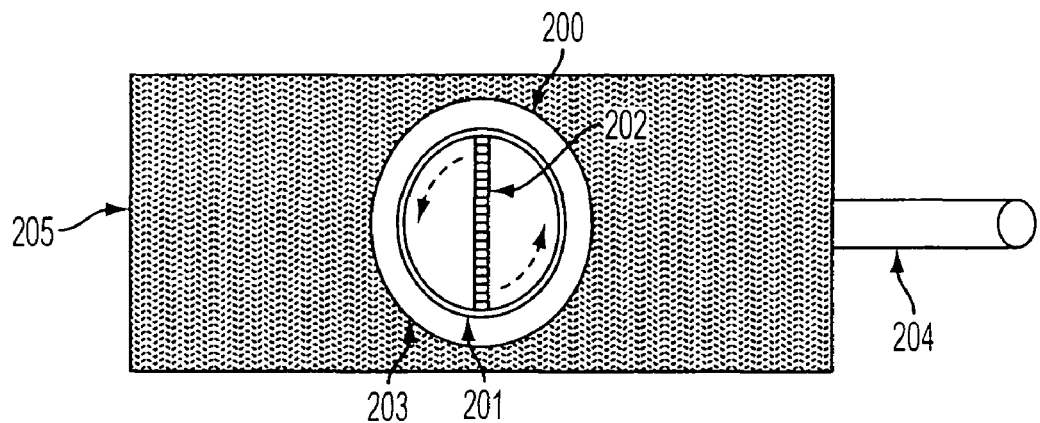
FIG. 2 comprises a top view (FIG. 2A) and side view (FIG. 2B) of a first plurality of embodiments and aspects of a multi-plane transducer assembly unit comprising a rotatable linear array of transducer elements including a housing for mounting by securing material to a body of, for example, a patient or victim, which may be controllably rotated and otherwise controlled by wired or wireless signals remotely from the patient without an operator needing to be proximate to the body to manipulate or control the transducer elements or the housing.
FIG. 2C provides details of rotational and tilt or twist motor movement of a transducer element or array.
FIG. 2D provides further details of rotation and seesaw or tilt/twist movement to capture multiple image planes per panel A (side profile) and B (en face view).
Figure 2B:
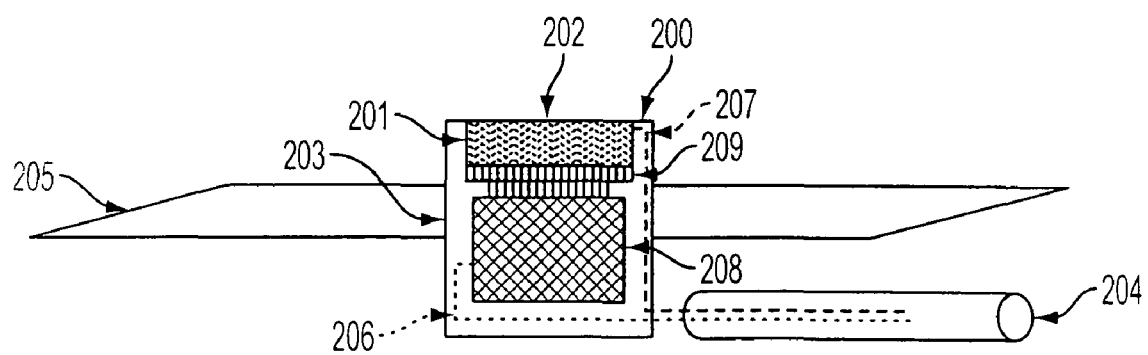
Figure 2C:
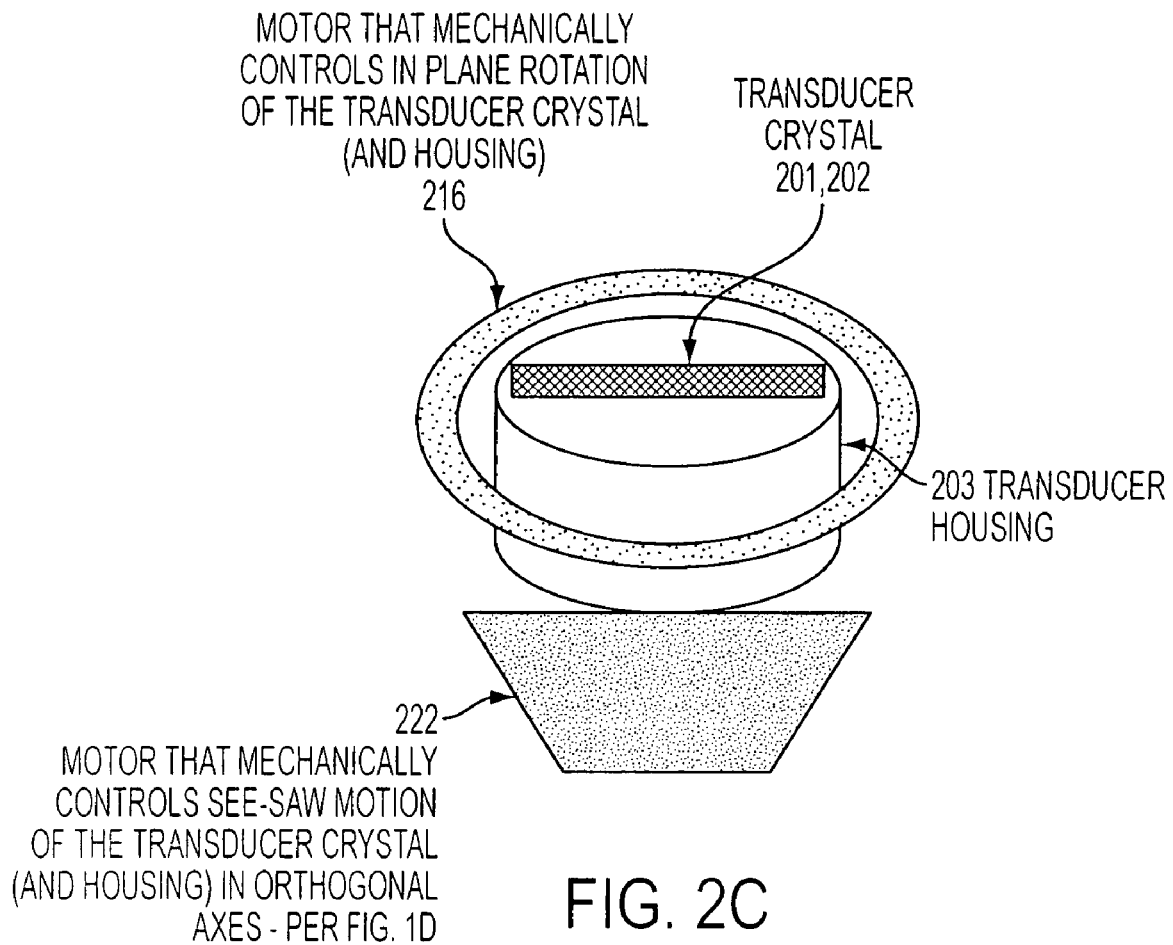
Figure 2D:
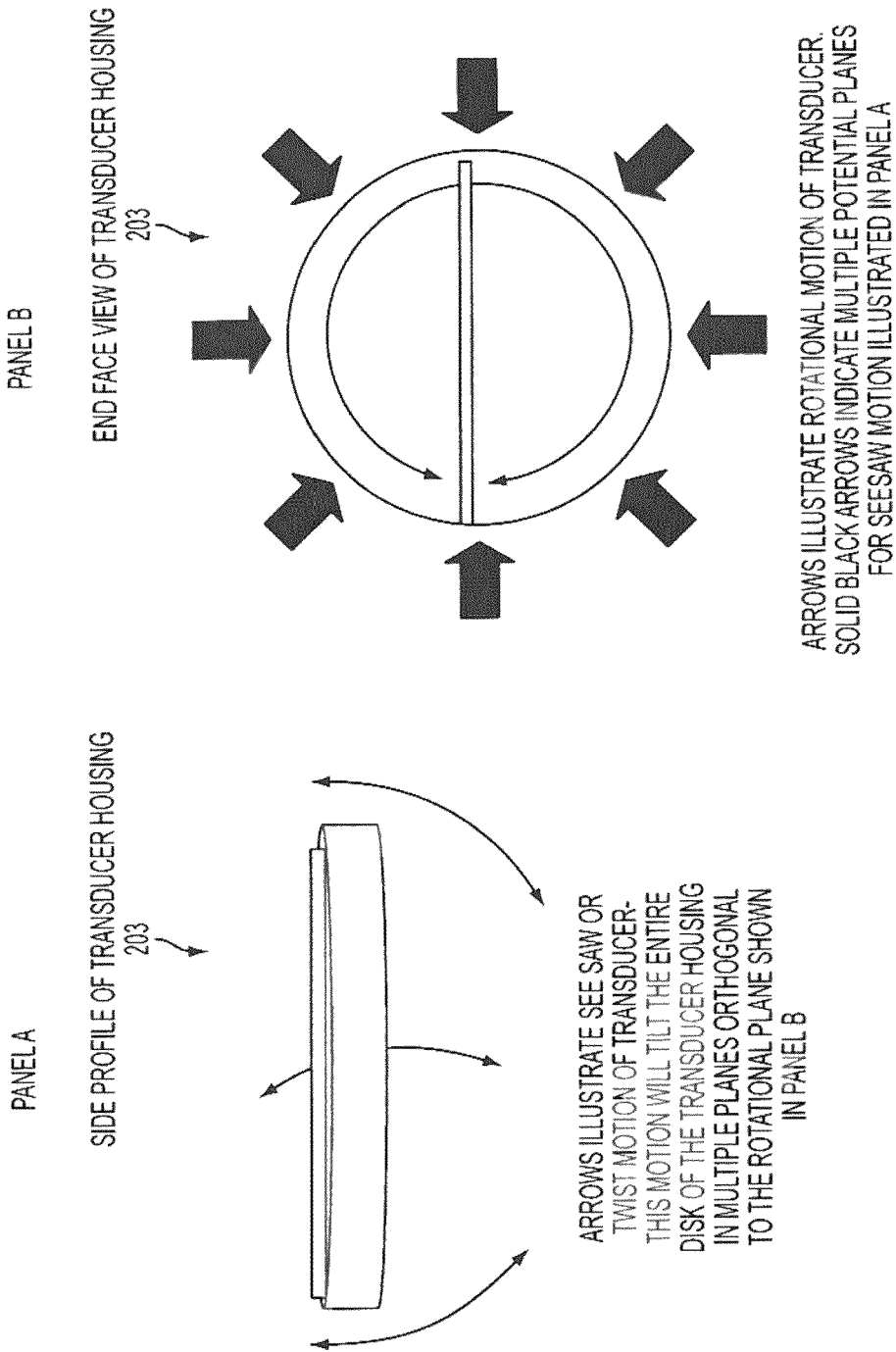

FIG. 2D provides further details of rotation and seesaw or tilt/twist movement to capture multiple image planes per panel A (side profile) and B (en face view) of housing 203. The housing 203 comprising transducer elements 201 and/or 202 may be mounted by securing material 205 to an animal (human) body of, for example, a patient or victim (not shown) or comprise anchoring portion 118. The transducer array or element 201, 202 may be remotely controllably rotated and otherwise remotely controlled by wired (cable 204) or wireless signals transmitted toward the transducer 201 or array 202 from a remote workstation; (see FIG. 14). An ultrasound or other imaging operator need not be proximate the patient's body to manipulate or control the transducer elements 201, 203 or movement of housing 203. Transducer 201 may comprise a single transducer element for ultrasonic transmission and reception of reflected sound waves or, for example, a linear or other shaped array 202 of transducer elements mounted, for example, in a circular manner from a top perspective as a diameter of the circle or at the center of the circle comprising housing 203. An arrow indicates an angle of rotation in a clockwise or counter-clockwise direction of the transducer element 201 or a transducer array 202 within housing 203. Typically, an angle of rotation of 180 degrees when used with a transducer array 202 will permit the collection of a plurality of image planes, for example, of the heart over which the transducer array 202 within housing 203 may be located and fixed to the body surface by a fixing adhesive band or non-adhesive wrap 205, in this case, a preferably cylindrical housing 203 as seen from top and side views forming a circular footprint on the body surface. The shape of the housing can be preferably contoured to any shape for easy insertion into a body cavity. The housing 203 may be fixed to the surface, for example, of a human body, for example, in a position at the center of the chest to monitor the heart immediately below; (see FIG. 6 or 13A). The top surface of the side view shows transducer 201 or transducer array 202 which may rotate within the housing 203. The top surface of housing 203 intended to be fixed to a patient contains an impedance matching substance which may be complimentary to the application of a suitable impedance matching gel. Fastening or securing material 205 is shown in top and side views for fixing the housing 203, for example, to a human body skin surface with the transducer/impedance matching surface facing the human body surface. The securing material 205 may be a band or elastic band that wraps around the body or, in an alternative embodiment, an article of clothing or form part of anchoring portion 118 (FIG. 1). Within the housing 203 is also contained at least one motor, in the embodiment of FIG. 2B, for example, a motor 208 for rotating a transducer element or linear array 202 and/or rotating the array about another array, for example, image-guided catheter/sheath 100. Also located within the housing 203, for example, in the vicinity of the motor may be a wireless transceiver and antenna (not shown; see, for example, FIG. 3), a transducer control unit 210, and other circuitry as necessary for receiving and processing motor control signals and other known control signals such as on/off, mode of operation (such as color Doppler versus conventional gray scale), depth of field, brightness, contrast, focal length, sweep speed, magnification, frequency of operation, focus, focal length, Doppler velocity measurement and the like. Also, not shown is a battery or power system for powering the motors and circuits requiring power. Alternatively to a wireless device, housing 203 may have a control cable or wire 204 for transducer output control, providing power, motor control and the like.

Cable 204 may lead to a workstation console, preferably remote from a patient bedside or to a server communicating with a plurality of workstations and operate in a similar manner to known cables used with devices such as a Toshiba PowerVision™ ultrasound machine, the difference being that the depicted cable 104 further includes a rotation, twist, linear direction or other motor control lead or leads or a data line of such cable further incorporates rotation, direction and twist motor control data in a serial data stream on a single data lead. Alternatively, another manufacturer of ultrasound workstations is Analogic Corporation and, in particular, B-K Medical A/S of Herlev, Denmark. Per FIG. 2B, cable 204 may include at least motor control wiring 206 connected to rotation motor 208 for control and power purposes. Cable 204 may further comprise transducer wiring 207 for power, transducer control and image collection purposes.

Figure 3:
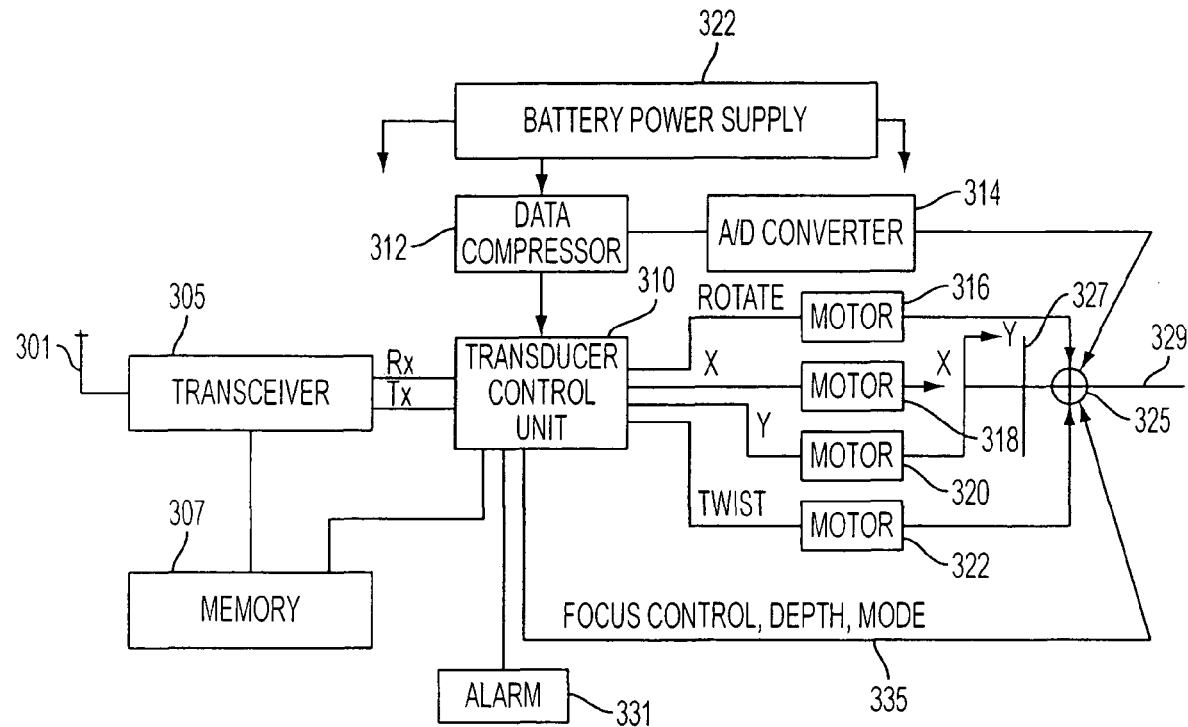
FIG. 3 provides a schematic block diagram for embodiments and aspects of a device as shown in FIG. 2 which may be wireless (or wired) and further including a wireless transceiver in addition to a transducer control unit. Also shown are a battery power supply, one motor for rotating a linear transducer element array, a motor for moving the array in each of perpendicular X and Y directions and a motor for twisting the array, the linear transducer element array and analog to digital circuitry (if necessary) for converting collected image data to digital form and a data compressor for compressing data for digital transmission via the transceiver.
Figure 4:
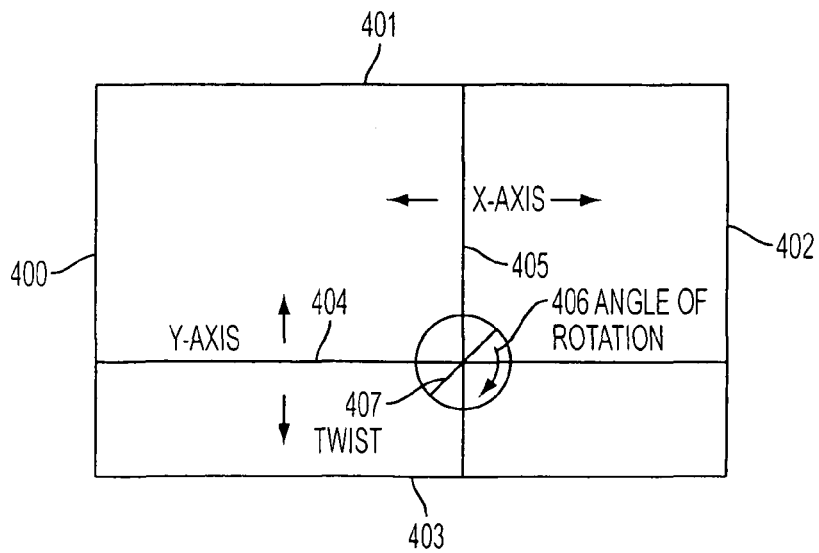
FIG. 4 provides an overview of a mechanical arrangement of, for example, flexible or body shape conforming rods to be contained within a housing of embodiments of a transducer assembly unit for manipulating a transducer or linear transducer array in two perpendicular directions, for example, along an x axis and a y axis, to provide an angle of rotation to permit multiple image planes and a twist angle to redirect a sound wave emitted by a transducer or linear array of transducer elements whereby it is envisioned that a footprint on a patient body surface is rectangular or square and relates to the embodiments and circuits of FIGS. 2 and 3.

As will be described herein and as illustrated by FIG. 2C and FIG. 3, further motors 208 such as motor 322 may be provided for twisting linear array 202 to permit a different direction of sound wave emission and/or reception of reflected sound waves. Still further motors 318, 320 provide two directions, for example, lengthwise and widthwise (x and y) axis movement in the plane of the human body surface and according to how a rectangularly shaped housing 203 constructed of flexible or body surface conforming rods per FIG. 4 is placed on the body, i.e. an x and y axis are considered in relation to the housing 203. The housing 203 may be mounted at an angle or other manner most comfortable for the patient, yet effective. Motor 208 may comprise an optional gear assembly 209 (FIG. 2B) for more accurate, for example, incremental movement of transducer array 202. Motor 208 is preferably a micro or miniature linear motor known in the art for turning a rotor for twisting an array 202 and associated optional gear assembly 209 for rotating the coupled transducer element 201 or linear array 202 at incremental steps such as one degree steps from a vertical or horizontal orientation (vertical shown) through a 180 degree range—clockwise or counterclockwise. In this manner, a linear array 202 may capture up to 180 different planes of view of, for example, a heart under observation, and a moving three dimensional (4D) view may be constructed using known software data analysis processes. Of course, the three dimensional analysis is improved and made stereoscopic if pairs (or more than two arrays) of devices at different observation locations according to FIGS. 1 and 2 are used as will be described in conjunction with a discussion of FIGS. 6, 13 and 14. Referring briefly to FIGS. 13 and 14, the remotely controlled transducer 201, 202 may be rotatably mounted to an image guided catheter 100 or catheter outer sheath 905 via a sleeve or ring 1300 and motors provided for rotational movement about the catheter 100 or sheath 905 and for longitudinal movement.

A transceiver 305 (FIG. 3) or a cable 204 may report the actual rotation position of the transducer array 202 to a remote workstation (not shown) as a value, for example, between 0 and 180 degrees. The physical location of the transducer 325 at a given time may be calculated by detecting a known body part, such as a heart, and from the x, y, depth, rotation, twist, frequency of operation and other control data received at the workstation from the transceiver 305 calculate the physical position of a given housing 203 on the skin surface. In an alternative embodiment, the electronic circuit of FIG. 3 may comprise an input keyboard or selector for selecting one of a plurality of locations on the body, such as chest or abdomen, and/or a target organ, such as one of two lungs or the heart.

Typical sizes for a cylindrical transducer housing 203 as shown in FIG. 1 may be from 1 cm in diameter to 3 cm in diameter. The height of the cylindrical housing may be similar or less than 1.5 cm. The size of a housing 203 is directly related to the components it contains. In embodiments intended to be placed in body cavities, the housing 203 may be sized to conform to the cavity. Certainly, the trend in the electronic arts including mechanical motor arts is toward further miniaturization and integration. Consequently, notwithstanding the given dimensions, it is not inconceivable that a housing 203, for example, may be reduced in height or thickness to the range of millimeters or even micrometers within the next twenty years. The housing may support the movement of an OCT, infrared or other medical imaging device known in the art. The size of the footprint on the human body or whether the device is used internally in a body cavity may relate to the particular application and not necessarily to the sizes suggested above for housing 203.

If a housing 203 has a rectangular shape or footprint which may be concave to fit the surface of a pregnant woman, for example, for observation of a fetus, its shape may be on the order of size of 10 cm by 12 cm, in which case, linear motors are provided for two directions, for example, x and y axis manipulation of the transducer array in these larger dimensions in addition to rotation and twist. Referring briefly to FIG. 4, the surface proximate to the body of a housing 203 may comprise a rectangular shape and linear motors may move small rods carrying, for example, a transducer array to a particular x, y coordinate ranging from 0 to 10 cm in one direction to 0 to 12 cm in the other direction within its footprint on the body surface in incremental steps, for example of 5 mm. In a further embodiment as described above, a motor 322, 407 may be provided and mounted to twist a linear array as well as provide an incremental angle of rotation, again, within a range of 0 to 180 degrees with a default position at 90 degrees, or directly pointing sound waves into the human body; (see FIG. 2C). In an alternative application, for example, to image a human heart, the x and y motors 318 and 320 may be actuated to improve imaging by moving a location of transducer or transducer array 325 to another location removed from a partially obstructed ultrasound path or one including undesired reflections, for example, caused by an implanted device or an invasive device used in the vicinity of the heart region of interest.

FIG. 3 provides a schematic block diagram for embodiments and aspects of a wireless device as shown in FIG. 2 including a transceiver 305 (which may be a wireless telecommunications transceiver), a transducer control unit 310 which may comprise a microcomputer, a battery 322, at least one motor for rotating a transducer element array, for example, a linear array, the transducer element array 325 and analog to digital circuitry 314 (if necessary) for converting collected image data to digital form. There is also provided a data compressor 312 for compressing data for transmission via the transceiver 305 and antenna 301 or cable 204. In one embodiment, the analog to digital converter may be eliminated as data may be collected in digital form from transducer array 325. In FIG. 3, a wireless embodiment of a remotely manipulatable ultrasound transducer is assumed and the wireless circuitry may be equally used in an image guided catheter 100 of FIG. 1 or other image guided catheter embodiments described herein, for example, per FIGS. 8-13 and 16-18. Battery supply unit 322 is preferably a rechargeable lithium battery known in the art that powers all circuits requiring power within a housing 203 (not shown in FIG. 3). Controller 310 has associated program and data storage memory 307 and a clock (not shown) for synchronizing pulsing transducers, image data collection and data transmission to a workstation, for example.

Figure 5A:
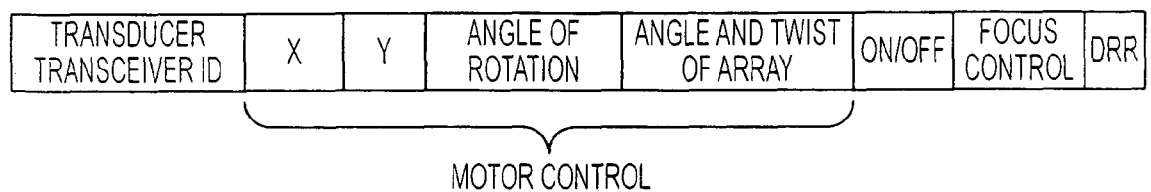
FIG. 5A provides an exemplary signal content format for providing motor control of a remotely manipulatable transducer or transducer array of FIG. 2, 3 or 4 in a direction from a workstation to a remote wired or wireless transducer including a unique transducer transceiver identifier if wireless or telecommunications transmission is utilized. The format also provides for known and herein introduced control such as on/off, focus, focal length, frequency of operation, brightness, contrast, depth of field (related to frequency), sweep speed, contrast, magnification, mode such as selection of color Doppler imaging versus conventional gray scale, measurement of Doppler velocity, time and date and the like. Moreover, image data, for example, recorded in known MPEG, JPEG or AVI format may be transmitted as will be explained with reference to FIG. 5B and subsequently received at the transceiver for verification with transmitted data stored in memory 307.
Figure 5B:
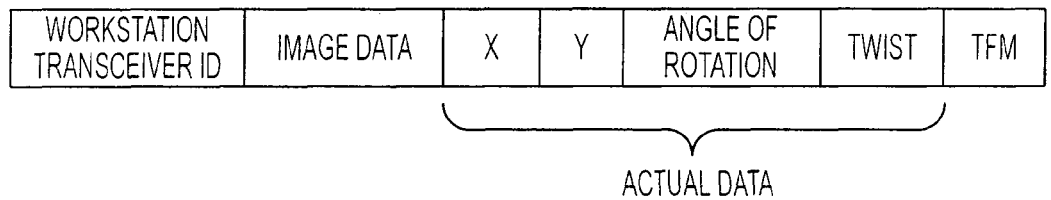
FIG. 5B provides an exemplary signal content format for providing a reply signal from a transducer or transducer array of FIG. 2, 3 or 4 in a direction from a remote wired or wireless transducer including a unique workstation identifier if wireless or telecommunications transmission is utilized toward the workstation or an associated server. The depicted format provides for feedback of actual location data of the position of the transducer or transducer array, time and date of image data (not shown), as well as image data collected for that location and time and date.

Transceiver 305 is an alternative data transceiver to a control and data cable 204 for transmitting and receiving information and may receive and transmit a digital data signal generally in keeping with FIGS. 5A and 5B via antenna 301. While these figures depict what may be construed as a serial data stream, the depicted data may be sent in parallel or serial format and in any order including the order shown. Moreover, the depicted data transmitted in each direction may be supplemented by other known control or imaging data and other unit identification data such as server address data, the server for serving a plurality of workstations. Known telecommunications protocols may be utilized if the transceiver 305 or cable 204 transmits and receives by radio frequency signal such as WiFi, Bluetooth, Wimax and the like for a wireless local area network or optical signal via a dual mode optical fiber 204. Telecommunications cable 204 may be twisted pair, coaxial cable as well as optical fiber and may support POTS, intranet and internet telecommunications as well as other known forms of telecommunications or cable television channel. As is known in the art, infrared and ultrasound may be used as well as other light frequencies than infrared as may transmission in the microwave band. On the other hand, light waves are typically incapable of penetrating through walls and require a line of site transmission path. Yet, by way of example, light wave transmission is feasible; for example, a light wave transceiver connected to a workstation may be mounted, for example, in the ceiling of an operating arena and a unit mounted to a patient facing upward may communicate with the ceiling mounted unit in a line of sight. As described above, since a cable 204 may provide a direct link to a remote workstation or to a server communicating with a remote workstation, cable 204 need not necessarily transmit data uniquely indicative of a given transmitter, transducer, workstation or server because the cable 204 may comprise a direct, switched or multiplexed link or digital channel between known devices. Alternatively, the data of FIGS. 5A and 5B may additionally comprise a unique server address if a server is host to a plurality of client workstations or secondary back-up workstations. Moreover, the workstation ID of FIG. 5B may be a primary workstation, and the data signal further comprise an address for one or more secondary workstations. If any other device is connected to cable 204, then addressing using a unique address (or telephone number) or other identifier should be used for a connected device. Transceiver 305 may receive a data signal from a workstation, demodulate the signal and output a demodulated baseband data signal including data per FIG. 5A to transducer controller 310 which may be a microprocessor, application specific integrated circuit or other control circuit which may be designed and fabricated in a manner well known in the art. Transducer controller 310 may run a real time clock and date program synchronized periodically with a real time clock at an associated workstation. In the other direction of transmission, the transceiver 305 may receive image data for one or more planes or sequential images and other signal including actual position data (for example, x and y coordinates, magnification, depth, rotation angle, twist angle, real time and date and the like) per FIG. 5B from transducer controller 310 for temporary storage in memory 307 or for wired or wireless transmission to a uniquely identified/addressed remote workstation.

Following the path of a received signal at antenna 301, the received signal may be received at radio frequency at transceiver 305 (or via cable 104 at radio frequency, optical frequency or baseband), demodulated, if necessary, and a Rx data output signal passed to controller 310 for processing. Controller 310 authenticates the signal as directed to it by means of the transmitted unique transducer identification code of FIG. 5A. In addition, the signal may require processing in accordance with well known protocols for decompression, decryption, parity and other data error detection and correction algorithms and the like (not shown). In one embodiment, for example, for multi-planar imaging purposes, the transducer array 325 is linear and may be rotated. A rotate signal which may indicate an angle between 0 and 180 degrees in incremental steps of, for example, one to five degrees can indicate rotation in a clockwise or counterclockwise direction or indicate an angle to which the transducer array or element is to be rotated (for example, from 90 degrees, actual present position, to 120 degrees, desired position) is received and passed to linear rotation motor 316 having a rotor for rotation using, possibly, an optional gear assembly 209 for turning the linear array 202 to a desired angle of rotation. In FIG. 13, a rotation motor 316 at location 1360 may rotate a surface mounted transducer around an image guided catheter or sheath 905 through an angle of 0° to 36020. A current position of the transducer 325 may be stored in memory 307 as actual motor control data per FIG. 5B for association with image and TFM data as will be described further herein.

In an alternative embodiment, for example, for therapeutic purposes, a direction of sound wave propagation, frequency of transducer operation (if variable), depth (dependent on frequency) and the like signal are received and reported to actuate twist motor 322 to a desired angle of twist in addition to a desired angle of rotation via motor 316 to, for example, deliver a therapeutic sound wave to a given body organ or sub-tissue layer at a given transmitted depth, for example, represented by a sound wave power level, within the patient's body from the transducer 202, 325 and temporarily stored in memory 307. In an embodiment paired with another unit, the angle of twist and rotation may be synchronized so that one transducer array 202 may cooperate with another transducer array as sound wave transmitter and sound wave receiver for together providing image data either individually or together. Also, a therapeutic transducer (operating at a lower ultrasound frequency range) and an imaging transducer (operating within a higher ultrasound frequency range) may be mounted to the same movement system 400 per FIG. 4 within the same or different housings 203.

In a further alternative embodiment, the transducer array 202 or transducer element may be manipulated in two directions, perpendicular to one another, along the patient's body surface, denoted an x direction and a perpendicular y direction or axis as shown in FIG. 4. If used inside a body cavity such as a nasal, oral, ear or other body cavity, a cylindrically shaped housing may contain a transducer which may rotate 360°, twist 180° and be moved by separate motors along the length of the cylindrical housing 203 shaped for the cavity to different lengthwise, axial positions to capture any number of side views in practically any direction of ultrasound propagation. Beamforming may be additionally used to form ultrasonic waves for a particular purpose. For example, a transducer positioned in the ear may obtain imaging of the brain, inner ear, nasal passages and other portions of the skull depending on frequency range and transducer pulsing delay as known in the art or to apply therapeutic treatment. In the oral cavity, for example, one may ask the patient to attach or hold a flexible patch with their tongue a transducer assembly with x, y, twist and rotation made of flexible rods 400-405 per FIG. 4 conforming to the roof of the mouth. The transceiver 305 outputs such transducer control data to controller 310 which then actuates motors 318 for x axis movement and 320 for y axis movement, 316 for rotation and 322 for twist of transducer element or transducer array 102, 325 as shown in FIG. 4. Also shown in FIG. 3 are x, y axis 327, 329 which are controlled by motors 318, 320 corresponding to x and y axis 405, 404 of FIG. 4. When arriving at the x, y position of interest, the transducer 202, 325 may be rotated or twisted or rotation and/or twisting/rotation may occur en route to the x, y position of interest. Feedback to the remote workstation may be provided via actual data stored in memory 307 indicating all parameter values of interest, on/off, focus level, depth, magnification, ultrasound frequency, x axis, y axis, angle of rotation and angle of twist (most of which are shown in FIGS. 5A and 5B) as well as image data and workstation address or identification.

Also, controller 310 may be in receipt of motor control, off/on, focus control, mode, magnification, frequency of operation, depth and other control data which is passed to transducer 202, 325 for proper operation, for example, to regulate the amount of power delivered to transducers for sound wave emission or for focusing the array. This control lead or collection of leads is shown as data line or bus 335. If more than one transducer is provided for, for example, simultaneous imaging and therapeutic purposes, then, a selection bit for selecting one or the other transducer or array 325 may be included in the data of FIG. 5A.

The output of transducer array 202, 325 may be raw image (reflected sound wave) data similar to that obtained by a hand-held transducer array known in the art. It may be in analog form and provided to an A/D converter 314 (optional) for sampling at an appropriate sampling level, for example, depending on desired image resolution or in digital form. The data signal output of A/D converter 314 (optional) may be further compressed at data compressor 312 prior to formatting at controller 310 for transmission at transceiver 305 and/or storage at memory 307, for example, according to FIG. 5B. These circuits 314 and 312 are shown as separate circuits but may, together with controller 310 be in the form of a single application specific integrated circuit (ASIC) or provided as separate circuits. Memory 307 may be on board a microprocessor chip or provided separately. In one embodiment, memory 307 may comprise a removable memory for uploading, for example, imaging, actual position and TFM data collected over time to a device for telecommunications transmission. The image and other data prior to transmission or for long term storage may be temporarily or more permanently stored in memory 307. Similarly, memory 307 may be utilized for temporarily storing control data as received from transceiver 305 and prior to being operated on by controller 310. In one embodiment, there may be no data transmission via cable or wireless means; data may be transferred, for example, via a removable memory 307.

Image and associated position data and the like for a given image along with time of day and date may be stored in a fanny pack or personal remote control device worn or otherwise carried by the patient. This assumes a time of day and date clock associated with controller 310 or the time and day may be periodically updated via a transmission to the unit of FIG. 3. In, for example, a therapeutic embodiment of a remotely manipulatable transducer array, the patient wearing or carrying one or more assemblies may control delivery of therapeutic sound waves via a transducer array 202 and control the direction and depth of transmission. For example, ultrasound has been found to assist in relieving arthritis and other pain, for example, in a hip, shoulder, knee or other joint.

In one embodiment where the circuitry and motors are contained in a housing and in accordance with FIGS. 2, 3, 4 and 5, the housing is worn by a person, the person may be remotely observed as they go about their daily routine. With improved flexibility of materials over time, even an internal image guided catheter or sheath may be worn by a person similar to an embodiment of FIGS. 1, 8-13 and 16-18. For example, a remotely manipulatable ultrasound transducer array 202, 325 located so as to monitor a major organ may detect a change that requires medical attention. In such an instance, alarm 331 may comprise a vibrator or display or other alarm device to signal the wearer to report to a facility. The alarm may also indicate a point in time when a memory 307 is full of un-transmitted images, and the wearer must change their memory card of memory 307 or report to a workstation or other telecommunications facility for image data upload.

In a further embodiment according to FIG. 3, there may be provided a wired remote control for use by a wearer to apply therapeutic ultrasound energy and so control rotation, x and y axis and twist motors 316, 318, 320, 322 and control ultrasonic frequency range of transducer 201, 202, 325 to deliver therapeutic treatment, for example, in the event that a workstation operator is out of wireless contact with the wearer or the wearer has been pre-instructed as to a particular therapeutic treatment that may correct a given complication. A priority of control of an assembly according to FIGS. 1-5, 8-13 and 16-18 may be surgeon, primary workstation operator, secondary work station operator and wearer from highest to lowest priority control. Ultrasound waves (as well as OCT and collected infrared) are for the most part harmless. On the other hand, a user may be provided only limited control over, for example, frequency and intensity of any emitted pulsed or continuous wave while a surgeon will have unlimited control especially in emergency intervention situations.

FIG. 4 provides an overview of a mechanical arrangement to be contained within a housing 203 of rectangular or square embodiments of a transducer assembly for manipulating a transducer or linear transducer array 325 in two directions, for example, along an x axis 403 and a y axis 404 and to provide an angle of rotation 406 and a twist angle 407 at a desired x, y coordinate pair to redirect a pulsed or continuous sound wave emitted by a transducer or linear or phased array 325 of transducer elements whereby it is envisioned that a footprint on a patient body surface is rectangular or square and relates to the embodiments and circuits of FIGS. 2 and 3. Assume the rectangle housing 203 comprises guide wires or rods 400, 401, 402 and 403 which may be flexible or body surface conforming on which are provided y-axis rod 404 which may be moved in an up and down direction shown via a corresponding motor 320 and gear assembly not shown to incremental steps along the y axis 404. Similarly, there is provided x-axis rod 405 which may be moved to the left or the right direction shown via corresponding motor 318 and a gear assembly not shown. X-axis rod 405 and Y-axis rod 404 intersect at a desired point where an array or element 325 may be affixed via further rotation and twist motors 316, 322. For example, rotor 306 of motor 316 (in combination with an optional gear assembly 109) provides rotation of a mounted transducer array 102, 325 or transducer element to a predetermined or desired angle of rotation. Motor 322 provides twist 407 to linear or other array 325 or element 202 to change direction of sound wave transmission or reception with 90 degrees—straight down—being a default position for twist.

FIG. 5A provides an exemplary signal content format for providing motor control of a transducer or transducer array 202, 325 of FIGS. 2, 3, 4 and/or 13 in a direction from a workstation to a remote wired or wireless transducer assembly including a unique transducer transceiver identifier if wireless transmission is utilized. The format also provides for known control such as on/off, focus, depth, mode and the like. According to various embodiments, motor control data may comprise an x direction or a longitudinal axis direction, a perpendicular to x or y direction, an angle of rotation, an angle for twist of a transducer or array 325 as depicted. There is also a DRR field that my be used for all other control mentioned herein including but not limited to: magnification, depth, frequency range, time of day and data (as needed), periodicity of imaging, transducer select data for a selected one from a group or for selecting a group from a larger plurality of transducers, an indicator of a controlling workstation or user or other control indicator that may be included in this field. Other control or other data to be transmitted in a direction from workstation or other user towards an identified transducer assembly may come to mind of one of ordinary skill in the art of ultrasound apparatus. Motor control data may be transmitted, for example, in the form of ultimate desired position or as an incremental step from an actual position or other way that may come to mind of one of skill in the art.

FIG. 5B provides an exemplary signal content format for providing a reply signal from a transducer or transducer array of FIG. 2, 3, 4 or 13 in a direction from a remote wired or wireless transducer including a unique workstation identifier if wireless transmission is utilized. The wireless transmission may be directed via a server and a server identification provided (for example, of TFM field)) serving one of a plurality of workstations identified by workstation identifier. The format provides for feedback of actual location data of the position of the transducer or transducer array and image data which is preferably compressed. The actual location data may comprise an x axis or longitudinal axis dimension, a perpendicular y axis dimension, an angle of rotation, an angle of twist as well as compressed image data. There may be a TFM indicator field useful for all other control mentioned hereinafter including, for example, the identity of the transducer or transducer array associated with the image data and a time and date indicator provided by the real time clock program of the transducer control unit for the time and date of collection of the image. In an embodiment including a therapeutic transducer, the frequency of operation and the level or magnitude of transmission and a measure of the reflected wave and/or its harmonic may be signaled as well as a data indicator of an image of the region of interest, for example, a blood clot. The actual location data may be compared to a desired location to determine if the remotely manipulatable transducer or transducer array has reached a desired position so that imaging may begin. Moreover, the imaging and control data may be collectively utilized by a workstation to determine the location of one of the transducer assemblies of, for example, FIG. 2, 3, 4 or 13, for example, on the skin surface, in the vicinity of a region of interest as introduced from the skin surface or within a body cavity.

Figure 6:
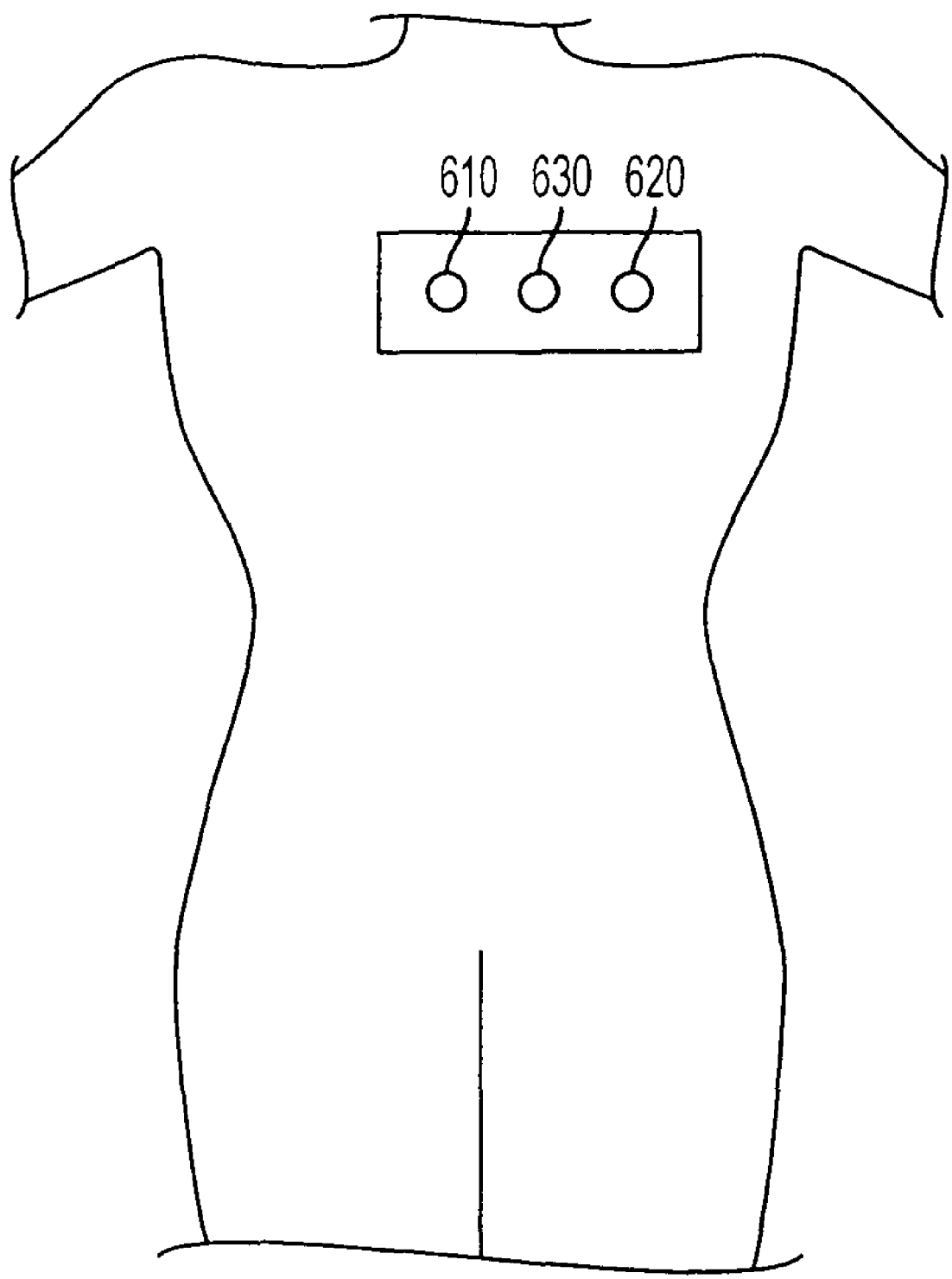
FIG. 6 provides a suggested location on a human body for locating a remotely manipulatable transducer or transducer array assembly whereby the assemblies may comprise devices and elastic or adhesive material similar materials used for fixing electrodes used in electrocardiography, banded adhesive attachment or bandage or banding of the manipulatable transducer or transducer array housing to a human patient's body for integral use with an image guided catheter which may be wireless (or wired). First and second manipulatable transducer units 610, 620 may be mounted to either side of, for example, an image guided catheter 100, 630 (FIG. 1.

FIG. 6 provides three transducers 610, 620, 630. FIG. 6 may provide imaging during a heart operation. In particular, FIG. 6 shows an arrangement for pericardial activity and possibly surgery including first and second remotely manipulatable transducer assemblies, 610, 620 mounted to either side of, for example, an image guided catheter 630 surgical location as one example of an application for minimally invasive heart surgery. Image-guided catheter 630 is guided by its ultrasound transducer at its distal tip to a region of interest with the assistance of ultrasound imaging from the surface captured by assemblies 610, 620. The subsequently described embodiment of FIG. 13 may provide, for example, up to four remotely manipulatable transducer assemblies surrounding an image guided catheter 630, 905 via ring 1300. The image guided catheter 630 may be one as shown and described in FIG. 1 or FIG. 8-13 or FIG. 16-18 or per my co-pending U.S. patent application Ser. No. 11/782,991, filed Jul. 25, 2007, entitled "Image Guided Catheters and Methods of Use," of the same inventor, for example, per FIG. 1 of that application, my published PCT application WO2008/046031, U.S. patent application Ser. Nos. 11/871,219 and 11/871,282 filed Oct. 12, 2007, all incorporated herein by reference as to their entire contents. Methods of use include, for example, double balloon heart wall processes, amniocentesis, body cavity drainage and the like wherein the wireless arrays 610, 630 may image successful deployment of the image guided catheter and intervention, and therapeutic or diagnostic apparatus in the region of interest, for example, of the heart (lung or other organ requiring treatment). Elements or transducer arrays 610, 620, 630 may cooperate to provide stereoscopic as well as multi-planar imaging while the image-guided catheter 630 contains its own ultrasonic array for imaging a point of intervention, therapeutic or diagnostic care. A single workstation may receive imaging and control signal data as described in the context of FIG. 5B from each of transducer array assemblies 610, 620 and 630 or additional remotely controlled wired or wireless arrays.

A workstation for use with such an arrangement shown in FIG. 6 may comprise a plurality of screens to show all images obtained from each of ultrasound transducer elements or arrays 610, 620 and 630 or visual images, for example, obtained via a camera and optic bundle for visual imaging from a distal end of a catheter/sheath 100. See, for example, FIG. 14. An operator remote from the operating suite may, for example, remotely manipulate and control arrays 610, 620 and obtain imaging therefrom while the surgeon may receive imaging data from imaging catheter 630 on a surgical room display. The workstation operator may communicate with a surgeon by a wireless telecommunications device worn, for example, as a headset by each of the surgeon (or other operating room personnel) and the workstation operator. The transducers/array assemblies 610, 620 including motors may be remotely manipulated on the patient within a region of interest from the workstation and remain on the patient during the entire operation. The imaging can occur when and as requested by the surgeon of the workstation operator. Also, transducers/array assemblies 610, 620 may comprise transducers for therapeutic purposes, for example, for dissolving a blood clot and so be controlled by the surgeon or the workstation operator for that purpose (with the surgeon having the ultimate control). Uses may comprise, for example, but not be limited to pericardiocentesis, vascular surgery, coronary angioplasty, valvuloplasty, alcohol septal ablation, delivery of drugs, stem cells or laser therapy, valve repair or replacement, cardiac shape modifying devices such as ACORN-like or MYOSPLINT™, myocardial scar reconstruction, ventricular reconstruction and ventricular assist device placement. One may monitor the blood flow of any vessel to and from the heart or carotid blood flow during cranial or other surgery via a Doppler effect ultrasound transducer. Besides the image guided catheter 630, other devices usable with a remotely manipulatable transducer or transducer array assembly 610, 620 include a biopsy forceps, a drainage catheter, a pressure monitoring system, a suture application system, a therapy delivery catheter or system or other intervention system. Note that a plurality of displays may be provided at a primary workstation for providing multiple views, stereoscopic views and the like obtainable from all three transducers or array assemblies 610, 620, 630 of FIG. 6 or other transducers or imaging devices not shown. Also, there is typically inadequate space in an operating room for an ultrasound operator, for example, next to a surgical operating table. The operator or surgeon may place the transducer assemblies 610, 620 and then remotely manipulate and control and view images from the remotely manipulatable transducer assemblies or apply therapeutic treatment. Their workstation can be located in a corner of the operating room or outside the operating room and the operator communicate by telecommunications means with the surgeon (or other operating room personnel). Further details of a remotely controlled wireless transducer are provided, for example, in PCT Application US08/71943 filed Aug. 1, 2008, incorporated herein by reference in its entirety.

FIG. 7 provides a plurality of approach angles to a pericardial space including a pericardial lining. As will be further described with respect to subsequent figures and embodiments and methods of pericardial access, the approach angle may dictate the placement of a combination of transducer assemblies as suggested by FIG. 6 or 13. The patient may be rolled on the side or on their back but approach through the chest cavity may be most appropriate depending on the region or interest or target zone of interventional or therapeutic therapy.

Figure 8A:
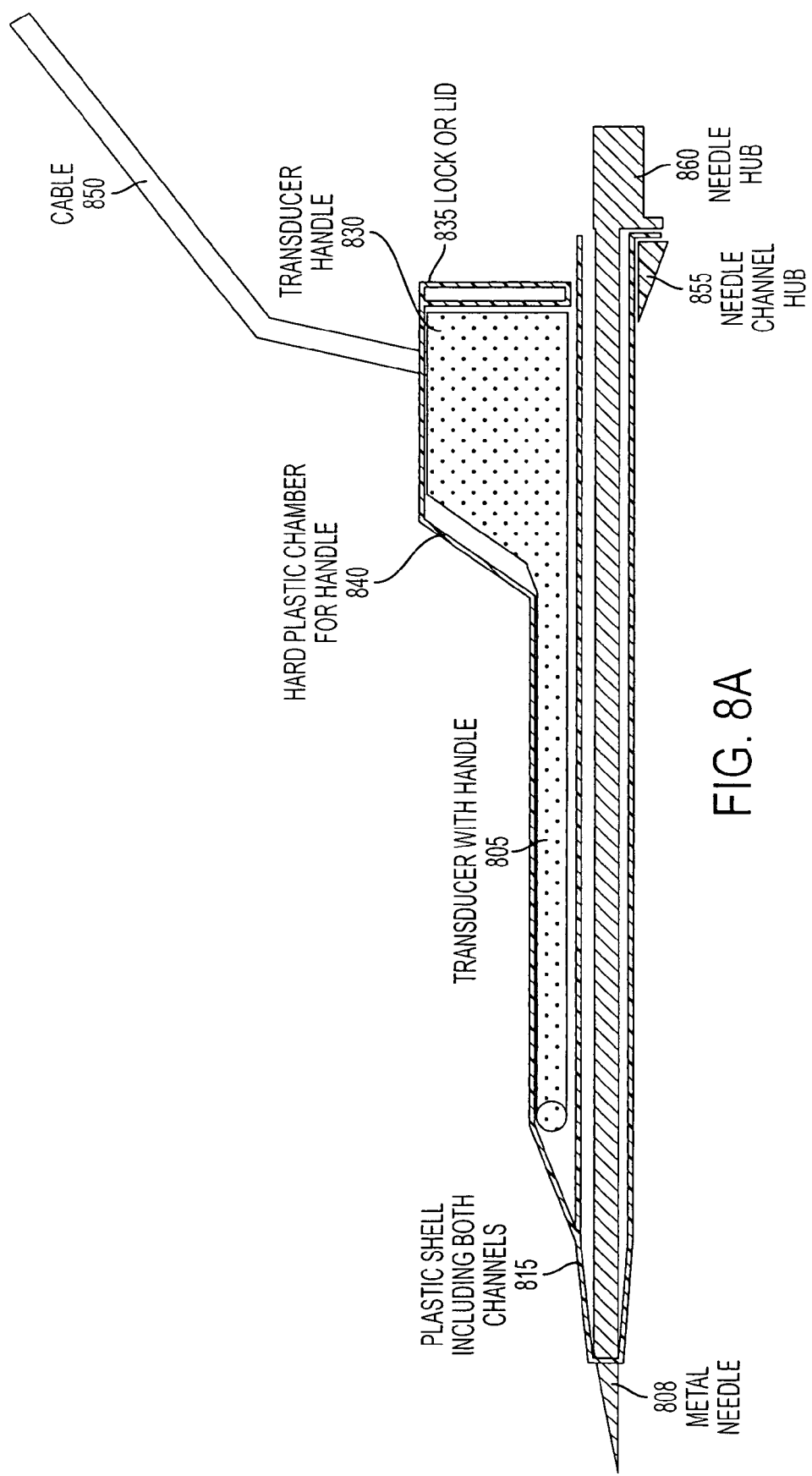
FIG. 8A shows an embodiment having a handle and is preferably cordless (although a cord is shown) and employ wireless transmission per FIGS. 3 and 5.

FIG. 8 shows a plurality of different embodiments of the image guided catheter of FIG. 1. Referring first to FIG. 8A, there is shown an embodiment having a handle 830 and is preferably cordless (although a cord 850 is shown) and employs wireless transmission per FIGS. 3 and 5. The circuitry of FIG. 3 may be easily contained within chamber 840 for handle 830 and connectors provided for receiving input from removable transducer 805. Lock or lid 835 opens to permit a replacement transducer 805 to be placed in an imaging channel which may be one of at least two channels, the second being, for example, for a needle 808, for example, of metal. Needle 808 has a hub 860 and is insertable up to needle channel hub 855.

Figure 8B:
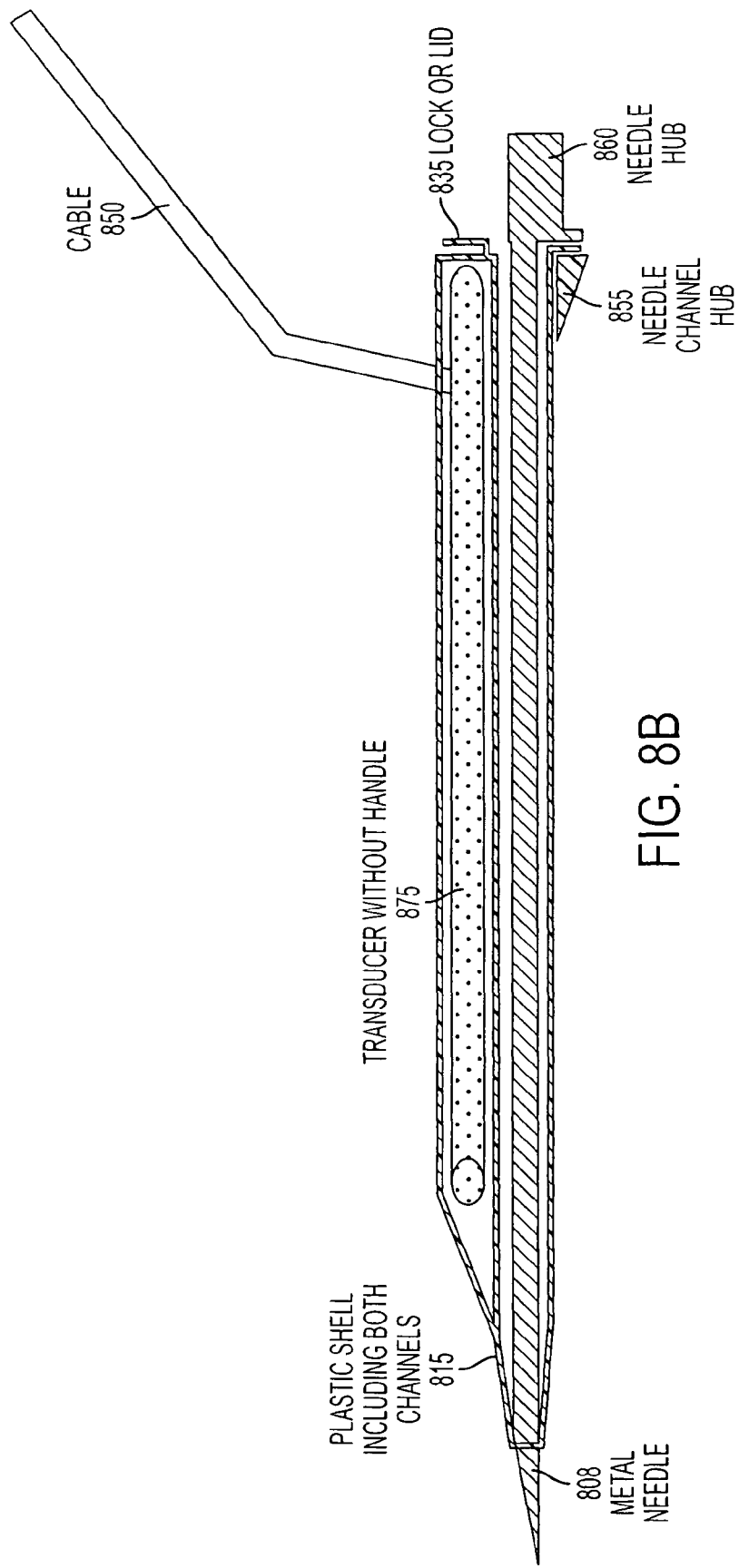
FIG. 8B shows an embodiment having no handle of an image guided catheter.

FIG. 8B shows an embodiment having no handle of an image guided catheter. As in FIG. 8A, cable 850 is unnecessary and the device may be wireless. The wireless circuitry may be housed in the vicinity of the connection of cable 850 to am imaging channel for replaceable transducer 875. As in FIG. 8A, the shell of FIG. 8B may be of plastic and comprise at least two channels or lumen, one for imaging and the other for needle 808 which may be metal. Needle hub of needle 808 is insertable up to needle channel 855 which stops its further progress. FIG. 8C shows the embodiment of FIG. 8B with exemplary dimensions for pericardial access through the chest, breastplate area. The metal needle 808 may comprise a metal of, for example, 14 gauge or 16 gauge. The length of the corded or wireless imaging or intervention channel may be 5.0 centimeters. The channel may accommodate an interventional instrument or replaceable transducer having approximately a four millimeter diameter. The thickness of the channel may vary but may be on the order of 0.07 centimeters. The overall length of the catheter from needle channel hub 855 at the proximal end to the distal end, excluding a protruding needle 808 may be, for example, 6.0 to 6.25 centimeters. The needle 808 may be 0.3 to 0.4 cm longer than its corresponding introducer channel. The catheter or sheath ideally should be composed of biocompatible material that has a short term, transient or non-indwelling use of minutes to, for example, one month. The thickness of the needle introducer channel may vary but may be on the order of 0.05 centimeters. Such a device may be utilized, for example, for pericardial access. All embodiments are contemplated to be in wired or wireless communication with one or more operator display consoles (not shown). See FIG. 14.

Figure 9:
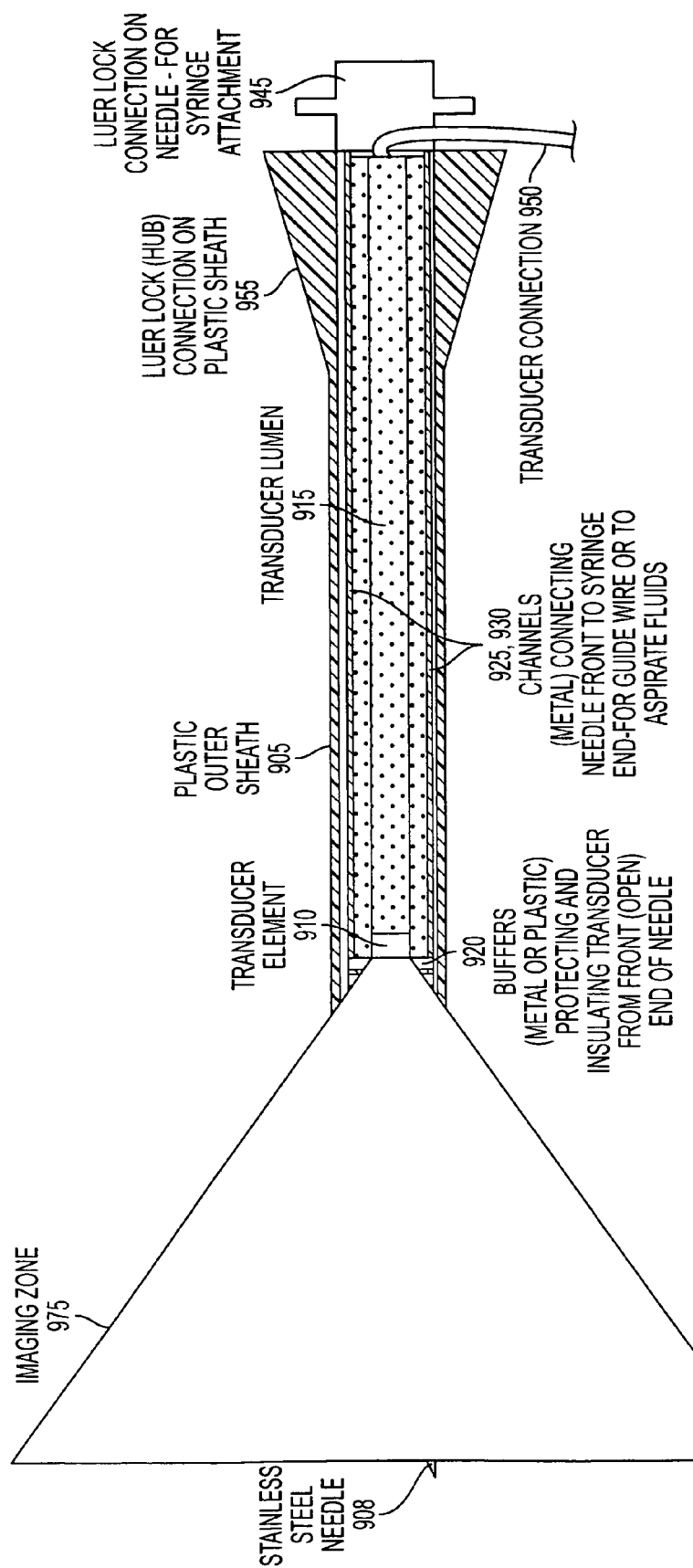
FIG. 9 provides an alternative embodiment of the image guided catheter apparatus of FIG. 1 having an outer sheath whereby a transducer lumen may be used for image guidance and then the transducer replaced, once a region of interest is reached, with another transducer or interventional devices, the embodiment further comprising a needle channel, needle buffers and further channels for guide wires or aspiration, the proximal end including a luer lock for attaching a syringe.

FIG. 9 provides a further exemplary embodiment 900 of the image guided catheter apparatus 100 of FIG. 1 having an outer sheath 905 whereby a transducer lumen 915 may be used for image guidance and then the transducer 910 replaced, once a region of interest is reached, with another transducer or interventional devices. The embodiment further comprises a needle channel for a stainless steel needle assembly 908. The assembly include needle buffers 920 and further channels such as channels 925, 930 for guide wires or aspiration, the proximal end including a luer lock 945 for attaching a syringe. Transducer 910 comprises a replaceable transducer for removal via channel 915 shown in cross-section in FIG. 10(6). Transducer 910 is for providing internal imaging zone 975, forward-directed. Other lumen may be transverse and provide side imaging for, for example, locating a pericardial lining and deploying balloons on either side to anchor the sheath 905. Anchoring systems are not shown for clarity in FIG. 9. Transducer connection 950 may be wired or wireless and circuitry housed for wireless transmission/reception at the proximal end in hub 955. As further described herein, a luer lock 945 may provide fluid communication with a syringe, not shown.

In an exemplary embodiment per FIG. 10, catheter 900 can consist of two portions, split, for example, at 920(1), one portion towards a distal end of the device and the other towards a proximal end. In accordance with one or more aspects described herein, the distal portion of catheter 900 can be fabricated of a softer, pliable plastic or other material while the proximal portion can be fabricated of a harder, more rigid material to prevent damage to the transducer handle and keep its cable connections secure. Needle channel 930 can be fabricated completely out of a softer, pliable plastic or other similar material, except for a hub 945 at the operator end, which can be made of harder plastic. Hub 945 can have a Luer lock or a straight connection to other devices or, for example, a guide wire at the proximal end. In an exemplary embodiment, hub 945 can have an overhanging edge all around needle channel 930 except for the region abutting the handle chamber 830 in the case where the transducer has a handle or imaging channel 805 in the case where the transducer does not have a handle. The stainless steel needle 908 may be partially withdrawn to point 920(1) and a pre-biased guide wire introduced into an auxiliary lumen so that the entire distal end may bend to a predetermined shape according to the biased guide wire. Moreover, although not shown, flexible shape memory alloys may be utilized as taught by U.S. Pat. No. 7,115,092 to provide compliant catheter structures 900.

Figure 10A:
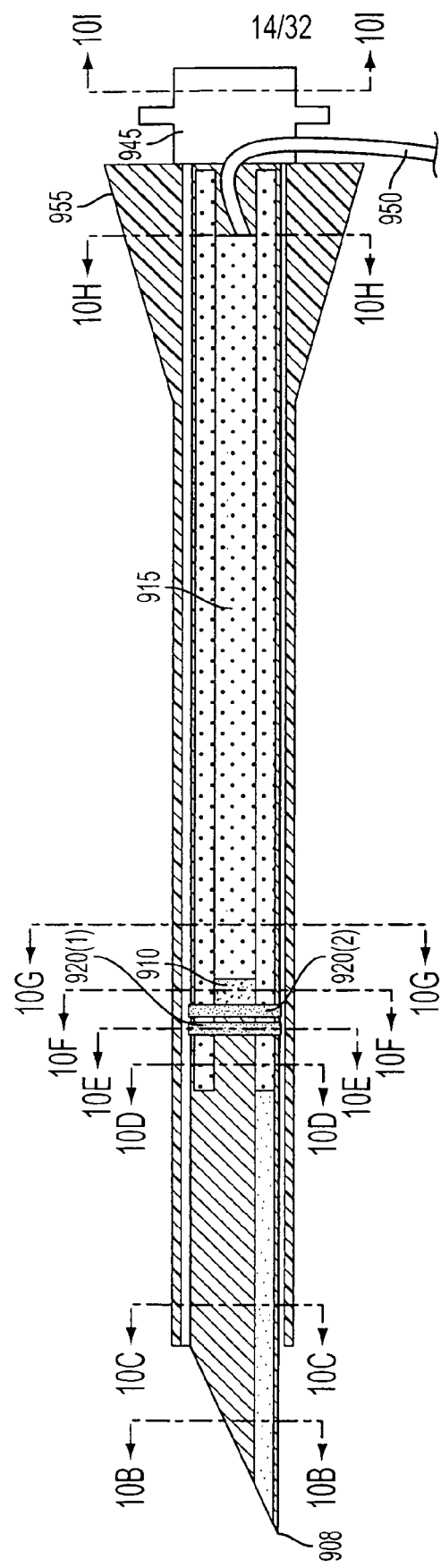
FIG. 10 provides a further exemplary embodiment of the image guided catheter apparatus of FIG. 9 having an outer sheath whereby a transducer lumen may be used for image guidance and then the transducer replaced, once a region of interest is reached, with another transducer or interventional devices, the embodiment further comprising a needle channel, needle buffers and further channels for guide wires or aspiration, the proximal end including a luer lock for attaching a syringe, the drawing further providing eight (8) cross-sectional views.

FIG. 10(A) supports a further exemplary embodiment of the image guided catheter apparatus of FIG. 9 having an outer sheath 905 whereby a transducer lumen 915 may be used for image guidance and then the transducer 910 replaced, once a region of interest is reached, with another transducer or interventional devices, the embodiment further comprising a needle assembly 908, needle buffers 920(1) and 920(2) and further channels, 925, 930 for guide wires or aspiration, the proximal end including a luer lock 945 for attaching a syringe, the drawing further providing eight (8) cross-sectional views of FIGS. 10(B) through 10A(I) explained as follows.

Alternative cross-sectional embodiments may comprise needle 908 where and lumen 930 with a pressure sensor 931 and a temperature sensor 932 on each side shown in FIG. 10(B). Needle 908, lumen 930 with pressure sensor 931 and temperature sensor 932 on each side, such that each sensor is attached to a signal wire within the outer sheath 905 are shown in cross-sectional FIG. 10(C). Additional lumen not shown may be for introducing a further image-guided catheter to penetrate to a depth beyond the depth reached by the catheter/sheath depicted in FIG. 9. Needle 908, lumen 930 with pressure sensor 931 and temperature sensor 932 on each side, such that each sensor is attached to a signal wire within the outer sheath 905 at level of connector channel/lumen 925, are shown in FIG. 10(D). Needle 908, lumen 930 with pressure sensor 931 and temperature sensor 932 on each side, such that each sensor is attached to a signal wire within the outer sheath 905 at level of buffer plates 920(2) (or 920(1)) are shown in FIG. 10(E). Needle 908, lumen 930 with pressure sensor 931 and temperature sensor 932 on each side, such that each sensor is attached to a signal wire within the outer sheath 905 at level of transducer element 910 at distal end of lumen 915 with connector channel/lumen 925 alongside are shown in FIG. 10(F). Needle 908, lumen 930 with pressure sensor 931 and temperature sensor 932 on each side, such that each sensor is attached to a signal wire within the outer sheath 905 at level of imaging channel or lumen 915 with connector channel/lumen 925, alongside are shown in FIG. 10(G). Needle 908, lumen 930 with pressure sensor 931 and temperature sensor 932 on each side, such that each sensor is attached to a signal wire within the outer sheath 905 at level of plastic hub 955 where the hub 955 is at the proximal or operator end of the sheath 905 are shown in FIG. 10(H) and can be used to connect a syringe, for example, after the needle assembly is removed. Also shown is connector channel 925 and a cable connection, center black dot 950, (not required in a wireless embodiment) of the transducer 910 are shown. FIG. 10(I) shows in cross-section, the luer lock 945 end to which, for example, a syringe (not shown, may be connected. The syringe, for example, is attached to the luer lock or proximal end to assist the surgeon during needle introduction into the body under ultrasound guidance. The syringe will provide leverage and transmit force and torque as necessary into the body so as to advance the needle through body tissue. Since the connector channels also exit at the proximal end, contents of the syringe, (for example, anesthesia) can be delivered through the front end of the needle. Similarly, if the needle 908 is advanced into a fluid filled cavity, the fluid contents can be evacuated by suction applied using the plunger of the syringe. If additional devices need to be delivered to the target zone, then the syringe is disconnected, a guide wire is introduced through a connect channel, lumen, and out of the distal end of the needle 908 into the hollow or solid structure (target location). Then the needle assembly 908 is withdrawn leaving the guide wire in place such that the distal (patient) end of the guide wire is retained in the target location. Another interventional or other device or catheter can then be threaded over this guide wire to the target location.

Channel 930 is provided with a temperature sensor 931 and/or a pressure sensor 932 for sensing, for example, the surface of the pericardial lining or other body wall to supplement visual sighting and its temperature for comparison with expected temperature readings, for example, when the catheter makes contact with the pericardial lining. The data from the sensors 931 or 932 are transmitted via signal wires (or wirelessly) to a remote server for analysis by a surgeon or other medical personnel. Conceivably, the sensors can be used to locate tumors. The tumor is located by comparing the temperature reading from the sensor with a known internal temperature map of the human body at ambient room temperature. The deviation in temperatures at a specific location may provide early detection of a tumor. If the tumor is caught early, appropriate medical personnel may diagnose the problem and likely deter further medical risks. Additional lumen (not shown) may connect to a distal microphone for Doppler effect ultrasound detection, for measuring heartbeat or for guidance, for example, to detect proximity to a blood vessel.

Alternatively, if no guide wire 1220 is needed and only fluid evacuation is necessary, then the plastic sheath 905 is advanced under vision such that the distal tip of the plastic sheath 905 is in the desired target location (plastic being atraumatic, protecting sensitive areas). The needle assembly 908 is then withdrawn carefully leaving the distal tip of the plastic sheath 905 in place. A syringe (not shown) is now attached to the luer lock 945 hub of the sheath 905 and fluid drained from and/or drugs delivered into the target location.

Figure 11A:
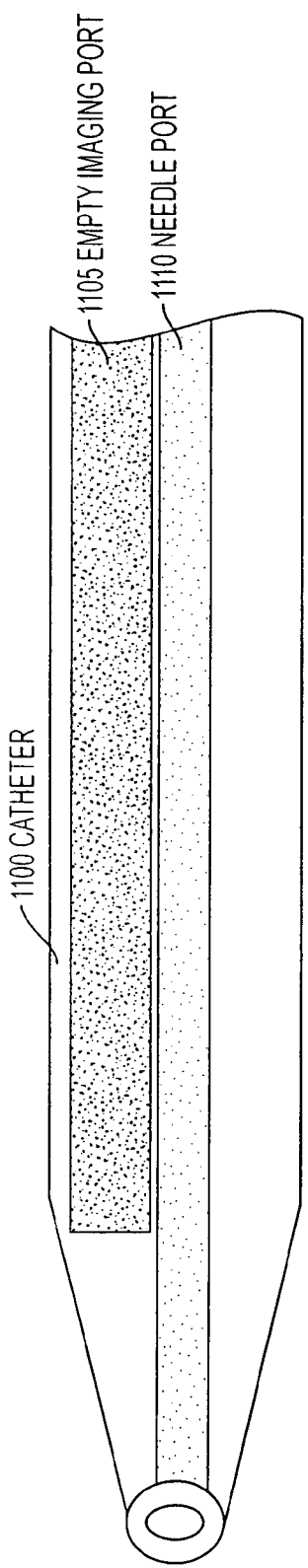
FIG. 11 provides a further exemplary embodiment of the image guided catheter apparatus of FIG. 9 having an empty imaging port 1105 and a needle port (FIG. 11A) where a transducer ridge 1115 mates with a groove 1120 of imaging port 1105 to provide secure and fixed placement of a replacement transducer within an image guided catheter 1100 (the distal end thereof being shown)
FIG. 11B shows a cross-sectional view and FIG. 11C shows longitudinal detail of an imaging channel 1105 including a ridge 1115 of an enclosed transducer.
Figure 11C:
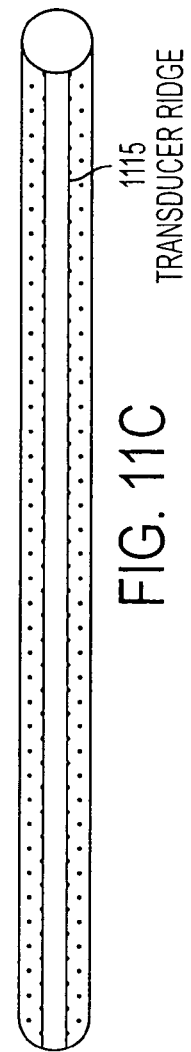
Figure 11B:
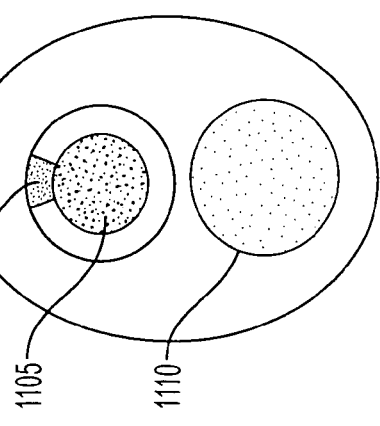

FIG. 11 provides a further exemplary embodiment of the image guided catheter apparatus of FIG. 9 or 10. A transducer ridge 1115 mates with a groove 1120 of an imaging port 1105 of catheter 1100 to provide secure and fixed placement of a replacement transducer within an image guided catheter 1100 (the distal end thereof being shown). FIG. 11B shows a cross-sectional view showing needle port 1110 and imaging port 1105 for respective channels or lumen. FIG. 11C shows longitudinal detail of an imaging channel including a ridge 1115 of an enclosed transducer 1105.

FIG. 12 provides a further exemplary embodiment of the image guided catheter apparatus of FIGS. 9 and 10 showing a plurality of steps for target area access comprising FIGS. 12(A) through 12(H). The entire assembly is preferably wireless, although cord 950 is shown for replaceable transducer 910. The wireless circuitry may be housed in hub 955 and have connectors for mating with connectors of the transducer assembly which is received in lumen/imaging channel 915.

Figure 12A:
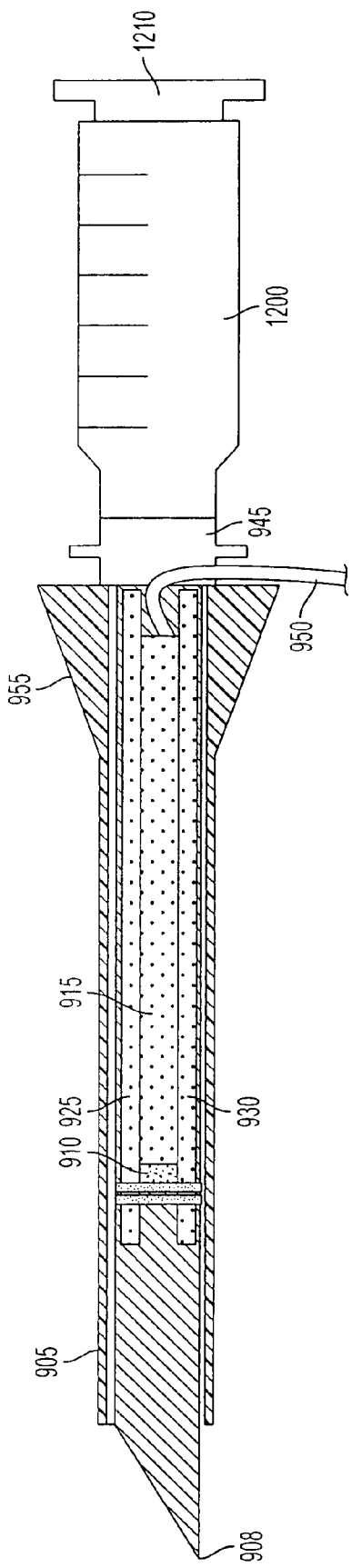
FIG. 12 provides a further exemplary embodiment of the image guided catheter apparatus of FIG. 9 showing a plurality of steps for target area access comprising FIGS. 12(A) through 12(H).

Per FIG. 12(A), the entire assembly including needle assembly 908, ultrasound image guiding ultrasonic transducer 910 and syringe 1200 with plunger 1210 may be advanced into, for example, the pericardial space from the chest with or without associated surface guidance per FIG. 13. At least the assembly portion to be introduced into the body may be preheated to body temperature. A surgeon may guide the catheter and needle by holding the syringe 1200 which is fixed to luer lock 945. Imaging zone 975 is not shown for simplicity.

Figure 12B:
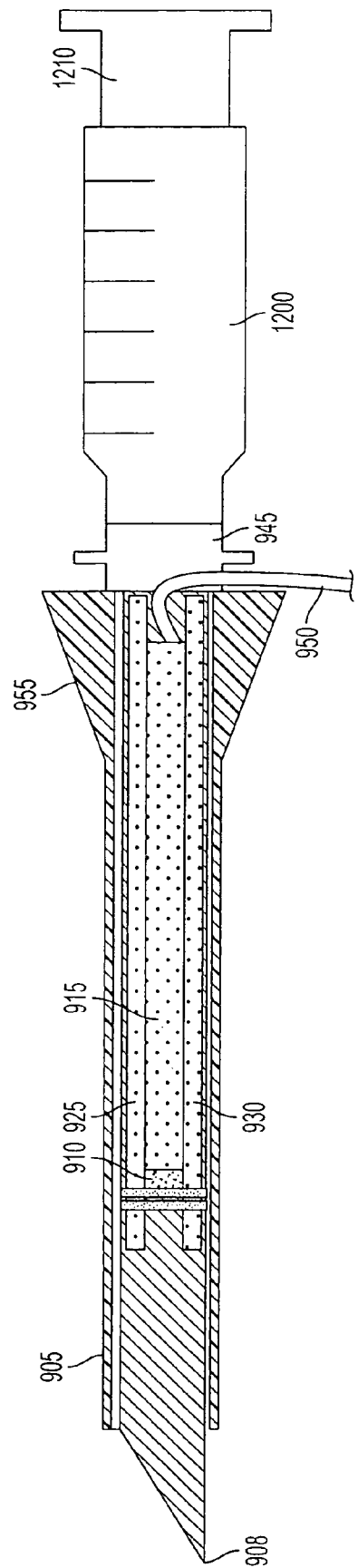
Figure 12C:
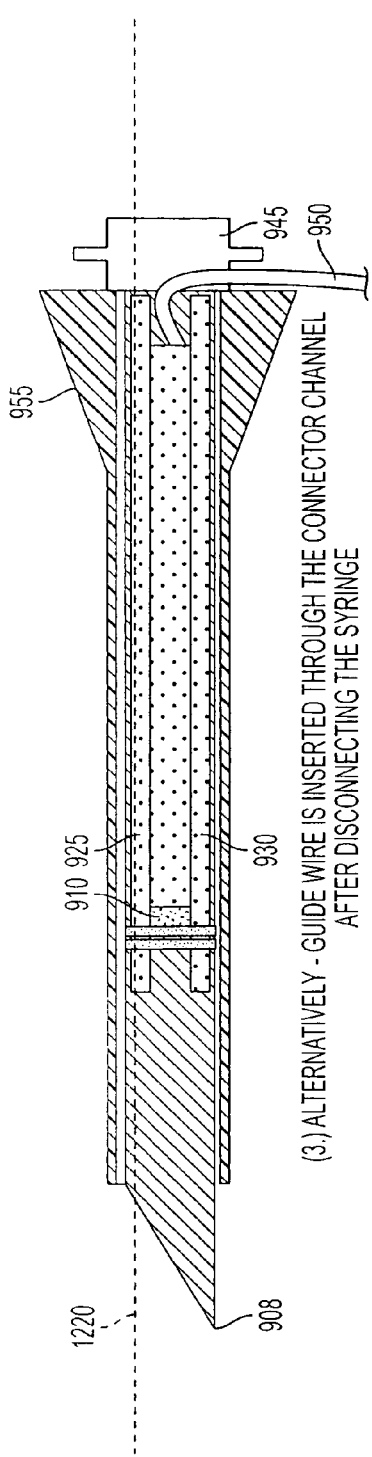
Figure 12D:
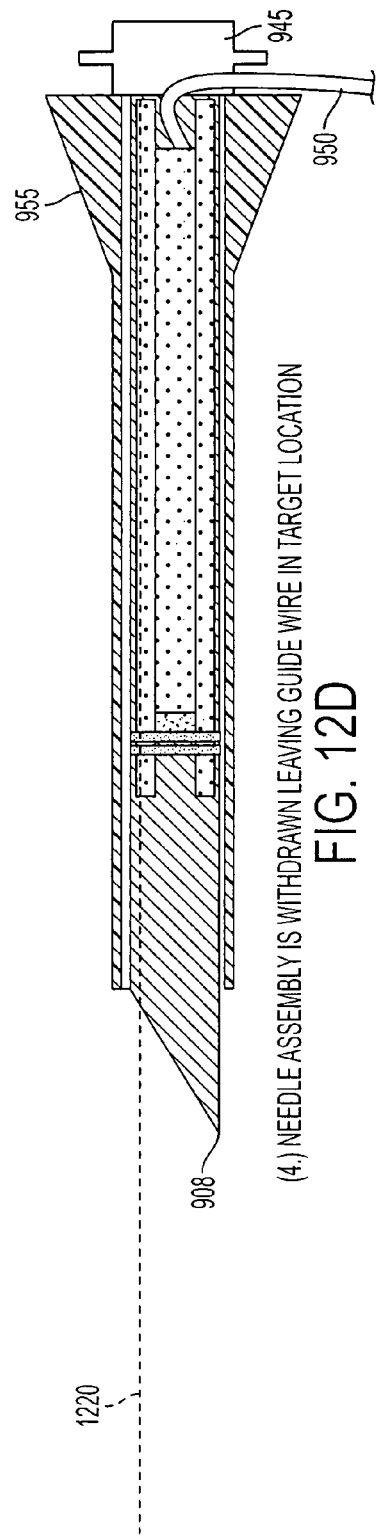
Figure 12E:
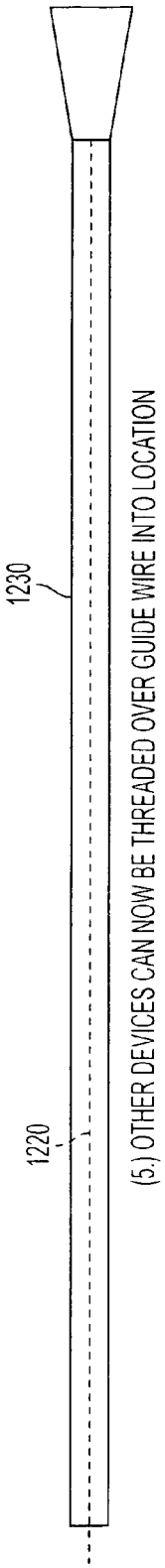
Figure 12F:
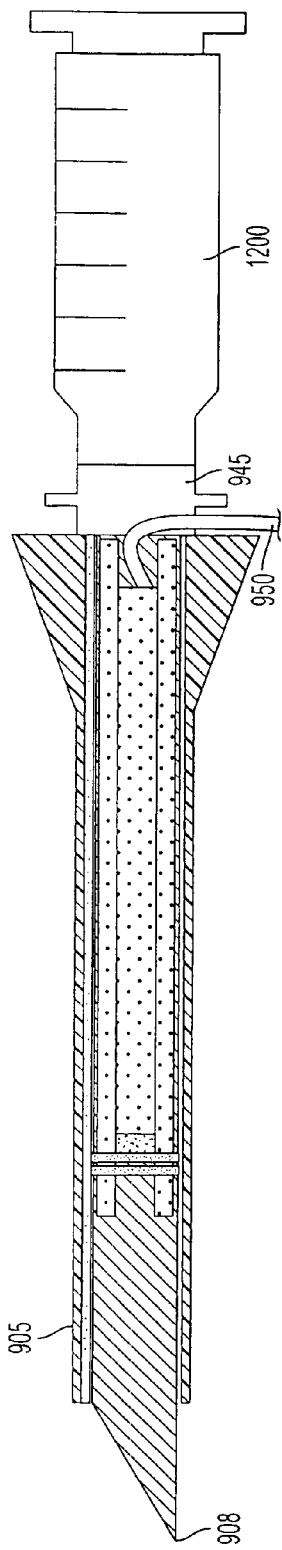
Figure 12G:
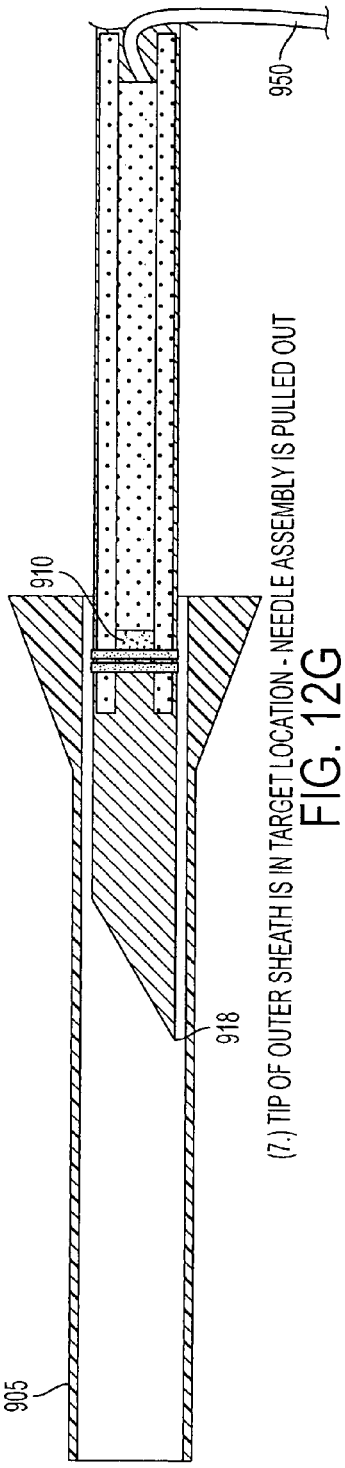
Figure 12H:
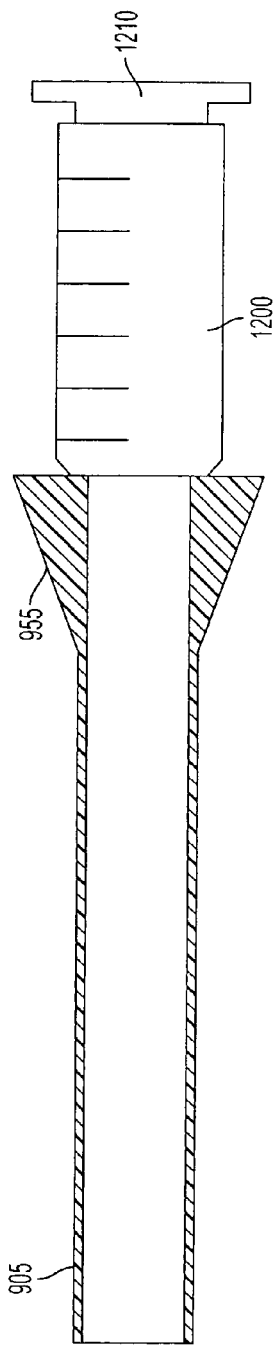

Per FIG. 12(B), the device is advanced toward the target with the assistance of internal ultrasound and/or optic and potentially surface imaging. Once at the target, syringe 1200 via plunger 1210 may be used to deliver drugs, for example, or to evacuate fluid (aspiration). Per FIG. 12(C), alternatively or in addition, a guide wire 1220 may be inserted via connector channel 925 after disconnecting the syringe from luer lock 945. The guide wire may be used to guide interventional devices or many types as described in my patent applications incorporated herein by reference via channel/lumen 925. Per FIG. 12(D), the whole needle assembly may be withdrawn once the guide wire 1220 is in place in a region of interest or target zone/location. Per FIG. 12(E), the guide wire 1220 may now be used for threading devices 1230 over the guide wire to the target location. Per FIG. 12(F), alternatively, after the needle assembly 908 is at the target location, the needle assembly including transducer is withdrawn leaving the plastic outer sheath 905 at the target location. Per FIG. 12(G), the plastic sheath 905 remains in the target location and the needle assembly 908 and transducer 910 is withdrawn. In this regard, balloons may be inflated about sheath 905 as per FIG. 1 to anchor the sheath to an inner wall (not shown). Per FIG. 12(H), with the plastic outer sheath 905 in the target location, a syringe 1200 may be reattached to the sheath 905 to deliver or remove substances (aspiration) from the target zone using plunger 1210.

FIG. 13 provides a further embodiment alluded to in FIG. 6 whereby at least one surface transducer 710, 1320 provides surface guidance imaging zone 1305 and a distal transducer (hidden by surface imaging zone 1305, for example, an image guided catheter/sheath 100, 905 for minimally invasive medical procedures) provides internal imaging zone 975 to a target location. Carrying this concept a step further, catheter/sheath 905 may provide for a further imaging catheter/sheath therein whereby a needle, not shown, may take the imaging further into the depth of a human body to a second internal imaging zone (not shown). A surface transducer 1320 and face 1310 (similar to that depicted in and described by FIGS. 2-5) further provides an anchoring portion similar to anchoring portion 218 (FIG. 1) that is slidably disposed for movement along the length of the outer sheath 905 of the image guided catheter via sleeve or ring 1300. The surface transducer 1310 is moveable and its range may be limited to two to five centimeters from the internal imaging catheter distal tip (distal tip 1330 of outer sheath 905 being indicated). The surface transducer 1310 allows a larger field of view than internal imaging zone 975 of an internal transducer at the distal end of a sheath or catheter (not specifically shown). The surface transducer 1310 may provide a 15 to 20 centimeter depth of field, for example, depending on the tissue composition and surface location of the subject and the frequency range of operation, for example, 100 kHz to 400 MHz or more preferably 1-30 MHz. The surface transducer 1310 may be larger in size than an ultrasound transducer element or array that is included in an imaging channel of the image guided internal catheter/sheath 905 or one included in a catheter/sheath within catheter/sheath 905. Sleeve 1300 may be slidable and be moved to a skin surface position as catheter 905 is moved toward a target location. The rim of transducer 1310 may then serve to anchor image guided catheter/sheath 905 at the target location. The surface mounted transducer 1320, 1310 may be provided with a rotation motor for rotational movement about a ring of the image guided catheter 905. The surface transducer 1320, 1310 can be thus rotated along the cross section of the catheter/sheath 905 so it can potentially follow the progress of the image guided internal catheter/sheath 905 from the surface, thus providing a birds-eye or overall view of the operating field. The surface transducer may be focused as is known in the art to follow the distal tip 1330 as the image guide catheter/sheath 905 is advanced toward a target location. The surface transducer 1310 may be used for imaging or for therapeutic purposes such as heat therapy. The image guided catheter/sheath 905 may be provided with a holder or holster ring 1320 coupled to sleeve 1300 such that the surface transducer 1310 may be replaced as needed with a different transducer having a different purpose or different frequency range of operation.

In operation, a suitable surface transducer 1310 is mounted in its holster or holder 1320. The catheter tip 1330 is positioned at the point of entry into the body. The surface transducer 1310 may be moved longitudinally from a distal end toward the proximal end of the image guided catheter/sheath 905 as the image guided catheter/sheath 905 is advanced into the body toward a target location. A suitable gel may be utilized at skin surface for the surface transducer 1310 and the surface transducer may be fixed to the skin surface via sutures or adhesive. Both surface and internal imaging transducers may provide any known ultrasound imaging capability such as B mode scanning, three or four dimensional scanning and all Doppler modalities, for example, for monitoring fluid movement such as blood. For example, an image-guided catheter/sheath 905 may be inserted from the surface of a female patient's body toward an amniotic sac and be manipulated alone or in conjunction with another or plural remotely manipulatable transducer units 1320 affixed to the female patient's body for safely performing a minimally invasive medical procedure such as an amniocentesis.

Figure 13B:
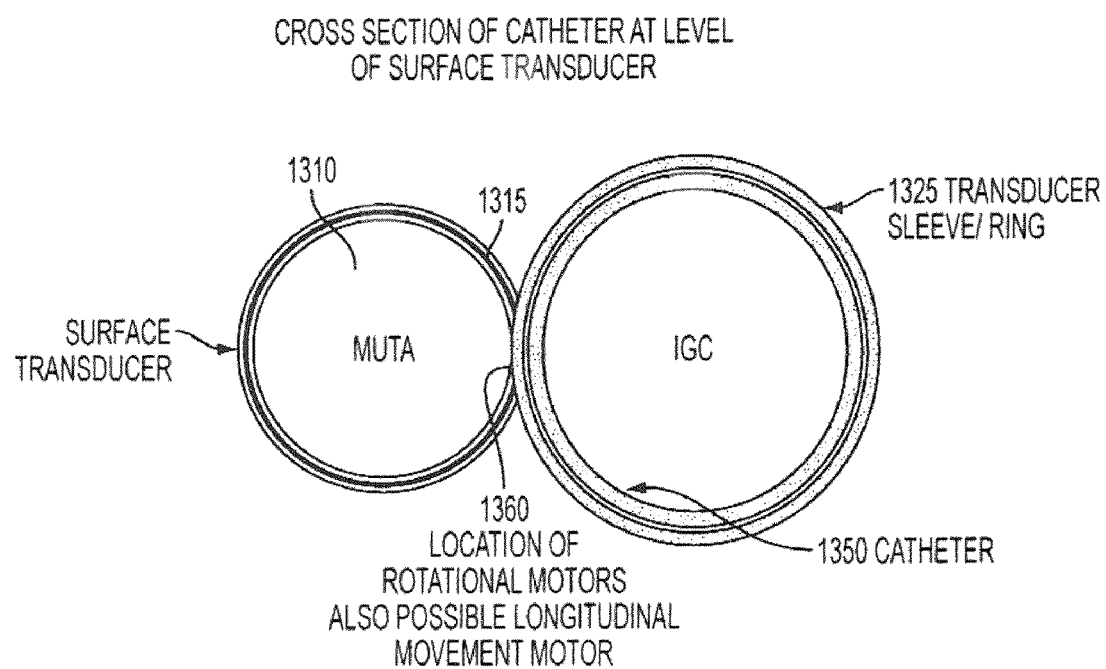
FIG. 13 provides a further embodiment alluded to in FIG. 6 whereby at least one surface transducer 1310 provides deep guidance imaging and a distal transducer, for example, of an image guided catheter or sheath for minimally invasive medical procedures provides close imaging to a target imaging zone, the surface transducer 1310 further comprising an anchoring portion that is slidably disposed for movement along the length of the outer sheath 905 of the image guided catheter and rotational movement about a ring 1300 of the image guided catheter.
FIG. 13A provides a longitudinal view and FIG. 13B provides a cross-sectional view showing possible motors for rotational and longitudinal movement of the surface transducer in relation to the image guided catheter.
Figure 14:
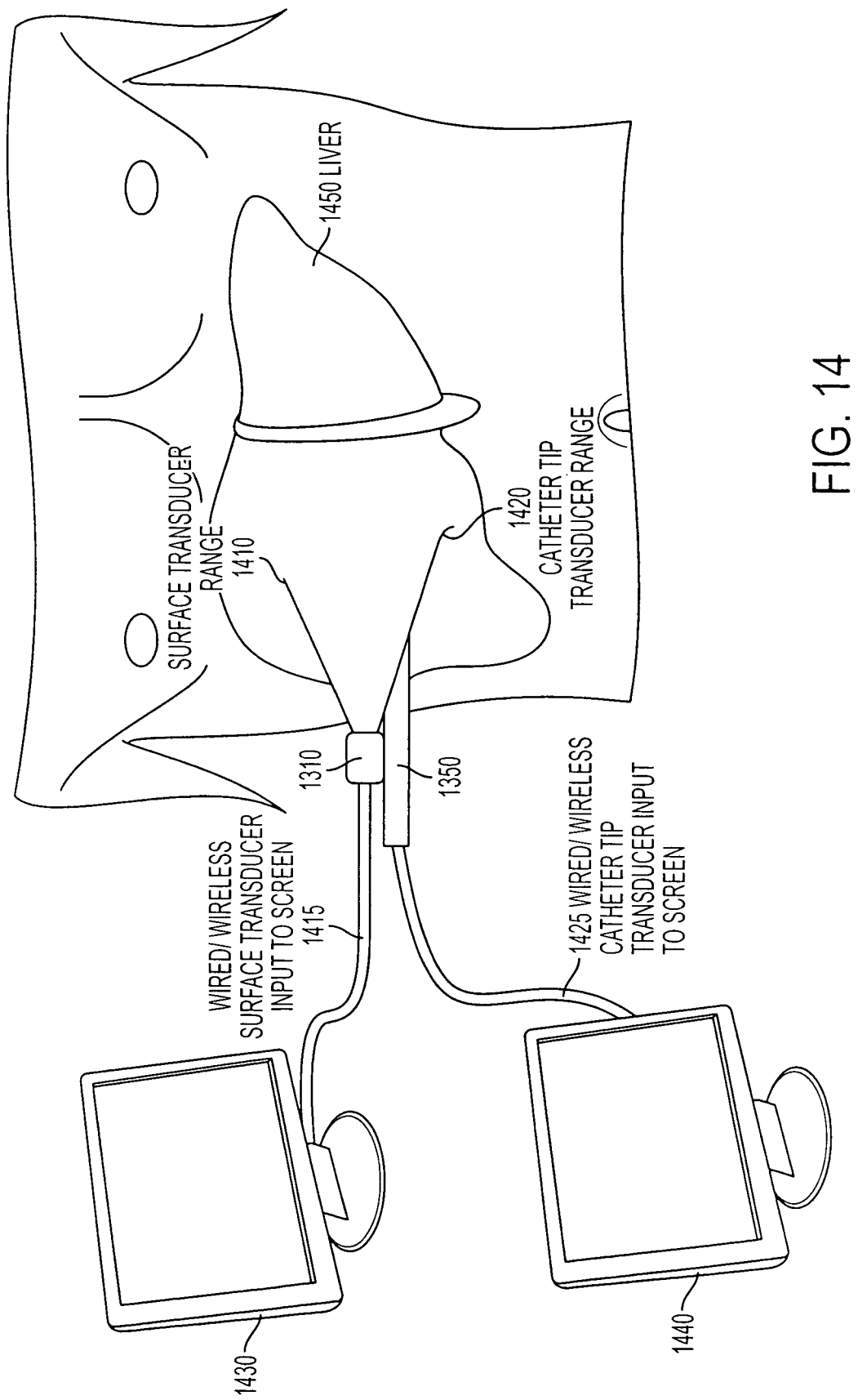
FIG. 14 provides an exemplary use of the embodiments of FIG. 13 for surface and internal imaging and guidance of a catheter for imaging, for example, a liver; preferably connections to displays 1430 and 1440 are not tethered to provide more mobility for a surgeon.

FIG. 13A provides a longitudinal view, and FIG. 13B provides a cross-sectional view showing possible motors 1360 for rotational and longitudinal movement of the surface transducer in relation to the sleeve 1325 of the image guided catheter. Transducer 1310 may in turn rotate within, for example, circular housing 1315 via a rotational motor and twist as necessary to improve surface imaging zone 1305. As seen in the cross-sectional view of FIG. 13B, the transducer sleeve/ring 1325 is slidably disposed on image guided catheter 1350.

FIG. 14 provides an exemplary use of the embodiments of FIG. 13 for surface and internal imaging and guidance of an image-guided catheter 1350 for imaging, for example, a liver. Preferably connections to displays 1430 and 1440 are wireless and not tethered to provide more mobility for a surgeon. Surface mounted transducer 1310 is seen to provide a surface transducer range 1410 and image guided catheter 1350 provides a catheter tip transducer range 1420 of, for example, liver 1450 via individual displays 1430, 1440 of one or more work stations. The work stations and transducers may be uniquely addressed and provide or receive data, for example, via the exemplary data structures of FIGS. 5A and 5B.

Figure 15:
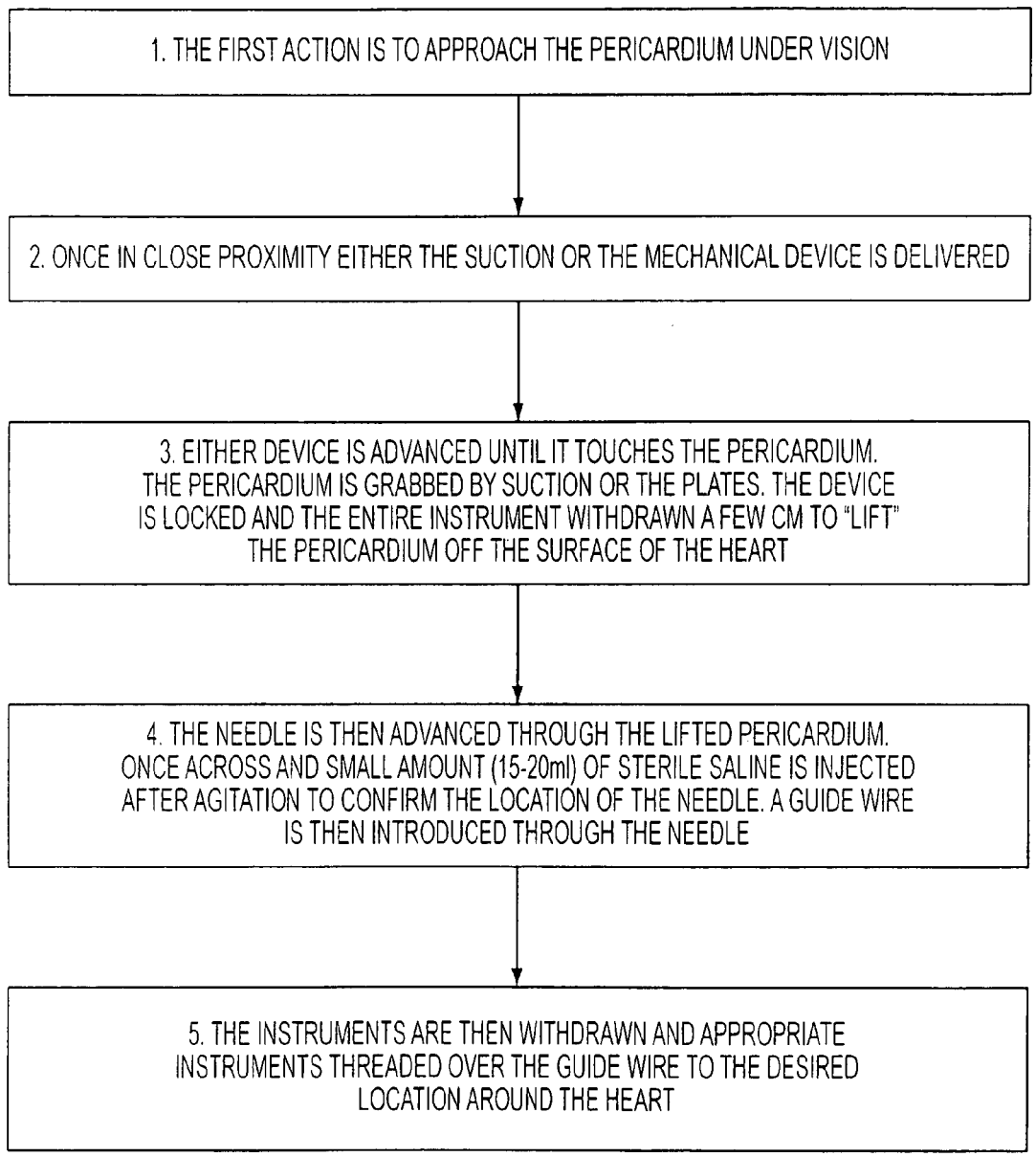
FIG. 15 provides a flowchart for a method of pericardial access in connection with FIGS. 16-18.

Now, procedures and methods and apparatus for pericardial access will be described with reference to FIGS. 15-18. FIG. 15 provides a flowchart for a method of pericardial access, suction and mechanical. An instrument as will be described herein may be a cylindrically shaped instrument made, for example, of metal such as steel or a material of similar tensile strength and properties. There may be two or more channels located inside or outside the basic cylinder shape where outside is not shown. One of the channels may contain an instrument that can grab the pericardial lining mechanically (toothed forceps or similar instrument) or via creating a suction. Either action will secure or lock away from the heart and immobilize the pericardial lining to enable penetration by a needle. Another channel may be imaging channel or plurality of imaging channels for ultrasound or optical imaging. Yet another channel will contain a needle that can be advanced by an operator such as a surgeon and advanced and introduced so as to pierce the pericardial lining which is held immobile by the suction or grasping action described above. Still further additional channels may be provided for delivery of instruments such as videoscopes, diagnostic or therapeutic devices.

Suction channel 1620 of FIG. 16A may be a hollow cylinder that is flat and polished such that it is atraumatic at the distal or patient end. The operator end may have a luer lock or similar attachment that enables connection, for example, to a suction syringe. Drawing the plunger of the suction syringe develops variable amounts of suction or vacuum within the suction channel 1620. The suction syringe may have a lock such that vacuum is maintained without continuous application of manual drawing on the syringe plunger.

The mechanical embodiment is an alternative to the suction channel 1620 that may be used directly if the suction channel does not work to secure the pericardium and involves a forceps. This instrument is located, for example, within the suction channel 1620 and has two flat opposing plates of varying dimensions at the distal or patient end (for example, toothed forceps). These plates may have a rough or toothed opposable surface. The toothed forceps are controlled, for example, by a scissor grip at the proximal or operator end. Activating the grip causes the plates to close and grasp, for example, the pericardial lining. Like the suction syringe, the scissor forceps can also be locked such that ongoing manual pressure is not necessary to maintain a grip on, for example, the pericardial lining. The plates of the forceps are advanced in the open state out of the distal or patient end of the channel. Under vision of ultrasound, for example, the pericardium is grasped by activating the scissor grip. Once secured to the pericardium, the grip is locked.

FIG. 15(1)-15(5) provide details of the operation. Per FIG. 15(1), an initial action is to approach a pericardium under vision, such as both surface and internal ultrasound, optical camera vision and/or OCT or other vision system. The catheter may be preheated to body temperature prior to body entry. Referring to FIG. 17(A), a suction catheter approaches the pericardium under vision with a needle 1608 retracted within the needle channel or lumen 1610. Referring to FIG. 18(A), a mechanical device catheter approaches the pericardium with, for example, toothed forceps retracted within a forceps channel or lumen 1650. The needle 1608 being retracted within needle lumen 1620 in a suction embodiment including a suction channel 1620 is also seen according to FIG. 16A.

Referring to FIG. 15(2), once the device is in close proximity to the target pericardium, either the suction or the mechanical device is delivered. Per FIG. 17(B), suction has already begun and per FIG. 18(B), under vision, forceps 1675 are advanced and opened out of their lumen/channel 1650 and applied to the pericardium. Per FIG. 15(3), either the suction device or the mechanical forceps device are advanced until they touch the pericardium. For example, the pericardium is grabbed by a suction generated within suction channel 1620 or the plates of the mouth of the forceps 1675 grab the pericardium 1700. The suction may be applied and maintained by using a syringe plunger (not shown) or other suction generation or by using lockable forceps controls in the mechanical device (not shown). One or the other device is locked, meaning suction is maintained in constant pressure and the mechanical forceps are not made to bite any further than necessary to grasp the pericardium. Once one or the other device has grasped the pericardium wall 1700, then, the one or the other instrument is withdrawn one or a few centimeters to lift the pericardial lining 1700 from the heart. See FIG. 7, FIG. 17(B), FIG. 18(C) and FIG. 18(D).

Per FIG. 15(4), a needle 1608 of either the suction or mechanical device is then advanced through the lifted pericardium. Per FIG. 16B, there is shown an advancement of needle 1608 out of channel 1610. Per FIG. 17(C), the needle 1608 is seen piercing the lifted pericardium 1700 in a suction embodiment. Per FIG. 18(E), the needle 1608 of the mechanical embodiment is seen piercing the pericardium 1700 above the top of the forceps 1675, still grasping the pericardium wall 1700. Once the needle 1608 has pieced, a small amount of sterile saline solution may be injected via a syringe, not shown, after agitation to confirm the location of the needle 1608. The saline solution may contain a contrast agent to assist vision from surface or internal transducers and may be preheated to body temperature before injection to reduce a possibility of side effects. A guide wire 1630 is then introduced within the pericardial sac 1700 via the extended needle 1608 which is hollow. Per FIG. 16, a guide wire 1630 may be advanced through the needle channel 1610. The guide wire 1630 advancement is seen for a suction embodiment in FIG. 17(D) and in FIG. 18(F) for the mechanical embodiment.

Per FIG. 15(5), once the guide wire 1630 is in place within the pericardium 1700 and in the vicinity of the heart at a preferred approach point per FIG. 7, the suction or mechanical device is withdrawn and interventional instruments appropriate for a given medical procedure may be threaded over the guide wire 1630 to the desired location around the heart under surface and/or internal vision where vision may be ultrasound and preferably via a wireless transducer assembly coupled to either internal or external ultrasound transducer assemblies or an image guided catheter for pericardial access.

Figure 16C:
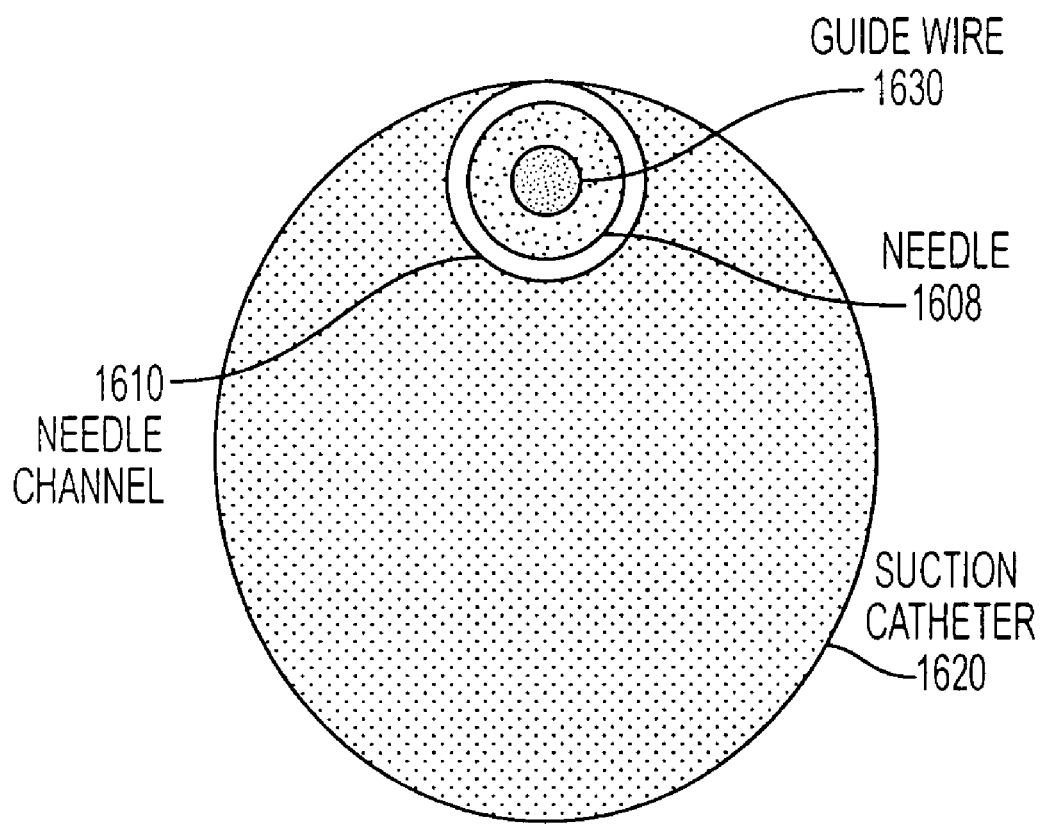
FIG. 16C provides a cross-sectional view of the suction catheter of FIG. 16A.
Figure 16D:
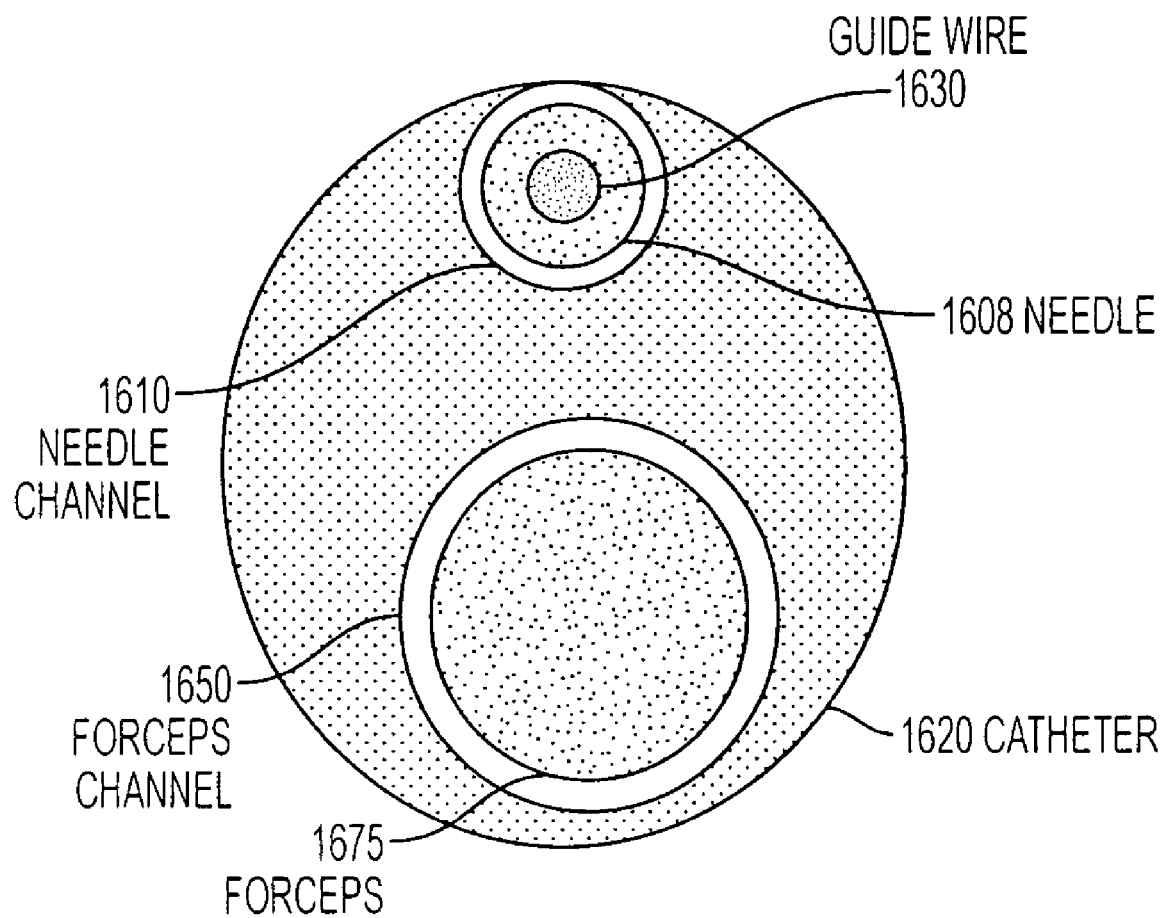
FIG. 16D provides a cross-sectional view of the mechanical catheter of FIG. 16B.

FIG. 16 provides longitudinal views of suction and mechanical embodiments for pericardial access; FIG. 16A relates to a suction embodiment and shows needle 1608, needle channel or lumen 1610 and suction channel 1620. FIG. 16B relates to either a mechanical grasping or suction embodiment using a guide wire 1630 introduced into the pericardium via a needle 1608. FIG. 16C provides a cross-sectional view of the suction catheter of FIG. 16A showing suction catheter 1620, needle channel 1610, needle 1608 and guide wire 1630. FIG. 16D provides a cross-sectional view of the mechanical catheter of FIG. 16B showing catheter 1620 comprising a forceps channel 1650 and forceps 1675 as well as a needle channel 1610, a needle 1609 inserted therein and a guide wire 1630 within the needle 1608. Forceps channel 1650, needle channel 1610 and suction catheter channel or lumen 1620 are shown in circular cross section and may be oval or other shape in cross-section in different embodiments. Also, all embodiments discussed in FIGS. 15-18 should be considered to comprise one or more imaging channels/lumen not shown.

Figure 17C:
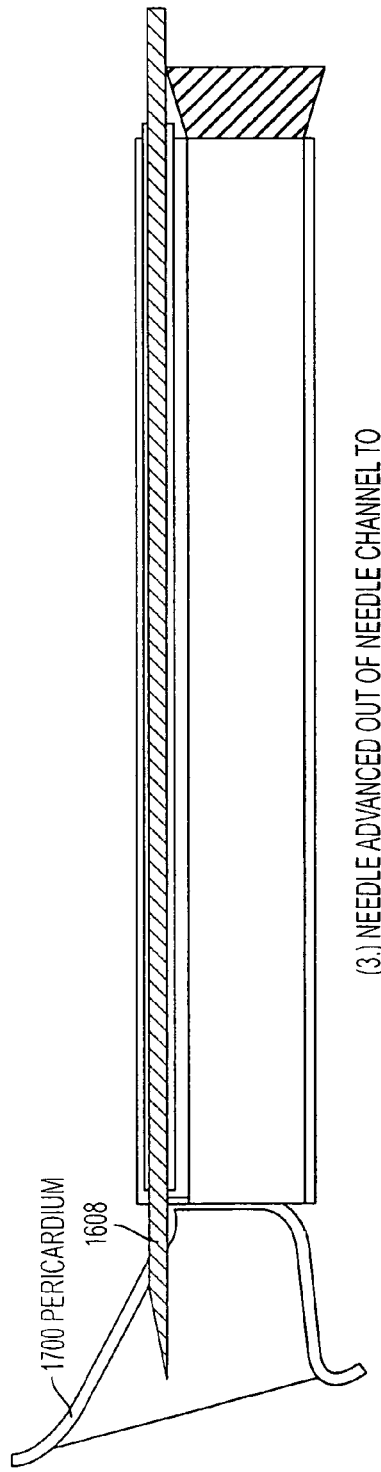
FIG. 17 provides steps of a pericardial access process in accordance with the suction embodiment of FIGS. 16A and 16C comprising FIGS. 17(A) through 17(D).
Figure 17D:
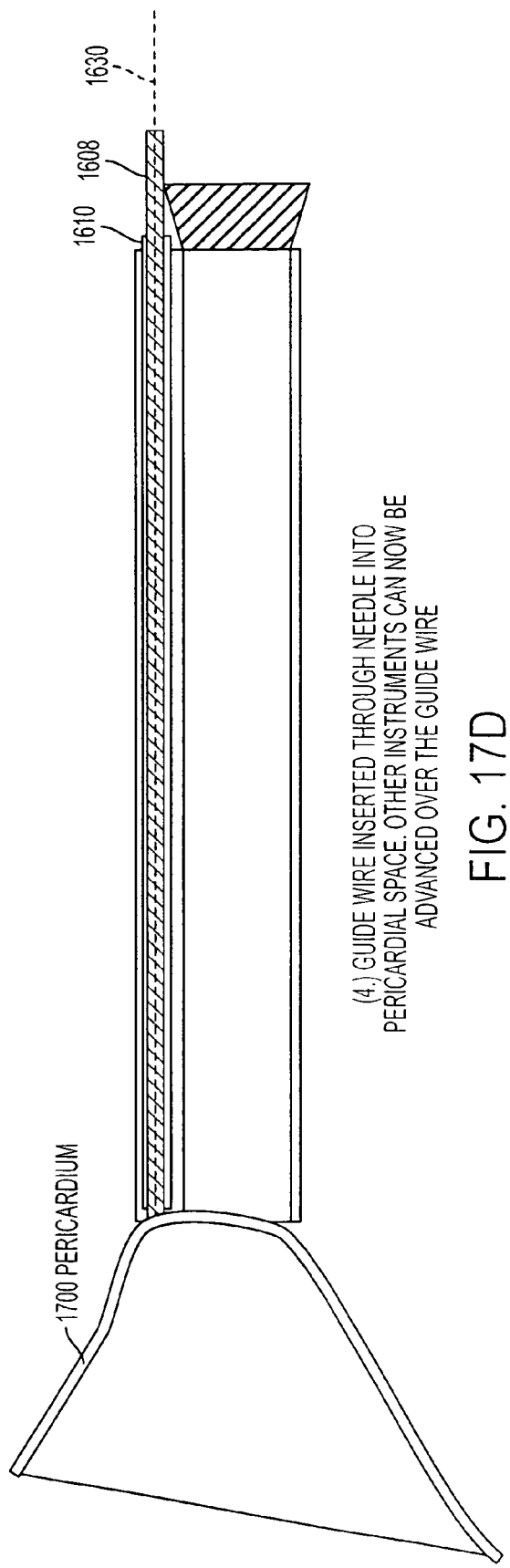
Figure 18A:
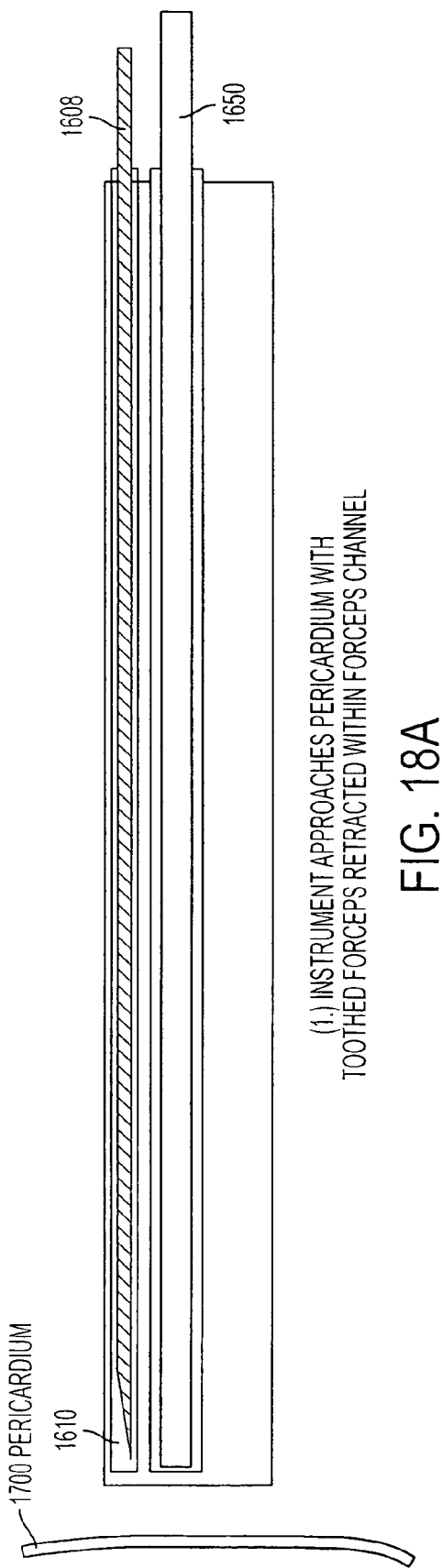
FIG. 18 provides steps of a pericardial access process in accordance with the mechanical embodiment of FIGS. 16B and 16D comprising FIGS. 18(A) through 18(F).

FIG. 17 provides steps of a pericardial access process in accordance with the suction embodiment of FIGS. 16A and 16C comprising FIGS. 17(A) through 17(D). FIG. 17(A) shows the suction catheter approaching the pericardium with the needle retracted within its needle channel or lumen. FIG. 17(B) shows suction being applied to the pericardium. The suction may be activated, for example, via a syringe or a vacuum pump. At this point, the pericardium is secured by the suction and immobile but has been drawn by the suction approximately one or more centimeters from its position in FIG. 17(A). FIG. 17(C) represents a further withdrawing of the pericardial lining by suction and a piercing of the lining by a needle, advanced out of the needle channel to pierce through the pericardium into the pericardial space or cavity with the heart. See FIG. 7. FIG. 17(D) shows advancement of a guide wire inserted via and through the needle into the pericardial space. Once the guide wire is in place, interventional devices may be threaded over the guide wire.

Figure 18B:
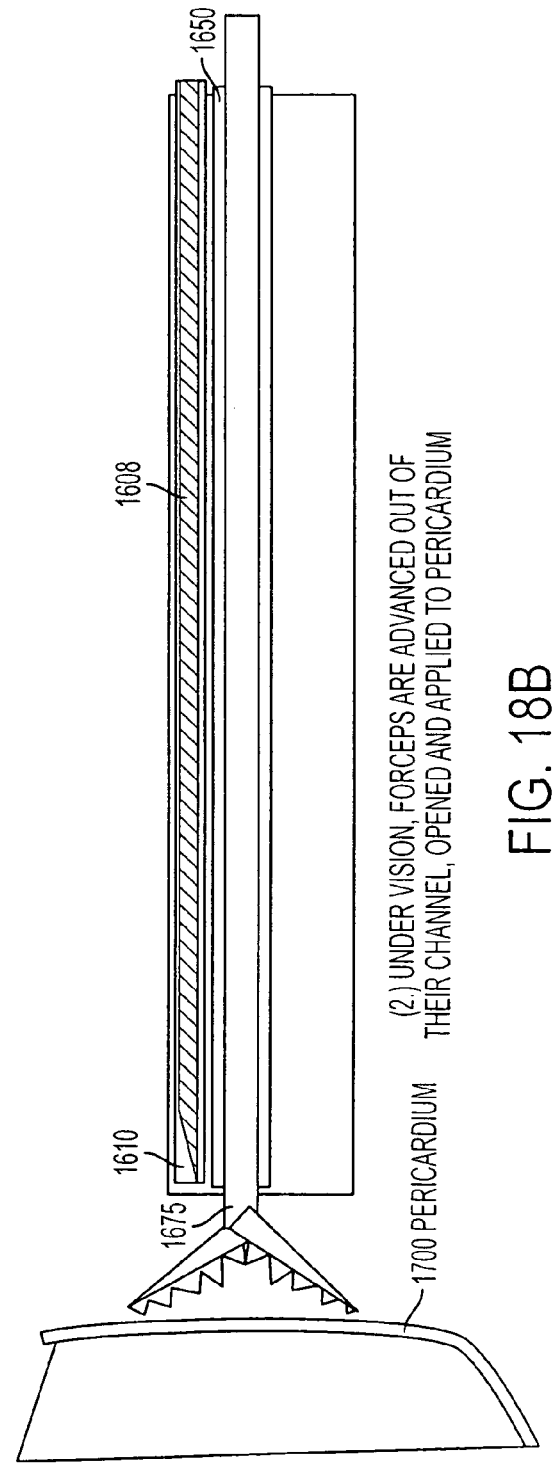

FIG. 18 provides steps of a pericardial access process in accordance with the mechanical embodiment of FIGS. 16B and 16D comprising FIGS. 18(A) through 18(F). FIG. 18(A) shows the mechanical instrument approaching the pericardium with tooth forceps retracted within a forceps channel 1650 (FIG. 16D). Per FIG. 18(B), under vision from surface or internal transducers or both, the forceps are advanced out of their channel, opened and applied to the pericardium (pericardial lining per FIG. 7). Per FIG. 18(C), under vision, the forceps are activated to grab a portion of the pericardial lining an pull it away from the heart, for example, by a centimeter or more, the device may be withdrawn slightly to perform the grabbing and withdrawal. As per FIG. 18(D), the closed toothed forceps are retracted within the forceps channel 1650 to immobilize and secure the pericardial lining that has been grasped. This is a closed or activated state of the toothed forceps in combination with the forceps channel 1650. Per FIG. 18(E), a needle of needle channel 1610 is advanced just above the closed forceps through the pericardial lining into the cavity with the heart. See FIG. 7. Per FIG. 18(F), a guide wire 1630 may be advanced through the needle 1608 into the pericardial cavity with the heart. To release the grasp of the forceps, the needle assembly and forceps channel can be withdrawn and twisted to open the forceps, leaving the guide wire for threading interventional devices.

Figure 19:
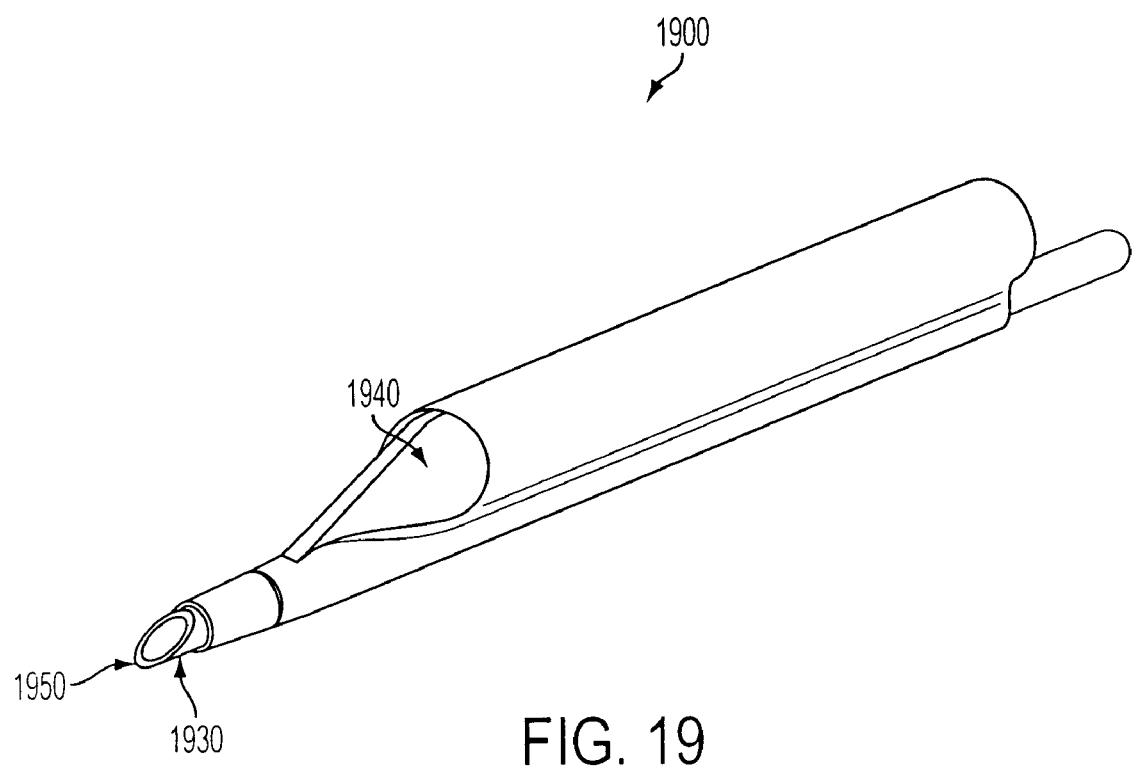
FIG. 19 provides a perspective view of an embodiment of an image guided catheter/sheath including a needle which may be moved beyond a distal tip.

FIG. 19 provides a 3 dimensional view of the preferred embodiment of an image guided catheter 1900. In particular, the imaging channel 1940 is preferably located above the needle channel 1930. It is known to those in the art that changing orientation of the image transducer in relation to the needle channel 1930 may be necessary in order to accommodate the patient or the situation. The image transducer 1910 (not shown), located within the imaging channel 1940, can project tissue images and/or any image placed in front of the catheter's view. The needle channel 1930 with a tip 1950 provides a cutting front that allows an operator to push or manipulate the entire catheter to the correct location, guided by the imaging channel 1940. Also the image transducer 1910 will be able to image the tip 1950 of the needle channel 1930. Thus, the operator is cognizant of exactly where the needle is located in the general area in front of the entire catheter 1900.

The principles of application of the several discussed embodiments of a remotely manipulatable medical imager and image guided catheter for, for example, pericardial access may be extended to other embodiments such as infrared temperature imaging and optical coherence tomography imaging so long as the assembly for remotely manipulating and capturing images may be sufficiently small in size to permit comfortable attachment or wearing on or within the body. For example, any active or passive medical imaging device for remote manipulation should be as small as possible just as circuitry and motors for control, recording and transmission of imaging may be made as small in size as possible. These and other features of embodiments and aspects of a remotely manipulatable ultrasound transducer or transducer array assembly for internal and/or surface imaging and pericardial or other cavity access may come to mind from reading the above detailed description and any claimed invention should be only deemed limited by the scope of the claims to follow.

What I claim is:

1. A. system for use in a minimally invasive medical procedure comprising a manipulatable ultrasound transducer assembly configured to provide a transducer range of imaging a human body from a skin surface of the human body when in use, the manipulatable ultrasound transducer assembly for wirelessly communicating with a remote workstation including a display wherein said assembly comprises at least one transducer element for collecting ultrasound images within the transducer imaging range, the manipulatable ultrasound transducer assembly further comprising:

a motor configured for rotating said at least one transducer element responsive to motor control data received from said remote workstation, the motor configured to rotate the at least one transducer in a plane parallel to a body part of the human body to be imaged when said manipulatable transducer assembly is located at the external human body skin surface during use, and a housing for said at least one transducer element and said motor, said housing having a relatively smooth surface configured for fixation to said external human body skin surface; and the system further comprising an image guided catheter configured for internal human body imaging structurally interconnected to said manipulatable ultrasound transducer assembly, the image guided catheter for communicating with said remote workstation including said display, the image guided catheter comprising an elongate body having a tapered tip at a distal end of the elongate body and an ultrasound transducer element located at an outer periphery of the tapered tip of the elongate body and oriented to provide a forward imaging zone, the forward imaging zone including an image of an insertable needle extending from an end aperture at the distal end of the tapered tip.

2. The system as recited in claim 1 further characterized by said manipulatable ultrasound transducer assembly comprising a second motor for twisting said at least one transducer element from a default position, said at least one transducer element configured for directing sound waves into the human body to be imaged from the external skin surface to which it is fixed, to another angular position, said at least one transducer element configured for directing sound waves from said external human body skin surface according to one of an input incremental and final angle of direction of twist to said second motor for twisting via said remote workstation.

3. The system as recited in claim 2 further characterized by said motor for rotating said at least one transducer element being capable of rotating said array from a default position, said at least one transducer element configured for directing sound waves from the external human body skin surface to which it is fixed into the human body to be imaged, to another rotational angular position, said at least one transducer element configured for directing sound waves from said human body skin surface according to one of an input incremental and final angle of rotation.

4. The system as recited in claim 2 further characterized by a third x axis motor and a fourth y axis motor for moving said at least one transducer element in two directions within a two-dimensional footprint of the housing on the human body skin surface.

5. The system as recited in claim 2, the manipulatable ultrasound transducer assembly further comprising a third x axis motor and a fourth y axis motor wherein said housing is further characterized by:
a rod assembly in the form of a rectangle comprising two pairs of parallel rods,
each parallel pair of rods conducting a further perpendicular rod member in one of two directions, the at least one transducer element for further connection to the juncture of two perpendicular rod members, the two perpendicular rod members configured for movement of the at least one transducer element as determined by the x axis and y axis motors in a plane approximately parallel to the skin surface of the human body to which the manipulatable ultrasound transducer assembly is to be fixed, the first rotation motor and the second twist motor being located at the perpendicular rod member juncture.

6. The system as recited in claim 1 further characterized by said image guided catheter comprising a sleeve surrounding said image guided catheter for structurally interconnecting to said manipulatable ultrasound transducer assembly.

7. The system as recited in claim 6 further characterized in that said image guided catheter is adapted for insertion in a human body cavity, said manipulatable transducer assembly comprising a longitudinal axis and a longitudinal axis motor for moving said at least one transducer element of said manipulatable transducer assembly along a longitudinal axis of the image guided catheter according to one of an incremental distance from a default position and a desired final position.

8. The system as recited in claim 1 wherein said motor for rotating is further characterized by an angle of rotation up to 180 degrees for collecting image data of a plurality of image planes.

9. The system as recited in one of claim 1 for cooperating with a second such manipulatable transducer assembly fixed to a second position about said image guided catheter further characterized by a capability of the cooperation, configured for providing three-dimensional, stereoscopic imaging of a region of interest of said human body to be imaged.

10. The system of claim 1 wherein the motor for rotating is further characterized by an associated gear assembly for accurate movement of one of said at least one transducer element and an array of transducer elements including said at least one transducer element of the manipulatable transducer assembly in relation to said image-guided catheter.

11. The system as recited in claim 10, the manipulatable transducer assembly being wirelessly and remotely manipulatable further characterized by:
a wireless transceiver for communicating with said remote workstation and for controlling said motor for rotating in response to motor control data received from said remote workstation;
a controller for receiving the motor control data from said transceiver and controlling said motor responsive to receipt of said motor control data to relocate one of said at least one transducer element and said transducer element array; and
a battery power supply for powering components of the remotely manipulatable transducer assembly requiring power.

12. The system as recited in claim 11, further characterized by:
an antenna, connected to said wireless transceiver, for receiving wireless radio signals including said motor control data from said remote workstation and configured for transmitting wireless radio signals including output image data of said human body to be imaged by the at least one transducer element to said remote workstation via said wireless transceiver antenna.

13. The system as recited in claim 12 further characterized in that
said output of said manipulatable transducer assembly is compressed at a data compressor prior to one of transmission via said transceiver and of storage in memory.

14. The system as recited in claim 11 further characterized in that
said wireless transceiver reports actual motor rotational position data of said manipulatable transducer assembly to a said remote workstation.

15. The system as recited in claim 1, the manipulatable transducer assembly being remotely controllable, the manipulatable transducer assembly further characterized by:
a controller for controlling said motor for rotating of said manipulatable transducer assembly according to wireless remote control input;
a battery power supply for powering components of the manipulatable transducer assembly requiring power and;
a memory for temporary storage of image data from one of said at least one transducer element and a transducer array including said at least one transducer element.

16. The system as recited in claim 1, wherein one of said manipulatable transducer assembly and said image guided catheter is further characterized by:
a unique identification code for uniquely identifying said one of said manipulatable transducer assembly and of said image guided catheter to the remote workstation.

17. The system as recited in claim 1 characterized by said at least one transducer element of said manipulatable transducer assembly and said ultrasound transducer element of said image guided catheter outputting image data to a plurality of display screens of said remote workstation.

18. The system of claim 1 characterized by cooperation between said image guided catheter and said remote workstation, the image guided catheter having one of a suction channel and a biopsy forceps channel configured for manipulation of the human body to be imaged under remote workstation control.

19. The system as recited in claim 1 wherein the image guided catheter has a cross-section in the μm range and a pliable portion at the distal tip, a withdrawable needle and a lumen for introducing a biased guide wire for bending the distal tip.

* * * * *